United States Patent [19]

Iwaki et al.

[11] Patent Number: 5,200,109
[45] Date of Patent: Apr. 6, 1993

[54] MESOMORPHIC COMPOUND, LIQUID CRYSTAL COMPOSITION CONTAINING SAME AND LIQUID CRYSTAL DEVICE USING SAME

[75] Inventors: Takashi Iwaki, Isehara; Takao Takiguchi, Tokyo; Shinichi Nakamura; Yoko Yamada, both of Atsugi; Takeshi Togano, Yokohama; Shosei Mori, Atsugi, all of Japan

[73] Assignee: Canon Kabushiki Kaisha, Tokyo, Japan

[21] Appl. No.: 820,811

[22] Filed: Jan. 15, 1992

Related U.S. Application Data

[63] Continuation of Ser. No. 585,530, Sep. 20, 1990, abandoned.

[30] Foreign Application Priority Data

Sep. 22, 1989 [JP] Japan .................................. 1-245012
May 15, 1990 [JP] Japan .................................. 2-123149

[51] Int. Cl.$^5$ ..................... C09K 19/34; C09K 19/30; C07D 285/12
[52] U.S. Cl. .......................... 252/299.61; 252/299.63; 252/299.66; 548/136; 548/142
[58] Field of Search ...................... 252/299.01, 299.61, 252/299.63, 299.66, 299.67; 359/103, 104; 544/298, 335; 548/136, 142

[56] References Cited

U.S. PATENT DOCUMENTS 4,367,924 11/1983 Clark et al. ........................... 359/104
5,034,151 7/1991 Shinjo et al. ..................... 252/299.61

FOREIGN PATENT DOCUMENTS

| | | |
|---|---|---|
| 107216 | 8/1981 | Japan . |
| 193426 | 11/1984 | Japan . |
| 193427 | 11/1984 | Japan . |
| 156046 | 8/1985 | Japan . |
| 156047 | 8/1985 | Japan . |
| 245142 | 10/1986 | Japan . |
| 242724 | 11/1986 | Japan . |
| 246722 | 11/1986 | Japan . |
| 246723 | 11/1986 | Japan . |
| 249024 | 11/1986 | Japan . |
| 249025 | 11/1986 | Japan . |
| 051644 | 3/1987 | Japan . |
| 045258 | 2/1988 | Japan . |
| 222148 | 9/1988 | Japan . |
| 061472 | 3/1989 | Japan . |
| 88/08019 | 10/1988 | World Int. Prop. O. . |

OTHER PUBLICATIONS

CA:94:174993g "Liquid crystalline 1,3,4-thiadiazoles" Dimitrova et al. 1981.
CA:111:68082u "2,5-Disubstituted 1,3,4-thiadiazoles having extended smectic C phases, their preparation and their use in ferroelectric LC mixtures" 1989.
Helv. Chim. Acta., vol. 39, No. 59 (1956) 504:13.
Helv. Chim. Acta., vol. 40, No. 249 (1957) 2428:33.
Appl. Phys. Lett., vol. 18, No. 4 (Feb. 1971) 127:28.
R. Tschesche and W. Fuhrer. Chem. Ber. vol. III (1978) 3502:05.
P. B. Rasmussen et al., Bull. Soc. Chim. de France, No. 1 (1985) 62:65.

Primary Examiner—Robert L. Stoll
Assistant Examiner—Shean C. Wu
Attorney, Agent, or Firm—Fitzpatrick, Cella, Harper & Scinto

[57] ABSTRACT

A mesomorphic compound represented by the following formula (I):

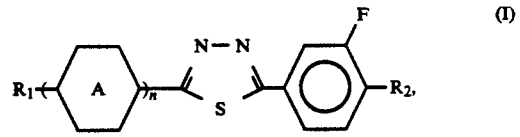

wherein $R_1$ and $R_2$ respectively denote a linear or branched alkyl group having 1–18 carbon atoms capable of including one or non-neighboring two or more methylene groups which can be replaced with at least one species of —O—, —S—, —CO—, —COO—, —OCO— and —OCOO—;

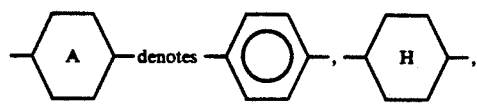
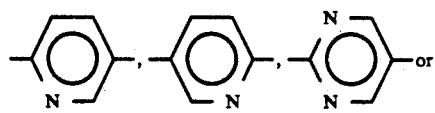
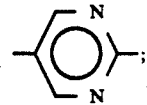
and n is 0 or 1.
201 Claims, 2 Drawing Sheets

MESOMORPHIC COMPOUND, LIQUID CRYSTAL COMPOSITION CONTAINING SAME AND LIQUID CRYSTAL DEVICE USING SAME

This application is a continuation of application Ser. No. 585,530 filed Sep. 20, 1990, now abandoned.

FIELD OF THE INVENTION AND RELATED ART

The present invention relates to a novel mesomorphic compound, a liquid crystal composition containing the compound and liquid crystal device using the composition, and more particularly to a novel liquid crystal composition with improved responsiveness to an electric field and a liquid crystal device using the liquid crystal composition for use in a liquid crystal display apparatus, a liquid crystal-optical shutter, etc.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected or regions where a scanning electrode is not selected and a signal electrode is selected (which regions are so called "half-selected points"). If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. As a result, this leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and are vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, it is the present state that the development of large image area or high packaging density with respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216, U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second optically stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric field and retaining the resultant state in the absence of an electric field.

In addition to the above-described characteristic of showing bistability, such a ferroelectric liquid crystal has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, ferroelectric liquid crystal materials developed heretofore cannot be said to satisfy sufficient characteristics required for a liquid crystal device including low-temperature operation characteristic, high-speed responsiveness, etc. Among a response time $\tau$, the magnitude of spontaneous polarization Ps and viscosity $\eta$, the following relationship exists: $\tau = \eta/(Ps \cdot E)$, where E is an applied voltage. Accordingly, a high response speed can be obtained by (a) increasing the spontaneous polarization Ps, (b) lowering the viscosity $\eta$, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Further, if it is assumed that the operation temperature of an actual display device is 5°–40° C., the response speed changes by a factor of about 20, so that it actually exceeds the range controllable by driving voltage and frequency.

As described hereinabove, commercialization of a ferroelectric liquid crystal device requires a ferroelectric chiral smectic liquid crystal composition having a low viscosity, a high-speed responsiveness and a small temperature-dependence of response speed.

SUMMARY OF THE INVENTION

An object of the present invention is to provide a novel mesomorphic compound, a liquid crystal composition with improved responsiveness containing the mesomorphic compound for providing a practical ferroelectric liquid crystal device, and a liquid crystal device using the liquid crystal composition.

Another object of the present invention is to provide a liquid crystal device using a liquid crystal composition containing a novel mesomorphic compound and showing improved display characteristics due to AC stabilization effect.

According to the present invention, there is provided a mesomorphic compound represented by the following formula (I):

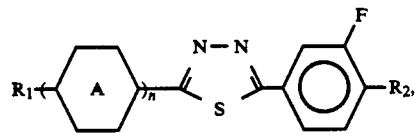

wherein $R_1$ and $R_2$ respectively denote a linear or branched alkyl group having 1–18 carbon atoms capable of including one or non-neighboring two or more methylene groups which can be replaced with at least one species of —O—, —S—, —CO—, —COO—, —OCO— and —OCOO—;

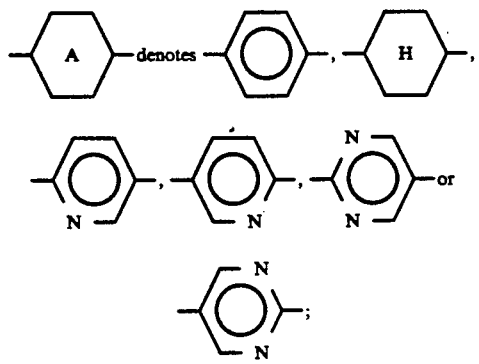

and n is 0 or 1.

According to the present invention, there is further provided a liquid crystal composition containing at least one species of the mesomorphic compound as described above.

The present invention further provides a liquid crystal device comprising a pair of substrates and such a liquid crystal composition as described above disposed between the electrode plates.

Heretofore, thiadiazole derivatives or electro-optical display devices using compositions comprising the thiadiazole derivatives have been disclosed in WO 88/08019 and Japanese Laid-Open Patent Applications (KOKAI) Nos. 222148/1988 and 61472/1989. WO 88/08019 and the Japanese Laid-Open Patent Applications described above respectively disclose a broad general formula which can encompass a fluorophenylthiadiazole derivative wherein a fluorine atom is laterally disposed. However, there is no disclosure of a specific embodiment corresponding to the above compound having a laterally substituted fluorine atom in the above Japanese Laid-Open Patent Applications. In WO 88/08019, only one compound represented by the following formula:

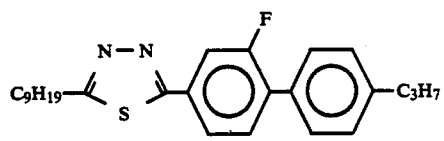

is disclosed as a specific embodiment corresponding to the above compound having a laterally substituted fluorine atom.

We have found that 4-substituted-3-fluorophenylthiadiazole derivative having three rings wherein a 3-fluorophenyl group having a laterally substituted fluorine atom is disposed at a terminal of the ring structure and a thiadiazole ring is disposed in the center of the ring structure, or having two rings can have a lowered clear point (transition temperature to an isotropic liquid) because a fluorine atom is laterally disposed. Particularly, the above compound having three rings can be used as a mesomorphic compound having a wide temperature range of a mesomorphic phase (particularly a smectic C (SmC) phase) because a thiadiazole ring is disposed in the center of the ring structure. We have also found that a liquid crystal device using a ferroelectric chiral smectic liquid crystal composition containing at least one species of the above-mentioned compound of the invention shows improved characteristics such as a good alignment characteristic, high-speed responsiveness and a decreased temperature-dependence of response speed to provide good display characteristics.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
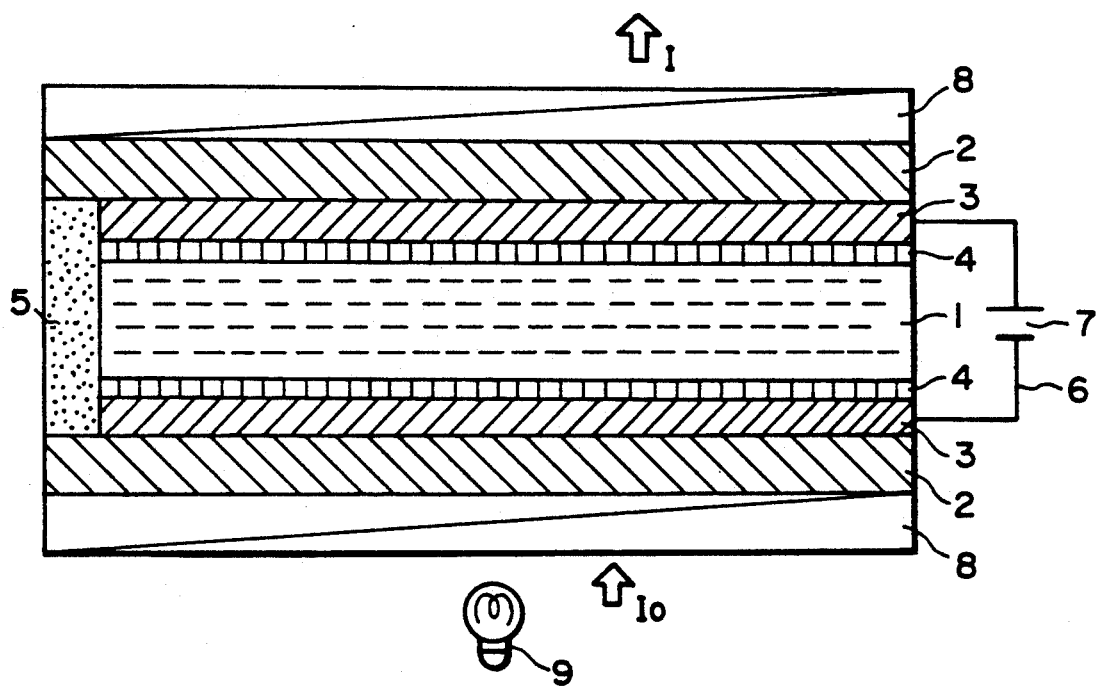
FIG. 1 is a schematic sectional view of a liquid crystal display device using a ferroelectric liquid crystal.

In the formula (I) as described above, preferred examples of $R_1$ and $R_2$ may include the following combinations (i) to (vi):

(i) $R_1$ is $n\text{—}C_mH_{2m+1}\text{—}X_1\text{—}$ and $R_2$ is $n\text{—}C_lH_{2l+1}\text{—}X_2\text{—}$;

(ii) $R_1$ is $n\text{—}C_mH_{2m+1}\text{—}X_1\text{—}$ and $R_2$ is

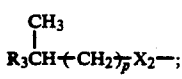

(iii) $R_1$ is $n\text{—}C_mH_{2m+1}\text{—}X_1\text{—}$ and $R_2$ is

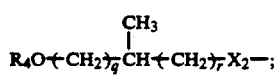

(iv) $R_1$ is

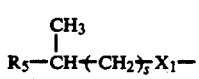

and $R_2$ is $n\text{—}C_mH_{2m+1}\text{—}X_2\text{—}$;

(v) $R_1$ is

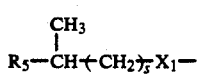

and $R_2$ is

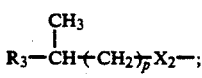

and
(vi) $R_1$ is

and $R_2$ is

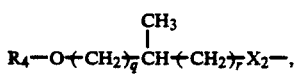

wherein m and l respectively denote an integer of 1-17; p, r and s respectively denote an integer of 0-7; q is 0 or 1; $R_3$, $R_4$ and $R_5$ respectively denote a linear or branched alkyl group; and $X_1$ and $X_2$ respectively denote a single bond, —O—,

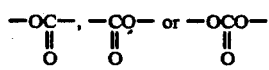

with the proviso that $X_1$ denotes a single bond when n is 0.

Further, in the formula (I) as described above,

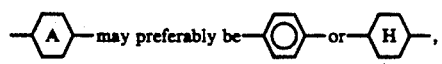

The compounds represented by the general formula (I) may be synthesized through the following reaction schemes.

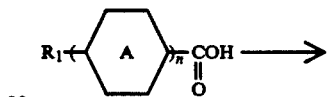

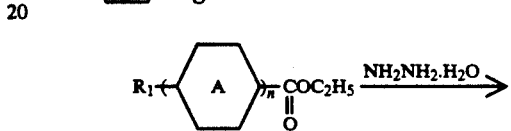

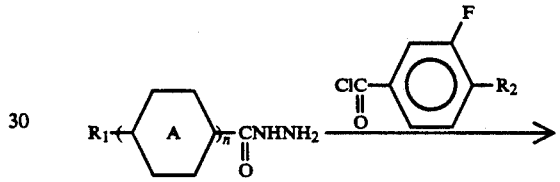

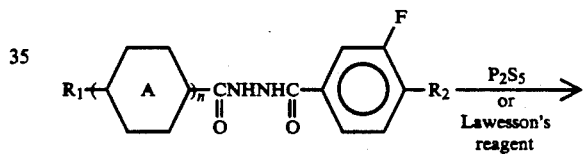

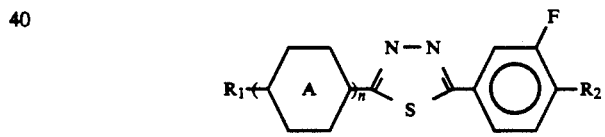

In the above, $R_1$, $R_2$,

and n are the same as defined above.

Specific examples of the mesomorphic compounds represented by the above-mentioned general formula (I) may include those shown by the following structural formulas.

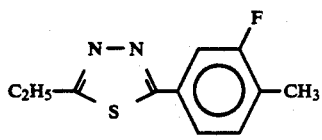
(I-1)

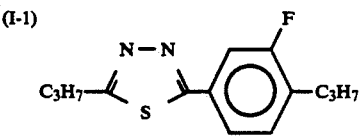
(I-2)

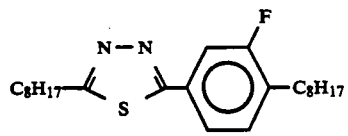 (I-3)
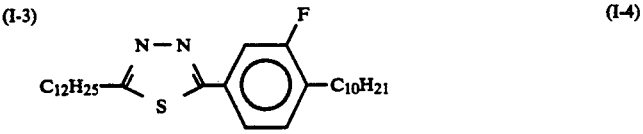 (I-4)
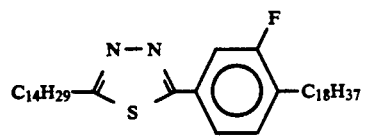 (I-5)
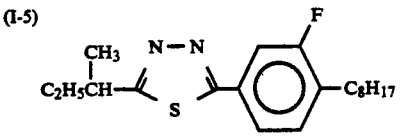 (I-6)
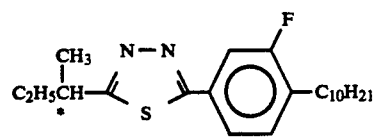 (I-7)
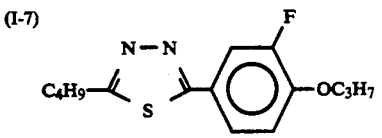 (I-8)
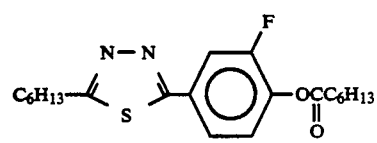 (I-9)
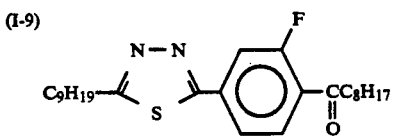 (I-10)
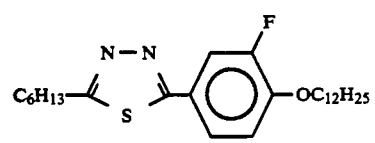 (I-11)
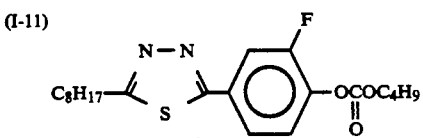 (I-12)
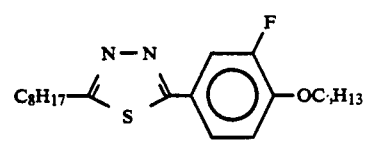 (I-13)
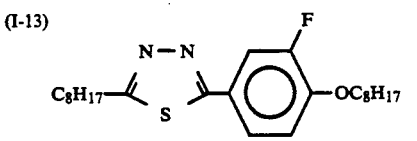 (I-14)
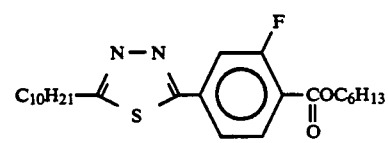 (I-15)
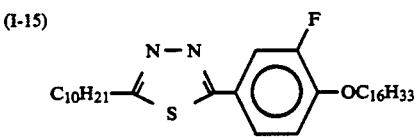 (I-16)
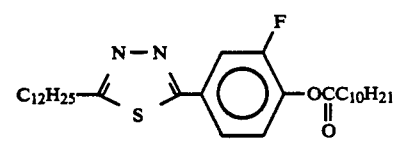 (I-17)
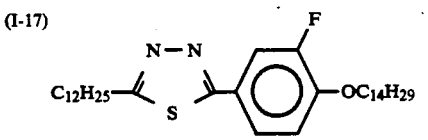 (I-18)
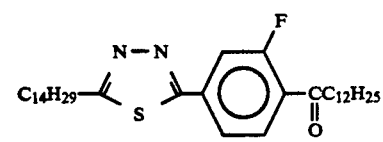 (I-19)
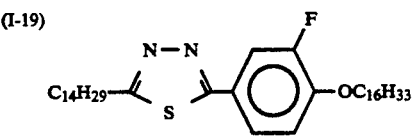 (I-20)
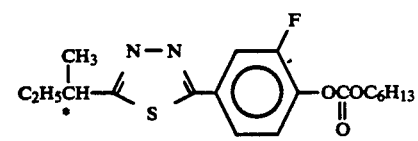 (I-21)
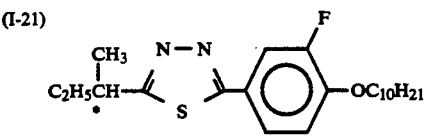 (I-22)
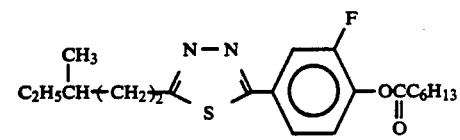 (I-23)
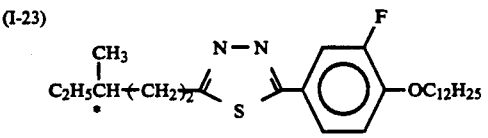 (I-24)

-continued
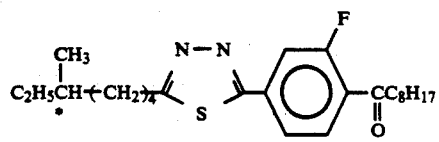 (I-25)
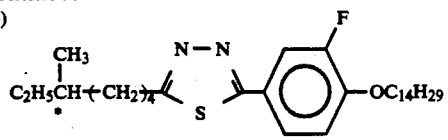 (I-26)
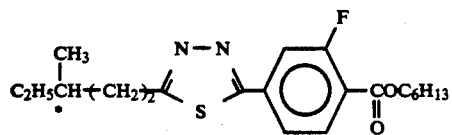 (I-27)
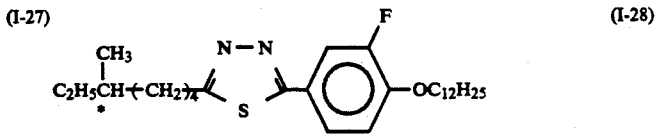 (I-28)
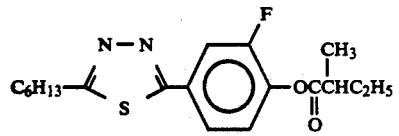 (I-29)
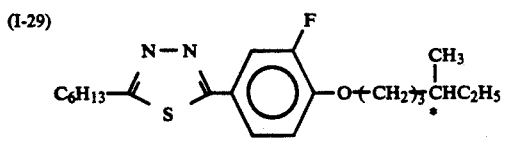 (I-30)
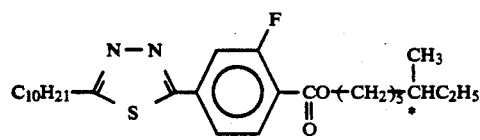 (I-31)
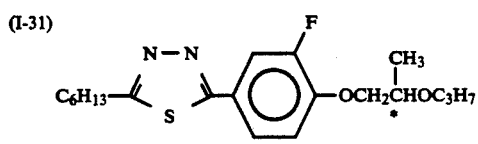 (I-32)
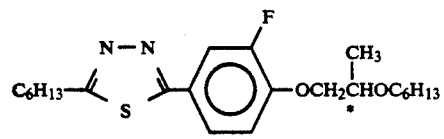 (I-33)
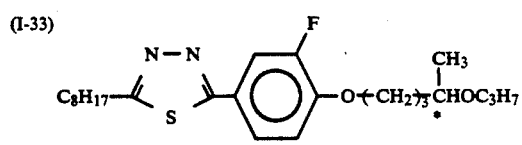 (I-34)
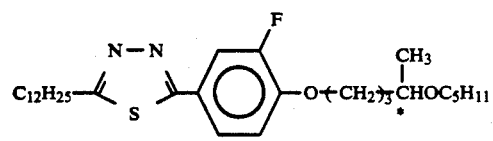 (I-35)
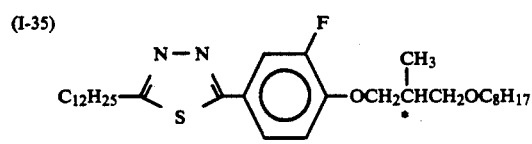 (I-36)
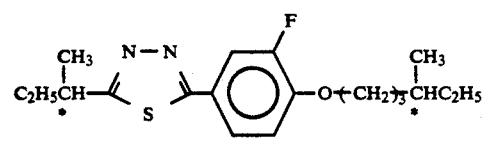 (I-37)
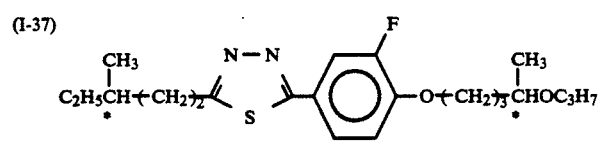 (I-38)
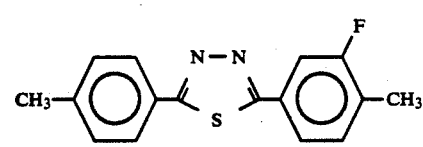 (I-39)
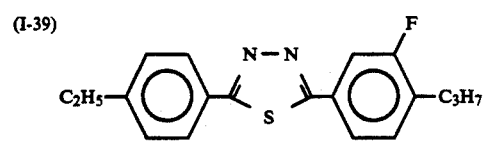 (I-40)
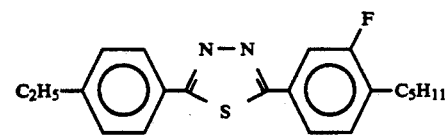 (I-41)
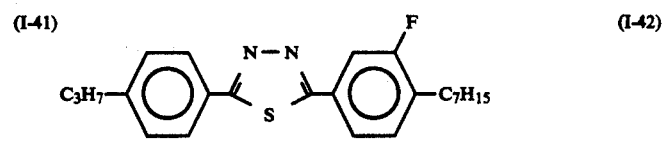 (I-42)
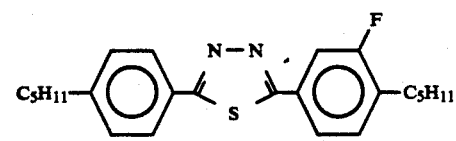 (I-43)
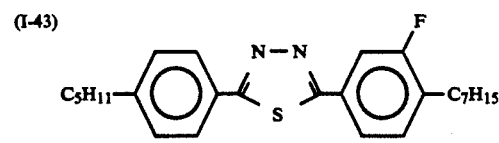 (I-44)
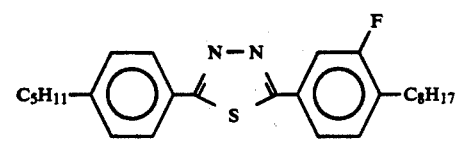 (I-45)
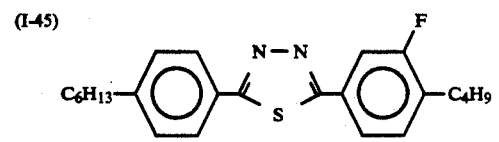 (I-46)

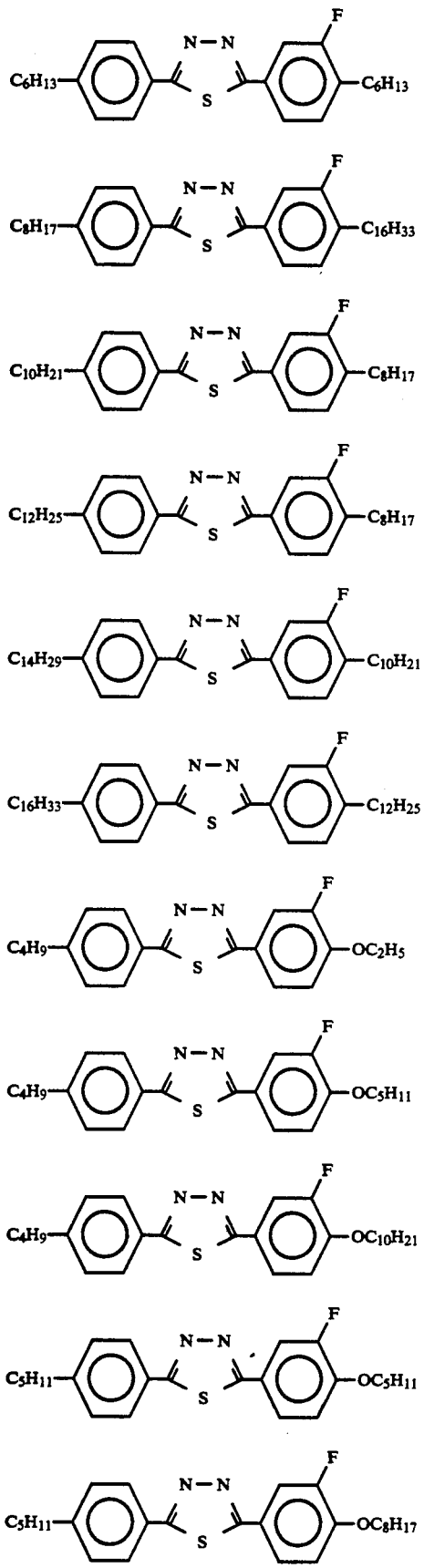

-continued
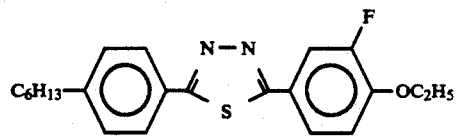 (I-69)
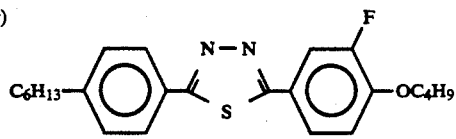 (I-70)
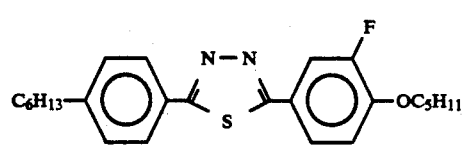 (I-71)
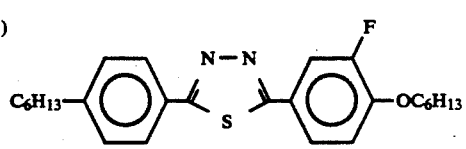 (I-72)
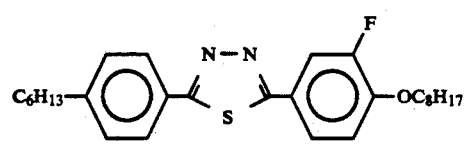 (I-73)
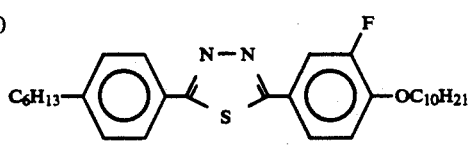 (I-74)
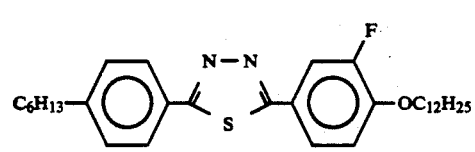 (I-75)
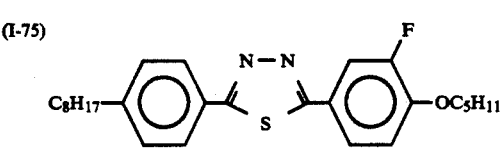 (I-76)
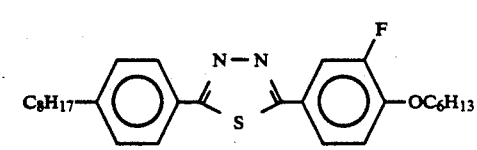 (I-77)
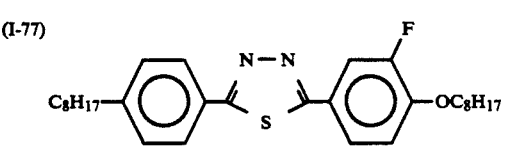 (I-78)
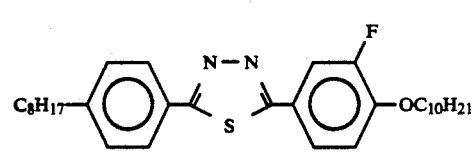 (I-79)
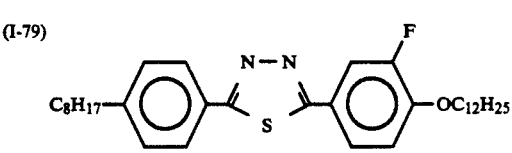 (I-80)
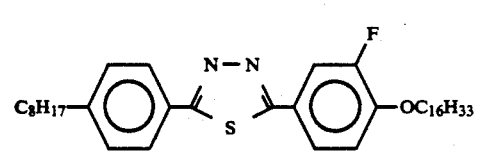 (I-81)
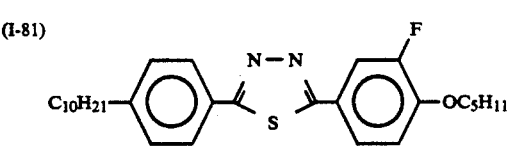 (I-82)
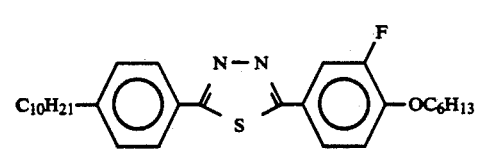 (I-83)
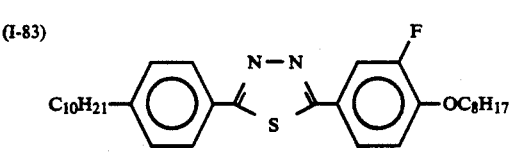 (I-84)
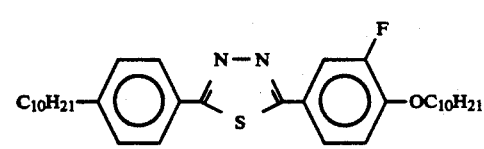 (I-85)
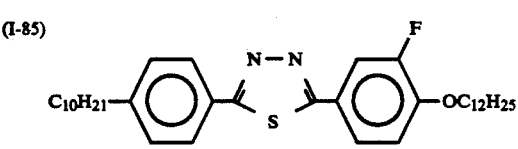 (I-86)
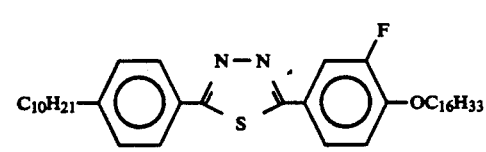 (I-87)
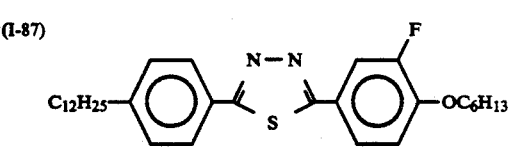 (I-88)
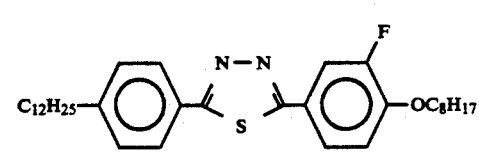 (I-89)
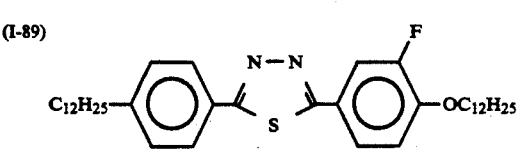 (I-90)

-continued
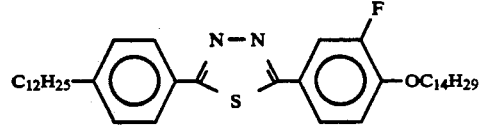 (I-91)
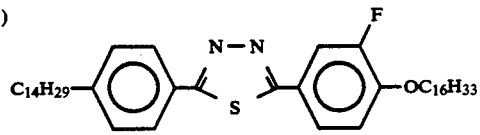 (I-92)
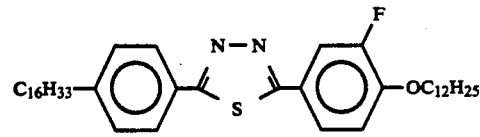 (I-93)
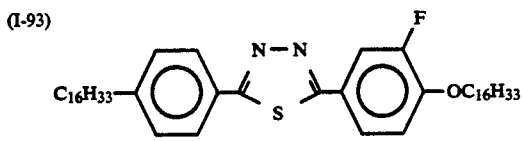 (I-94)
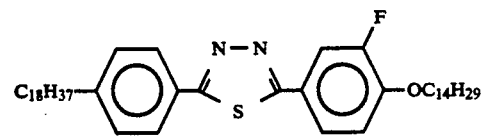 (I-95)
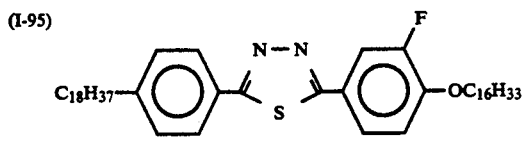 (I-96)
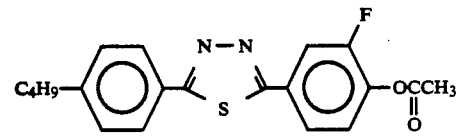 (I-97)
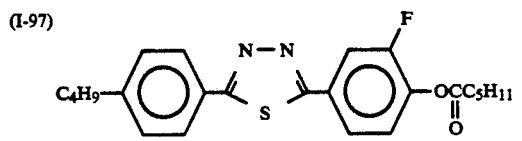 (I-98)
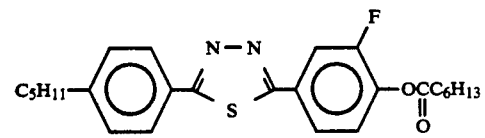 (I-99)
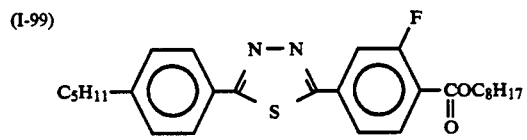 (I-100)
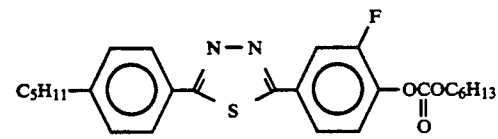 (I-101)
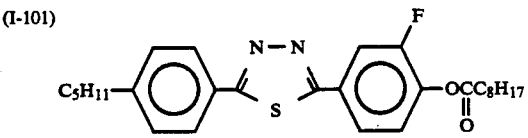 (I-102)
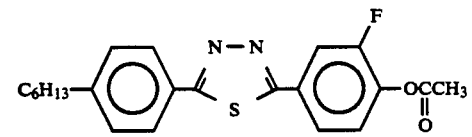 (I-103)
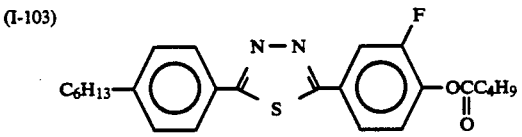 (I-104)
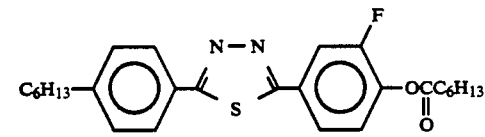 (I-105)
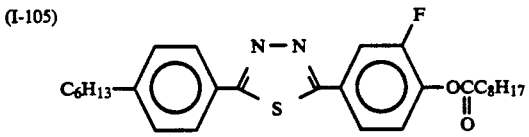 (I-106)
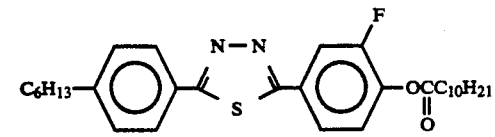 (I-107)
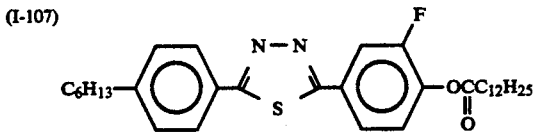 (I-108)
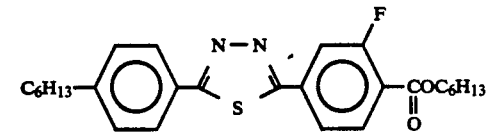 (I-109)
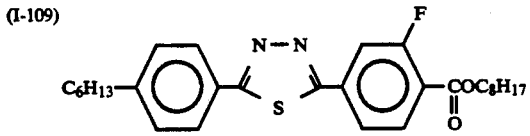 (I-110)
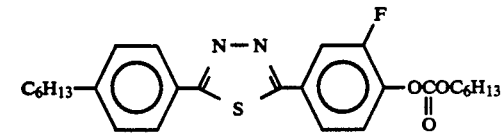 (I-111)
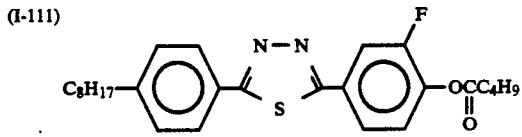 (I-112)

-continued (I-113) through (I-134): chemical structures of 1,3,4-thiadiazole compounds with various substituents.

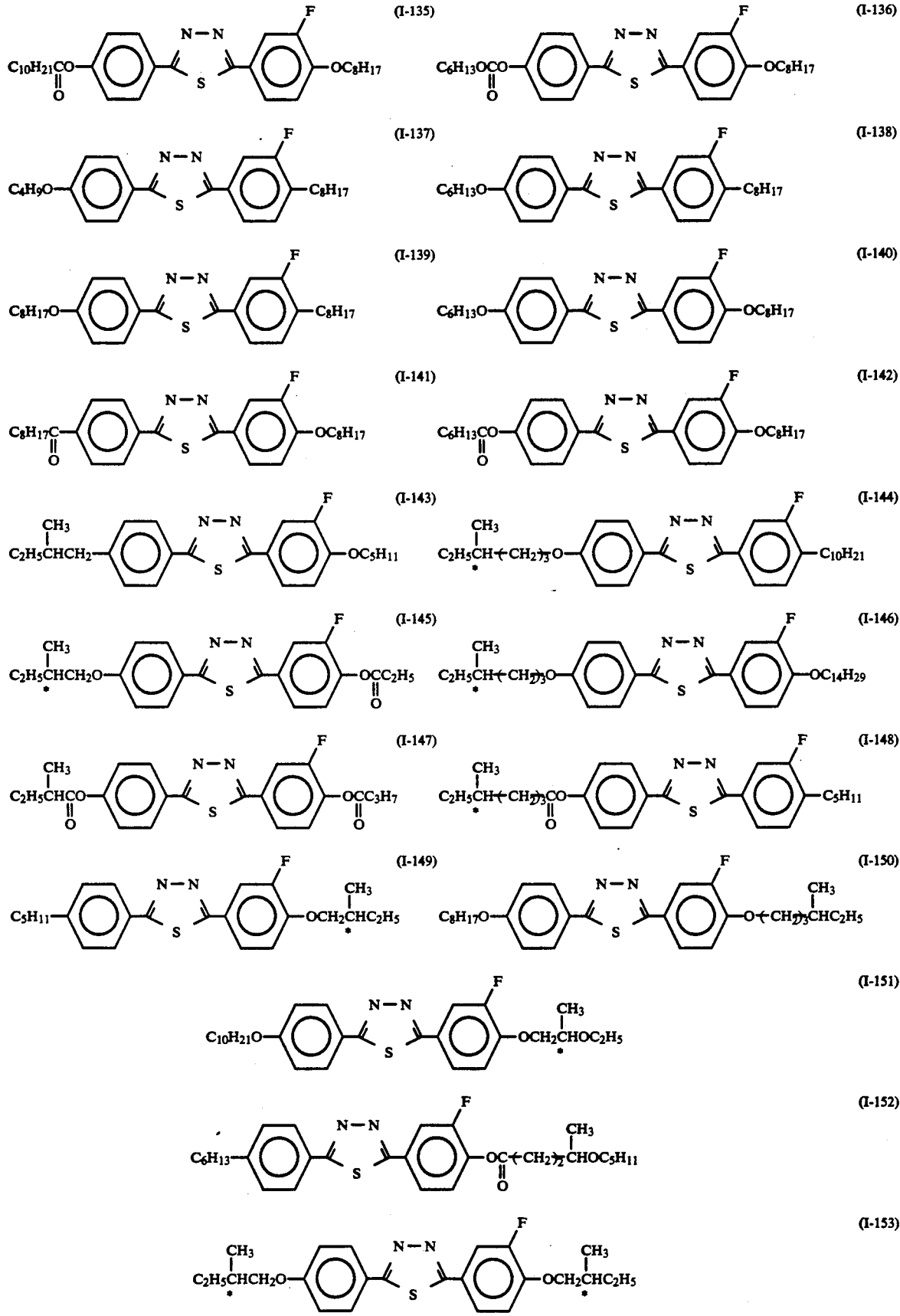

(Chemical structure diagrams I-154 through I-173)

-continued
(I-174) 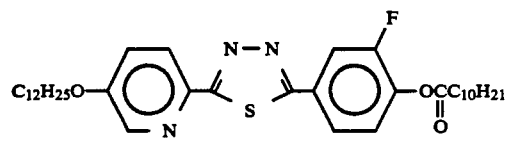
(I-175) 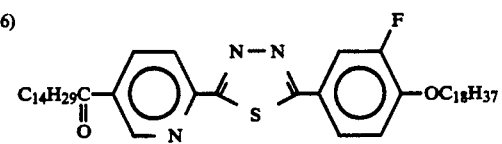
(I-176) 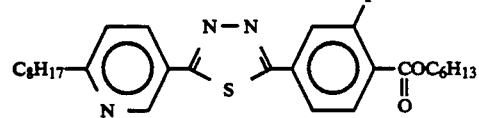
(I-177) 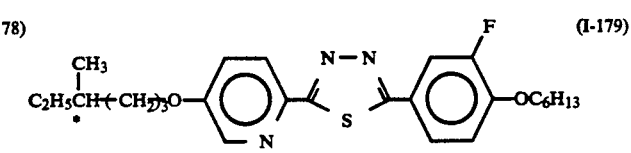
(I-178) 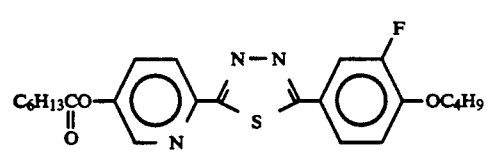
(I-179) 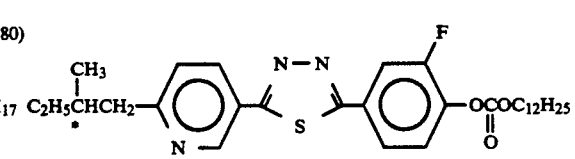
(I-180) 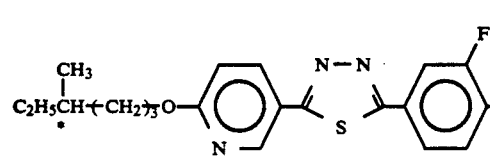
(I-181) 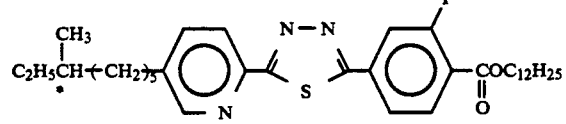
(I-182) 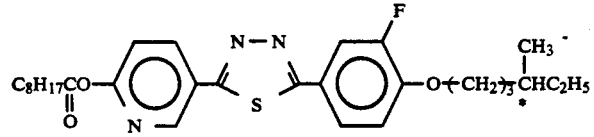
(I-183) 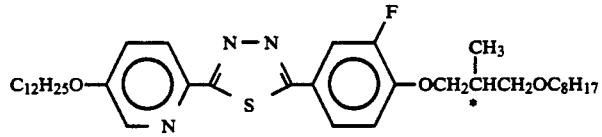
(I-184) 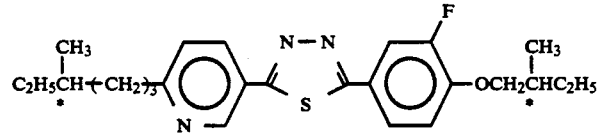
(I-185) 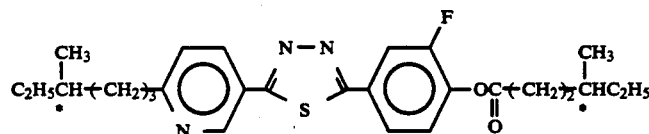
(I-186) 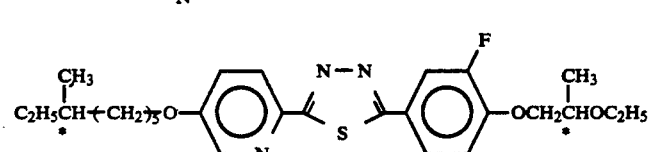
(I-187) 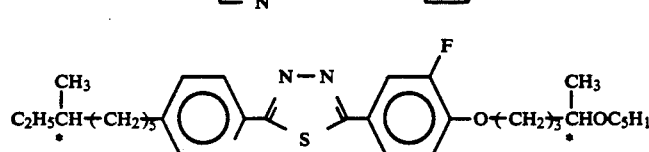
(I-188)

Chemical structure diagrams (I-189) through (I-208).

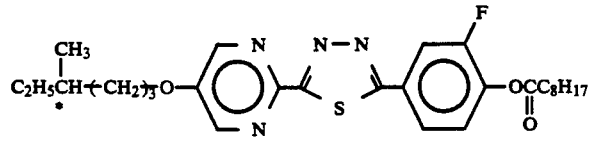 (I-209)
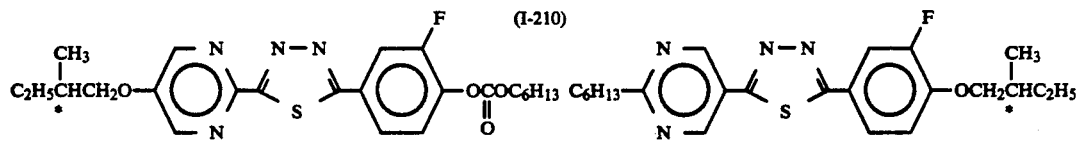
(I-210) (I-211)
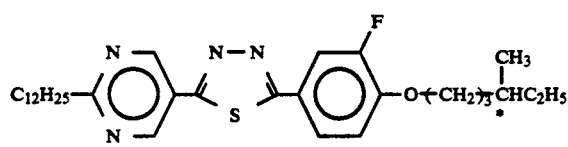 (I-212)
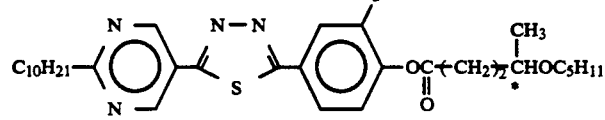 (I-213)
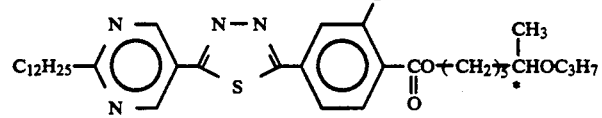 (I-214)
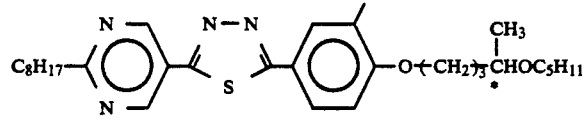 (I-215)
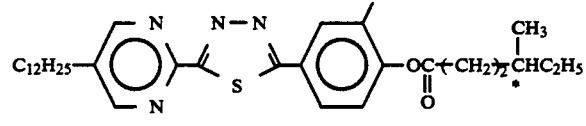 (I-216)
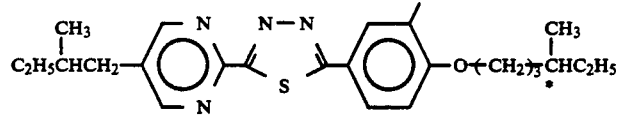 (I-217)
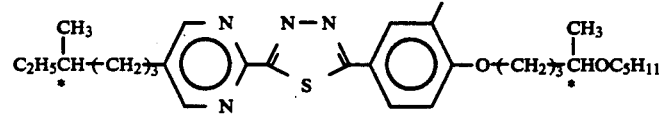 (I-218)
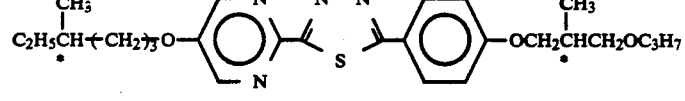 (I-219)
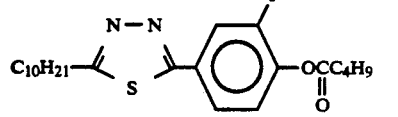 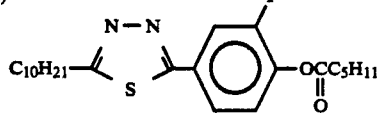
(I-220) (I-221)

The liquid crystal composition according to the present invention may be obtained by mixing at least one species of the compound represented by the formula (I) and at least one species of another ferroelectric or non-ferroelectric mesomorphic compound so that the resultant composition contains 1–85 wt. %, preferably 1–40 wt. % of the compound(s) represented by the formula (I). The liquid crystal composition according to the present invention may preferably be formulated as a ferroelectric liquid crystal composition, particularly a ferroelectric chiral smectic liquid crystal composition.

Specific examples of another mesomorphic compound as described above may include those denoted by the following structural formulas.

-continued $$C_8H_{17}O-\phenyl-O-\overset{O}{\underset{\|}{C}}-\phenyl-\phenyl-CH_2\overset{CH_3}{\underset{*}{CH}}C_2H_5 \quad (8)$$

$$C_8H_{17}O-\phenyl-\overset{CS}{\underset{\|}{\underset{O}{}}}-\phenyl-CH_2\overset{CH_3}{\underset{*}{CH}}C_2H_5 \quad (9)$$

$$C_{13}H_{27}-\phenyl-\phenyl-\overset{CS}{\underset{\|}{\underset{O}{}}}-\phenyl-CH_2\overset{CH_3}{\underset{*}{CH}}C_2H_5 \quad (10)$$

$$C_{10}H_{21}O-\phenyl-\overset{CS}{\underset{\|}{\underset{O}{}}}-\phenyl-OCH_2\overset{CH_3}{\underset{*}{CH}}C_2H_5 \quad (11)$$

$$C_7H_{15}O-\phenyl-\phenyl-\overset{O}{\underset{\|}{C}}-O-\phenyl-O\overset{O}{\underset{\|}{C}}CH_2\overset{CH_3}{\underset{*}{CH}}C_2H_5 \quad (12)$$

$$C_{10}H_{21}O-\text{pyrimidine}-\phenyl-O(CH_2)_3\overset{CH_3}{\underset{*}{CH}}C_2H_5 \quad (13)$$

$$C_6H_{13}O-\phenyl-\phenyl-\overset{O}{\underset{\|}{C}}-O-\phenyl(F)-OCH_2\overset{CH_3}{\underset{*}{CH}}C_2H_5 \quad (14)$$

$$C_8H_{17}O-\phenyl-\text{pyrazine}-\overset{O}{\underset{\|}{C}}-O-\phenyl-OCH_2\overset{CH_3}{\underset{*}{CH}}C_2H_5 \quad (15)$$

$$C_{12}H_{25}-\phenyl-\text{pyrazine}-\overset{O}{\underset{\|}{C}}-O-\phenyl-O\overset{O}{\underset{\|}{C}}CH_2\overset{CH_3}{\underset{*}{CH}}C_2H_5 \quad (16)$$

$$C_{12}H_{25}O-\phenyl-\text{pyrazine}-\overset{O}{\underset{\|}{C}}-O(CH_2)_3\overset{CH_3}{\underset{*}{CH}}C_2H_5 \quad (17)$$

$$C_8H_{17}O-\phenyl-\overset{O}{\underset{\|}{C}}-O-\phenyl-OCH_2\overset{CH_3}{\underset{*}{CH}}C_2H_5 \quad (18)$$

$$C_{12}H_{25}O-\phenyl-\overset{CS}{\underset{\|}{\underset{O}{}}}-\phenyl-CH_2\overset{CH_3}{\underset{*}{CH}}C_2H_5 \quad (19)$$

$$C_{10}H_{21}O-\text{pyrimidine}-\phenyl-O(CH_2)_3\overset{CH_3}{\underset{*}{CH}}C_2H_5 \quad (20)$$

$$C_8H_{17}-\text{pyrazine}-\phenyl-O(CH_2)_3\overset{CH_3}{\underset{*}{CH}}C_2H_5 \quad (21)$$

$$C_7H_{15}O-\phenyl-\overset{O}{\underset{\|}{C}}-O-\phenyl-O(CH_2)_3\overset{CH_3}{\underset{*}{CH}}C_3H_7 \quad (22)$$

$$C_8H_{17}-\text{pyrazine}-\phenyl-O(CH_2)_3\overset{CH_3}{\underset{*}{CH}}C_2H_5 \quad (23)$$

$$C_{11}H_{23}O-\text{pyrimidine}-\phenyl-O(CH_2)_2\overset{CH_3}{\underset{*}{CH}}C_2H_5 \quad (24)$$

-continued
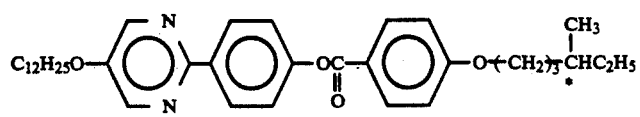 (25)
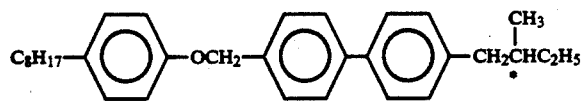 (26)
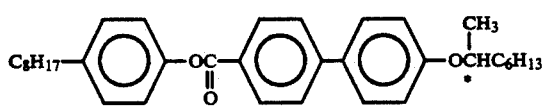 (27)
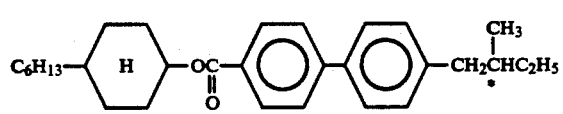 (28)
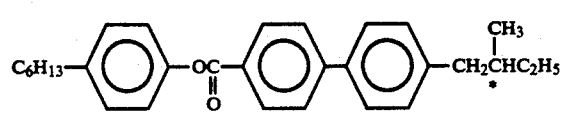 (29)
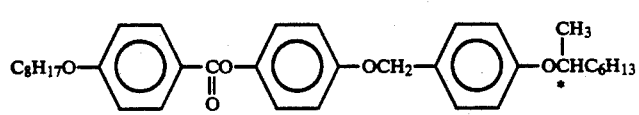 (30)
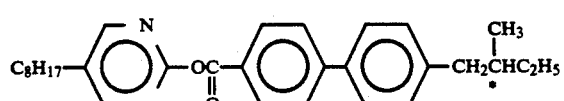 (31)
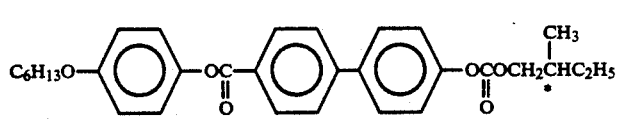 (32)
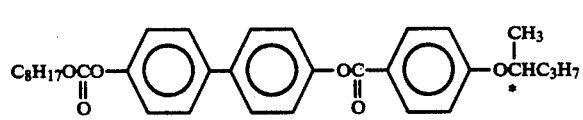 (33)
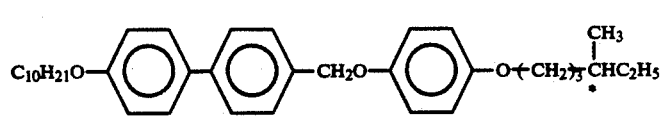 (34)
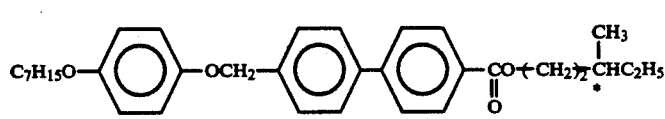 (35)
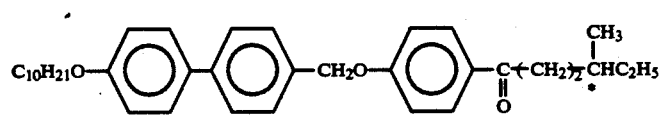 (36)
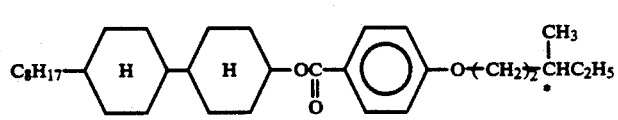 (37)

-continued
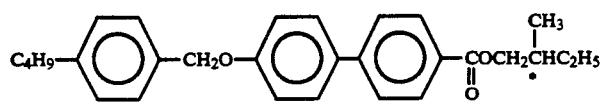 (38)
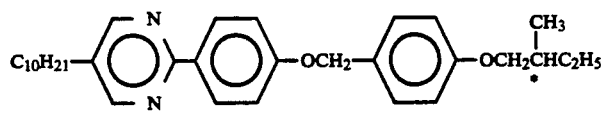 (39)
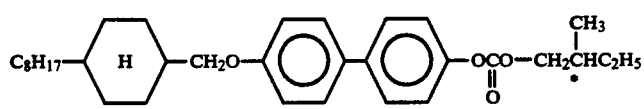 (40)
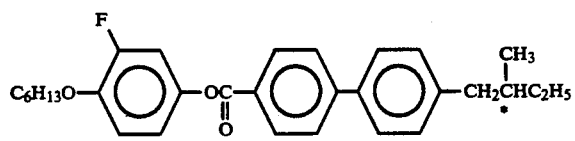 (41)
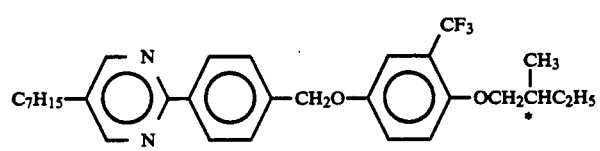 (42)
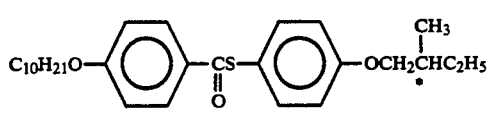 (43)
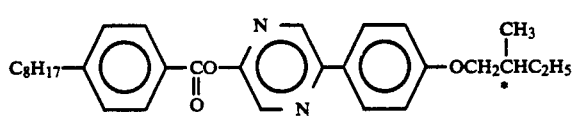 (44)
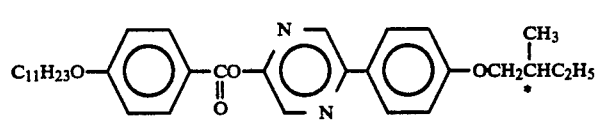 (45)
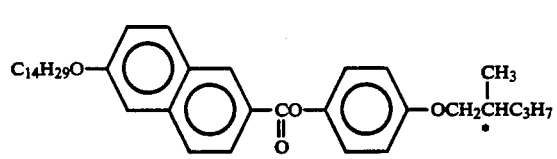 (46)
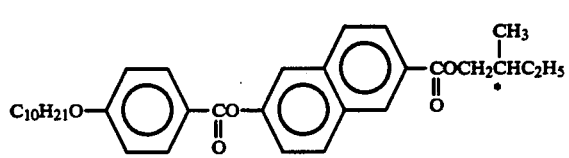 (47)
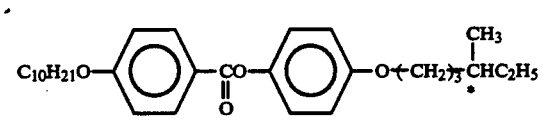 (48)
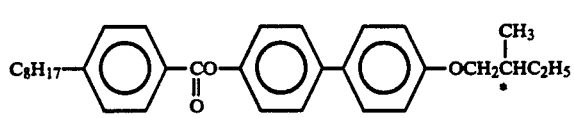 (49)

-continued
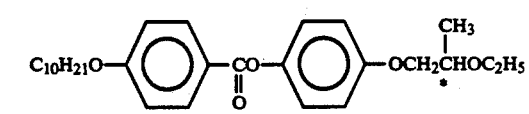 (50)
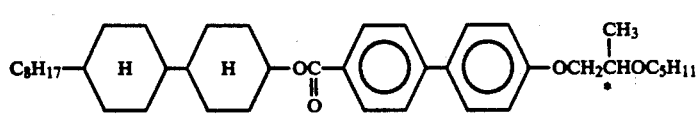 (51)
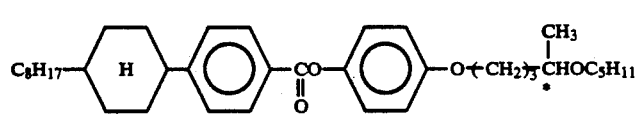 (52)
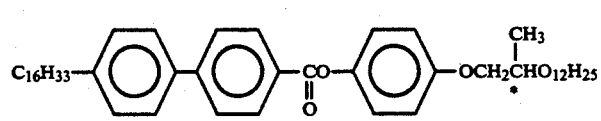 (53)
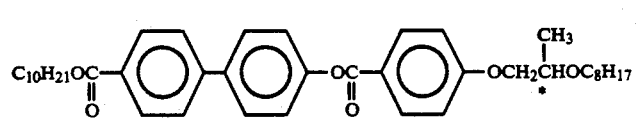 (54)
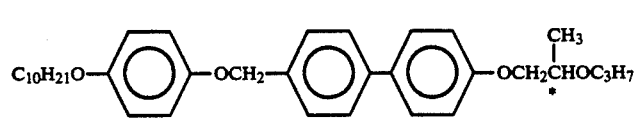 (55)
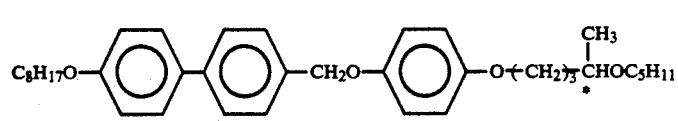 (56)
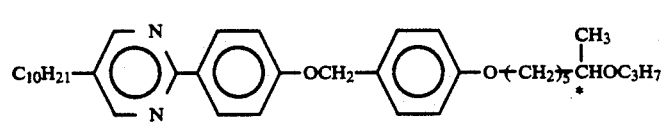 (57)
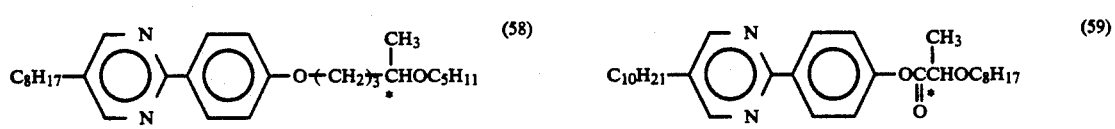 (58) (59)
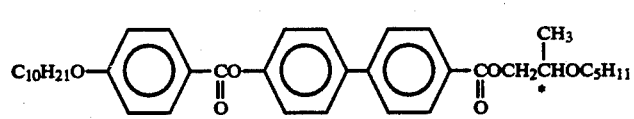 (60)
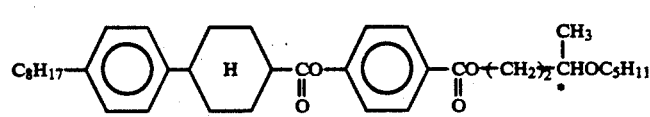 (61)
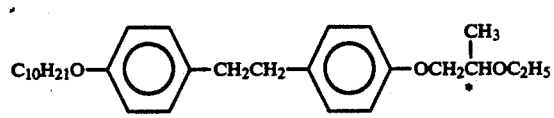 (62)
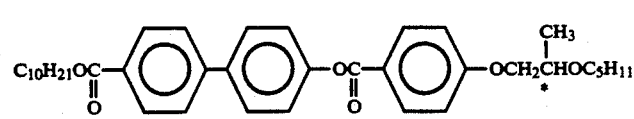 (63)

-continued
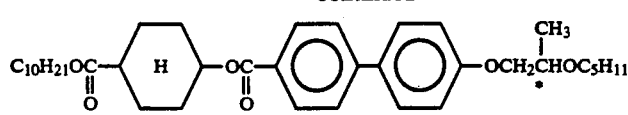
(64)
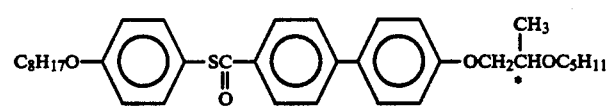
(65)
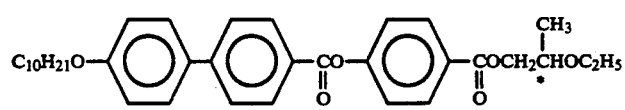
(66)
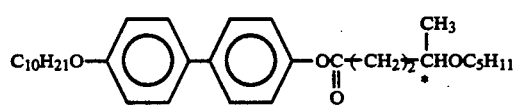
(67)
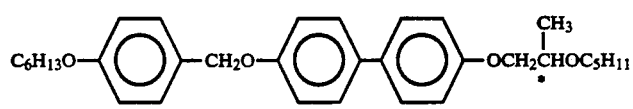
(68)
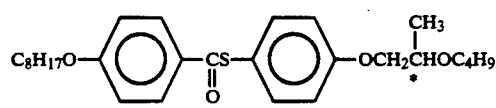
(69)
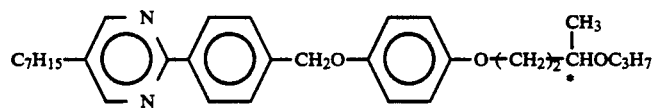
(70)
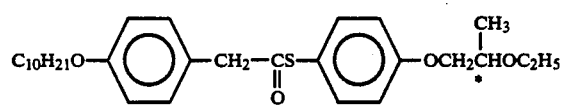
(71)
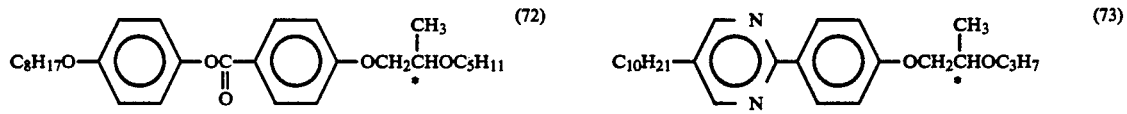
(72)     (73)
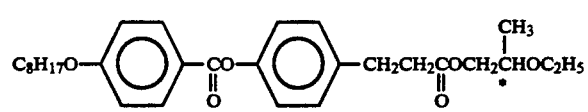
(74)
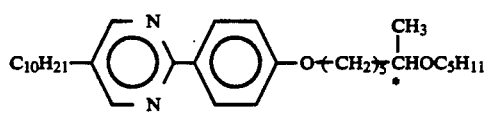
(75)
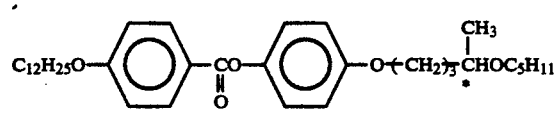
(76)
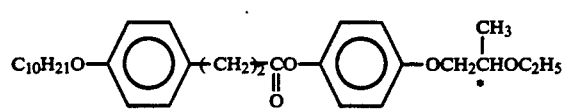
(77)

-continued
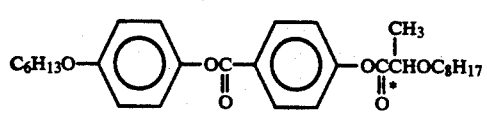 (78)
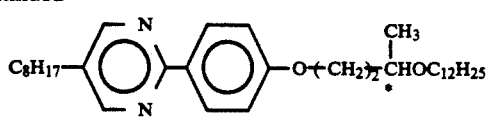 (79)
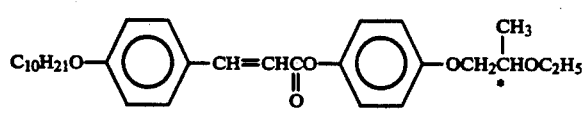 (80)
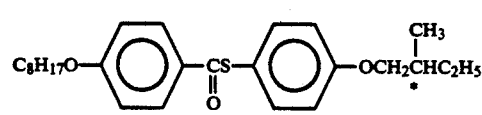 (81)
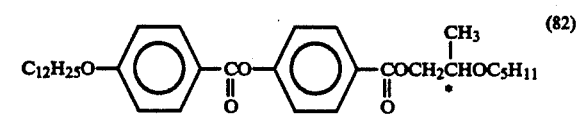 (82)
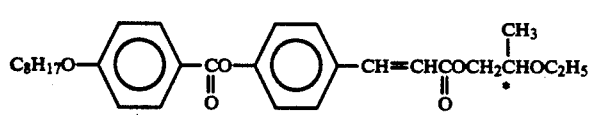 (83)
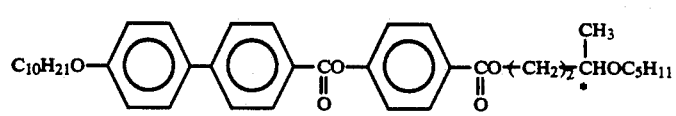 (84)
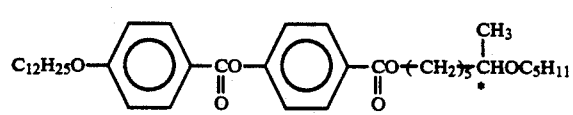 (85)
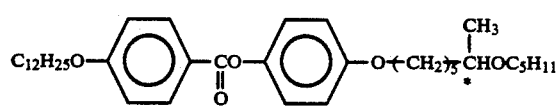 (86)
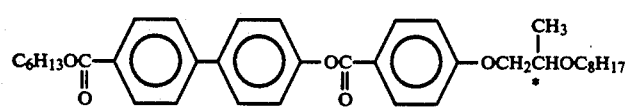 (87)
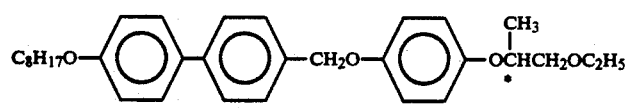 (88)
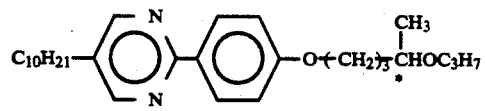 (89)
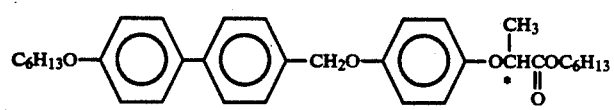 (90)
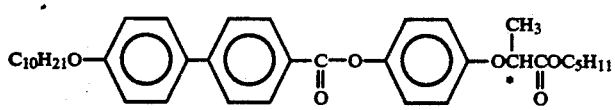 (91)
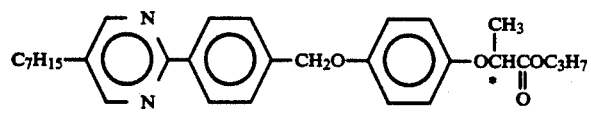 (92)

-continued $$C_6H_{13}O-\underset{N}{\underset{\|}{\bigcirc}}-\bigcirc-OCH_2-\bigcirc-O\overset{CH_3}{\underset{*}{C}H}\underset{\|}{C}OC_6H_{13} \quad (93)$$

$$C_{10}H_{21}O-\bigcirc-\bigcirc-CH_2O-\bigcirc-O\overset{CH_3}{\underset{*}{C}H}\underset{\|}{C}OC_6H_{13} \quad (94)$$

$$C_8H_{17}O-\bigcirc-O\underset{\|}{C}-\bigcirc-\bigcirc-O\overset{CH_3}{\underset{*}{C}H}\underset{\|}{C}OC_8H_{17} \quad (95)$$

$$C_6H_{13}O-\bigcirc-O\underset{\|}{C}-\bigcirc-\underset{F}{\bigcirc}-OCH_2\overset{CH_3}{\underset{*}{C}H}\underset{\|}{C}OC_4H_9 \quad (96)$$

$$C_8H_{17}O-\bigcirc-\bigcirc-OCH_2-\bigcirc-O\overset{CH_3}{\underset{*}{C}H}\underset{\|}{C}OC_6H_{13} \quad (97)$$

$$C_8H_{17}O-\bigcirc-\bigcirc-O\underset{\|}{C}-\overset{Cl}{\underset{*}{C}H}C_3H_7 \quad (98)$$

$$C_8H_{17}O\underset{\|}{C}-\bigcirc-\bigcirc-\underset{\|}{C}-OCH_2\overset{Cl}{\underset{*}{C}H}(CH_3)_2 \quad (99)$$

$$C_{10}H_{21}O-\bigcirc-\bigcirc-\underset{\|}{C}-\bigcirc-O-CH_2\overset{Cl}{\underset{*}{C}H}C_2H_5 \quad (100)$$

$$C_{12}H_{25}O-\bigcirc-O\underset{\|}{C}-\bigcirc-OCH_2\overset{CH_3}{\underset{*}{C}H}CH(CH_3)_2 \quad (101)$$

$$C_5H_{11}\underset{\|}{C}-\bigcirc-\underset{\|}{C}-\bigcirc-\bigcirc-O(CH_2)_2\overset{Cl}{\underset{*}{C}H}C_2H_5 \quad (102)$$

$$C_7H_{15}-\bigcirc_H-\underset{N}{\underset{\|}{\bigcirc}}-\bigcirc-\underset{\|}{C}-\bigcirc-OCH_2\overset{Cl}{\underset{*}{C}H}CH_3 \quad (103)$$

$$C_{10}H_{21}-\underset{N}{\underset{\|}{\bigcirc}}-\bigcirc-O\underset{\|}{C}-\bigcirc-O(CH_2)_2\overset{Cl}{\underset{*}{C}H}C_2H_5 \quad (104)$$

$$C_8H_{17}O\underset{\|}{C}-\bigcirc-\bigcirc-\underset{\|}{CS}-\bigcirc-O(CH_2)_2\overset{Cl}{\underset{*}{C}H}C_2H_5 \quad (105)$$

$$C_{10}H_{21}-\bigcirc-\underset{\|}{S}\underset{O}{C}-\bigcirc-OCH_2\overset{Cl}{\underset{*}{C}H}C_3H_7 \quad (106)$$

-continued
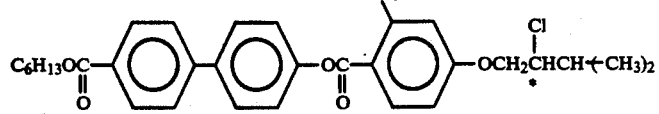 (107)
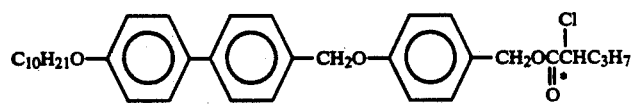 (108)
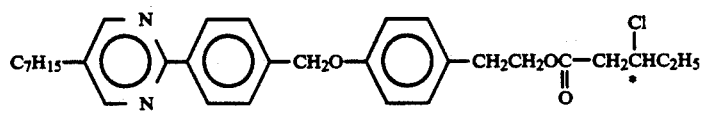 (109)
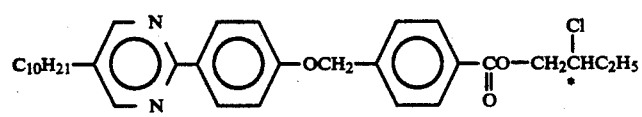 (110)
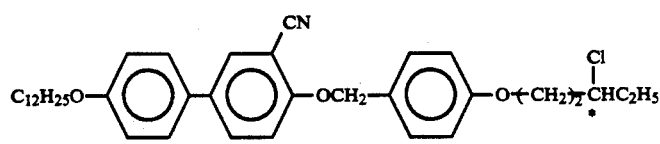 (111)
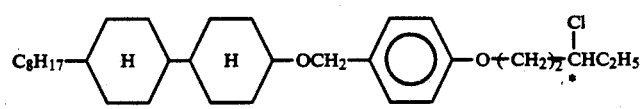 (112)
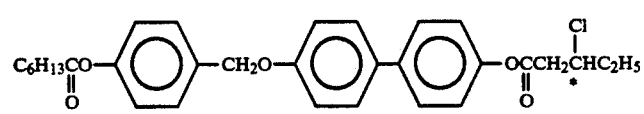 (113)
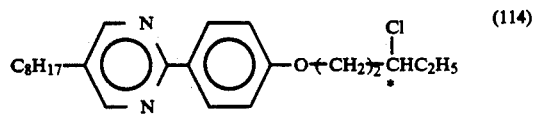 (114)
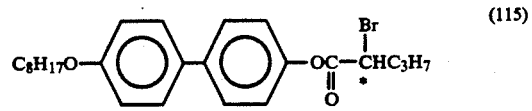 (115)
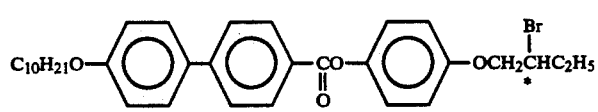 (116)
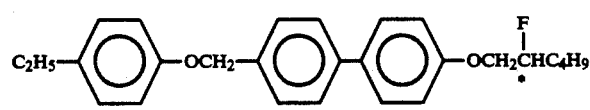 (117)
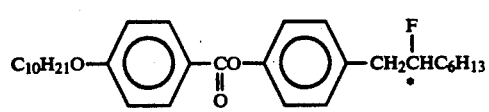 (118)
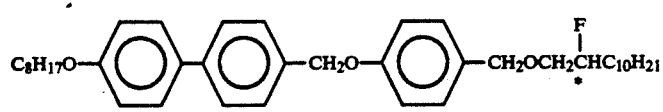 (119)
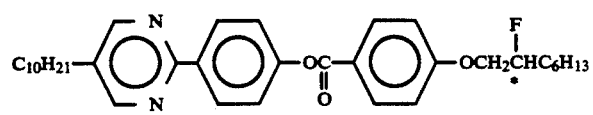 (120)

$$C_{10}H_{21}\text{-pyrazine-}C_6H_4\text{-OCH}_2\text{-}C_6H_4\text{-CH}_2CH_2COOCH_2\overset{*}{C}HFC_4H_9 \quad (121)$$

$$C_8H_{17}O\text{-}C_6H_4\text{-}C_6H_4\text{-COOCH}_2\overset{*}{C}HFC_6H_{13} \quad (122)$$

$$C_{10}H_{21}O\text{-}C_6H_4\text{-}C_6H_4\text{-COO-}C_6H_4\text{-OCH}_2\overset{*}{C}HFC_8H_{17} \quad (123)$$

$$C_{12}H_{25}O\text{-}C_6H_4\text{-COO-}C_6H_4\text{-OCH}_2\overset{*}{C}HFC_6H_{13} \quad (124)$$

$$C_7H_{15}\text{-Cy-pyrazine-}C_6H_4\text{-COOCH}_2\overset{*}{C}HFC_8H_{17} \quad (125)$$

$$C_7H_{15}\text{-pyrazine-}C_6H_4\text{-COO-}C_6H_4\text{-OCH}_2\overset{*}{C}HFC_5H_{11} \quad (126)$$

$$C_6H_{13}O\text{-}C_6H_4\text{-COO-}C_6H_4\text{-OCH}_2\overset{*}{C}HFC_8H_{17} \quad (127)$$

$$C_8H_{17}O\text{-}C_6H_4\text{-S(O)-}C_6H_4\text{-OCH}_2\overset{*}{C}HFC_6H_{13} \quad (128)$$

$$C_{10}H_{21}\text{-pyrazine-}C_6H_4\text{-OCH}_2\overset{*}{C}HFC_8H_{17} \quad (129)$$

$$C_5H_{11}\text{-Cy-COO-}C_6H_4\text{-OCH}_2\overset{*}{C}HFC_6H_{13} \quad (130)$$

$$C_8H_{17}O\text{-}C_6H_4\text{-COO-}C_6H_4\text{-OCH}_2\overset{*}{C}HFC_2H_5 \quad (131)$$

$$C_{12}H_{25}\text{-pyrazine-}C_6H_4\text{-OCH}_2\overset{*}{C}HFC_6H_{13} \quad (132)$$

$$C_8H_{17}O\text{-}C_6H_4\text{-CH=CHCOO-}C_6H_4\text{-COCH}_2\overset{*}{C}HFC_6H_{13} \quad (133)$$

$$C_{13}H_{27}O\text{-}C_6H_4\text{-COO-}C_6H_4\text{-COCH}_2\overset{*}{C}HFC_6H_{13} \quad (134)$$

$$H_5C_2\overset{CH_3}{C}H(CH_2)_3O\text{-}C_6H_4\text{-COO-}C_6H_4\text{-OCH}_2\overset{*}{C}HFC_6H_{13} \quad (135)$$

$$C_8H_{17}O\text{-}C_6H_4\text{-COO-}C_6H_4\text{-OCH}_2\overset{*}{C}HFC_5H_{11} \quad (136)$$

$$C_{10}H_{21}O\text{-}C_6H_4\text{-S(O)-}C_6H_4\text{-OCH}_2\overset{*}{C}HFC_8H_{17} \quad (137)$$

$$C_3H_7\overset{CH_3}{C}HCOO\text{-}C_6H_4\text{-}C_6H_4\text{-OCH}_2\overset{*}{C}HFC_8H_{17} \quad (138)$$

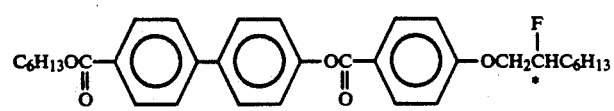
(139)
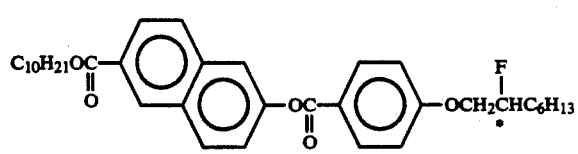
(140)
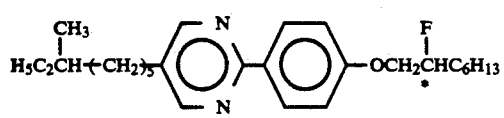
(141)
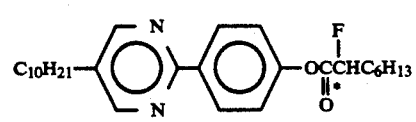
(142)
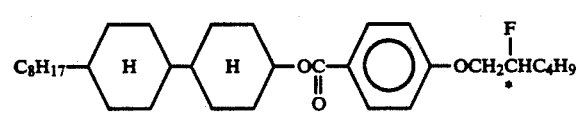
(143)
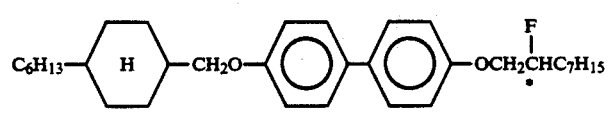
(144)
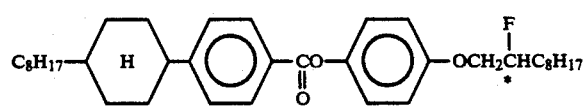
(145)
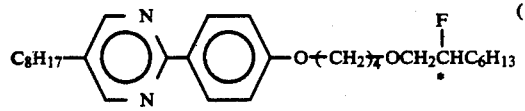
(146)
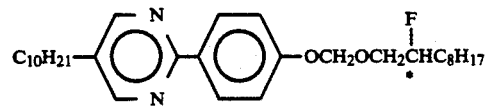
(147)
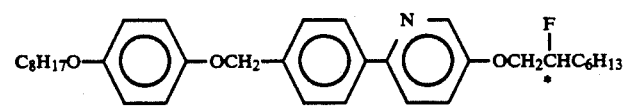
(148)
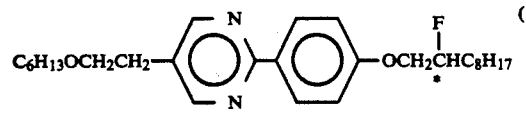
(149)
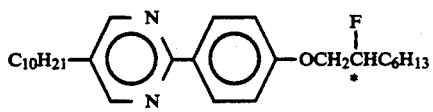
(150)
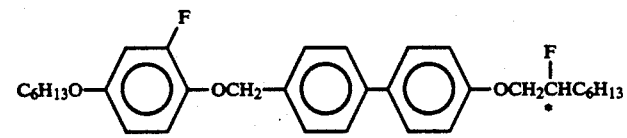
(151)
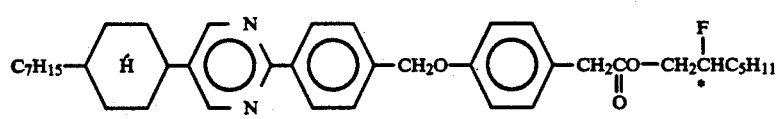
(152)
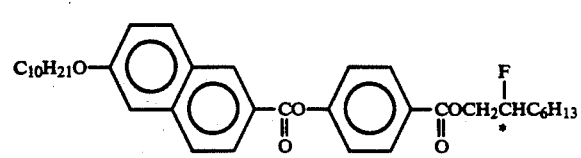
(153)

-continued
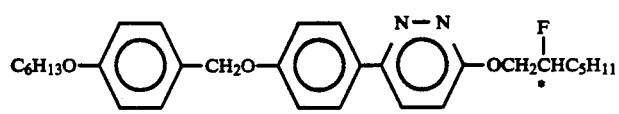 (154)
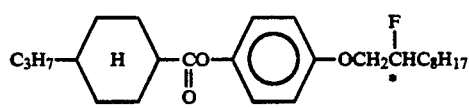 (155)
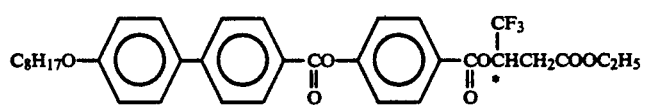 (156)
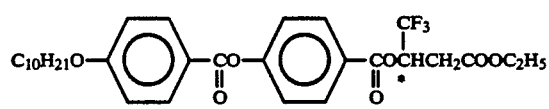 (157)
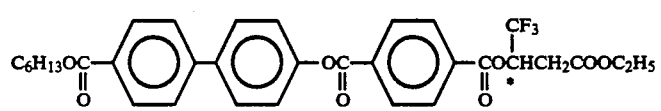 (158)
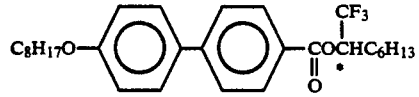 (159)
 (160)
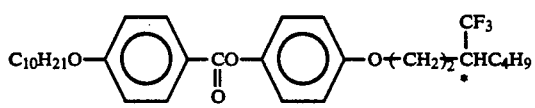 (161)
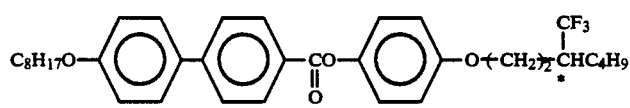 (162)
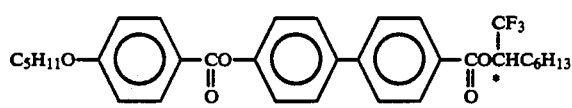 (163)
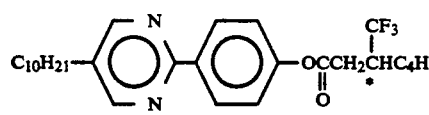 (164)
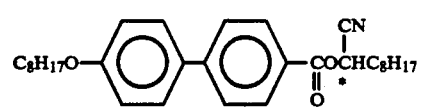 (165)
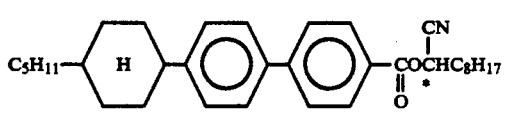 (166)
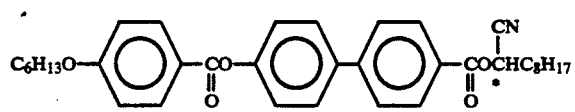 (167)
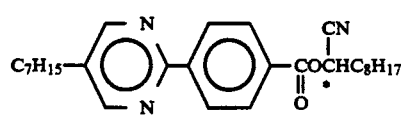 (168)
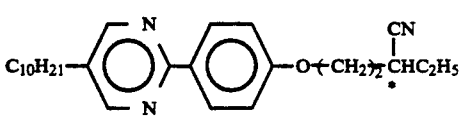 (169)

-continued (170) C₆H₁₃—[pyrimidine]—[phenyl]—OC₅H₁₁

(171) C₆H₁₃—[pyrimidine]—[phenyl]—OC₈H₇

(172) C₇H₁₅—[pyrimidine]—[phenyl]—OC₉H₁₉

(173) C₈H₁₇—[pyrimidine]—[phenyl]—OC₆H₁₃

(174) C₈H₁₇—[pyrimidine]—[phenyl]—OC₉H₁₉

(175) C₁₀H₂₁—[pyrimidine]—[phenyl]—OC₈H₁₇

(176) C₁₂H₂₅—[pyrimidine]—[phenyl]—OC₈H₁₇

(177) C₈H₁₇—[pyrimidine]—[phenyl]—OCOC₇H₁₅

(178) C₁₄H₂₉—[pyrimidine]—[phenyl]—OCOC₆H₁₃

(179) C₆H₁₃O—[pyrimidine]—[phenyl]—OC₈H₁₇

(180) C₈H₁₇O—[pyrimidine]—[phenyl]—OC₅H₁₁

(181) C₉H₁₉O—[pyrimidine]—[phenyl]—OC₁₀H₂₁

(182) C₁₁H₂₃O—[pyrimidine]—[phenyl]—OC₆H₁₃

(183) C₁₀H₂₁—[pyrimidine]—[phenyl]—C₈H₁₇

(184) C₁₂H₂₅—[pyrimidine]—[phenyl]—C₄H₉

(185) C₈H₁₇—[pyrimidine]—[phenyl]—O(CH₂)₃CH(CH₃)OC₃H₇

(186) C₁₀H₂₁—[pyrimidine]—[phenyl]—O(CH₂)₅CH(CH₃)OC₃H₇

(187) C₁₀H₂₁—[pyrimidine]—[phenyl]—O(CH₂)₇CH(CH₃)OCH₃

(188) C₁₂H₂₅—[pyrimidine]—[phenyl]—O(CH₂)₇CH(CH₃)OCH₃

(189) C₁₂H₂₅—[pyrimidine]—[phenyl]—OCOCH(CH₃)OC₅H₁₁

(190) C₁₀H₂₁—[pyrimidine]—[phenyl]—OCH(CH₃)CH₂OC₃H₇

(191) C₅H₁₁—[pyrimidine]—[phenyl]—[phenyl]—C₆H₁₃

(192) C₇H₁₅—[pyrimidine]—[phenyl]—[phenyl]—C₆H₁₃

(193) C₈H₁₇—[pyrimidine]—[phenyl]—[phenyl]—C₅H₁₁

(194) C₁₀H₂₁—[pyrimidine]—[phenyl]—[phenyl]—C₈H₁₇

(195) C₁₀H₂₁—[pyrimidine]—[phenyl]—[phenyl]—OC₅H₁₁

-continued
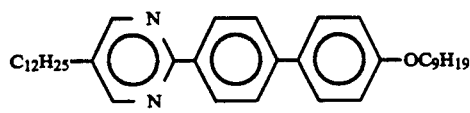 (196)
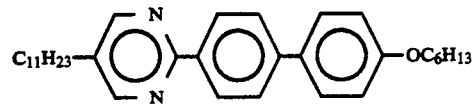 (197)
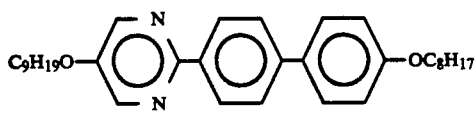 (198)
 (199)
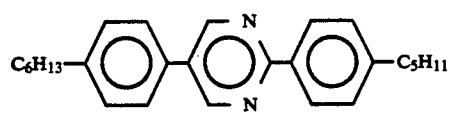 (200)
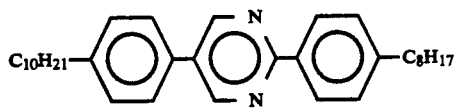 (201)
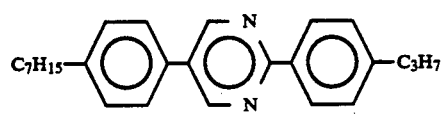 (202)
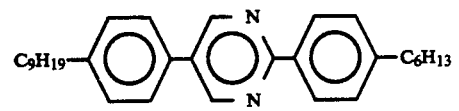 (203)
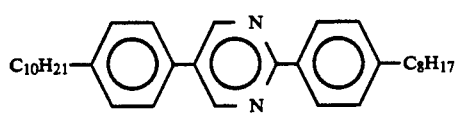 (204)
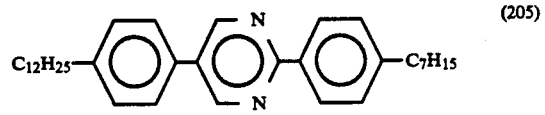 (205)
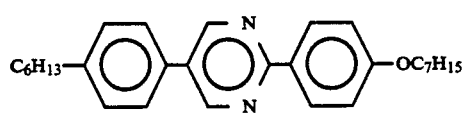 (206)
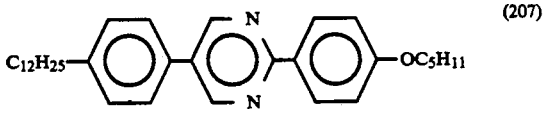 (207)
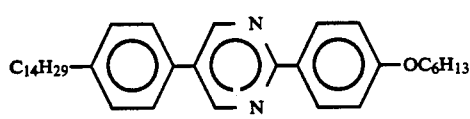 (208)
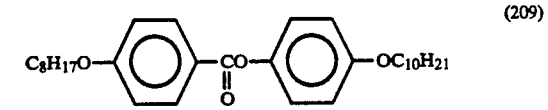 (209)
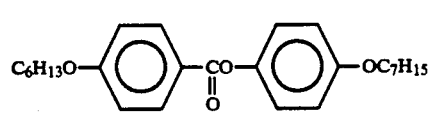 (210)
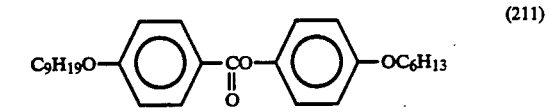 (211)
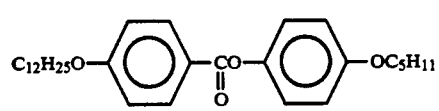 (212)
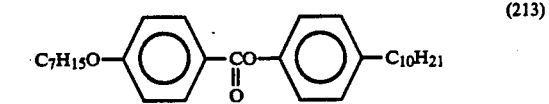 (213)
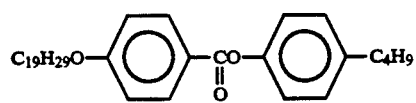 (214)
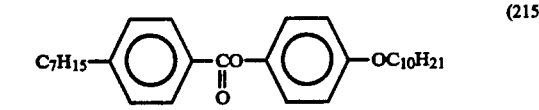 (215)
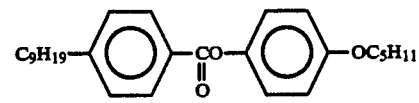 (216)
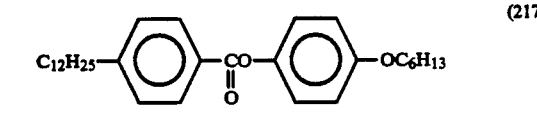 (217)
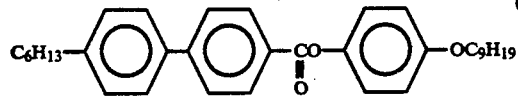 (218)
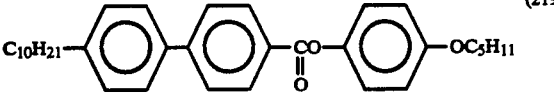 (219)
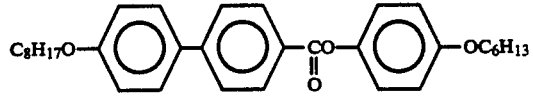 (220)

-continued
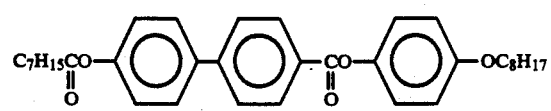 (221)
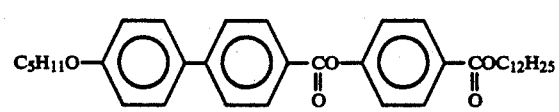 (222)
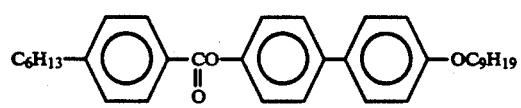 (223)
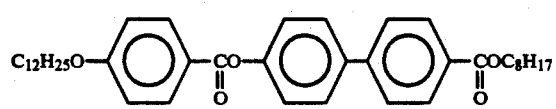 (224)
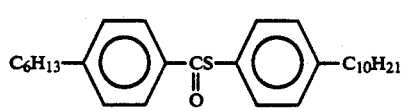 (225)  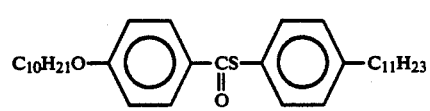 (226)
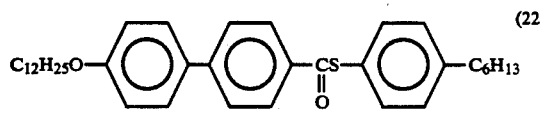 (227)  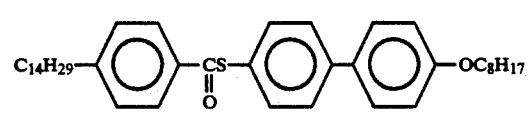 (228)
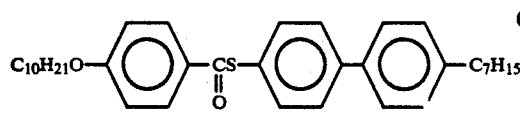 (229)  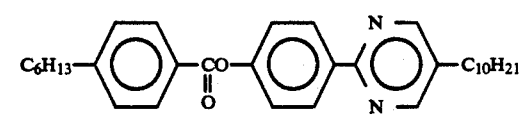 (230)
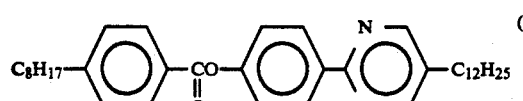 (231)  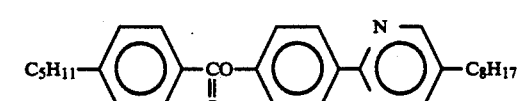 (232)
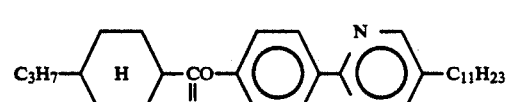 (233)  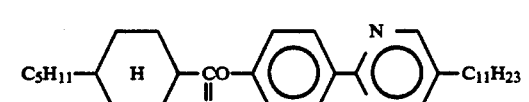 (234)
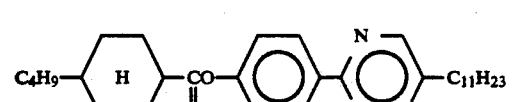 (235)  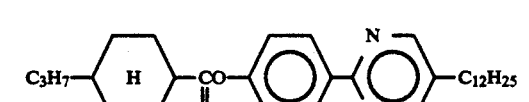 (236)
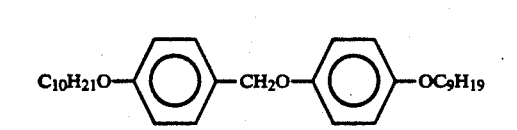 (237)  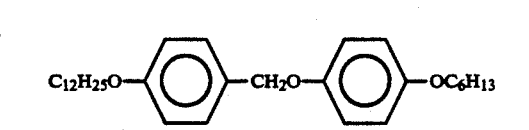 (238)
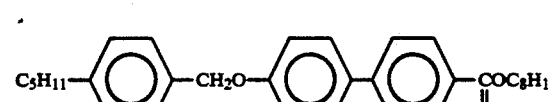 (239)
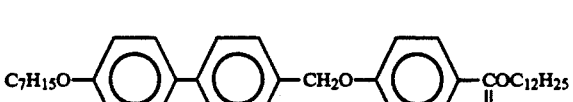 (240)

-continued

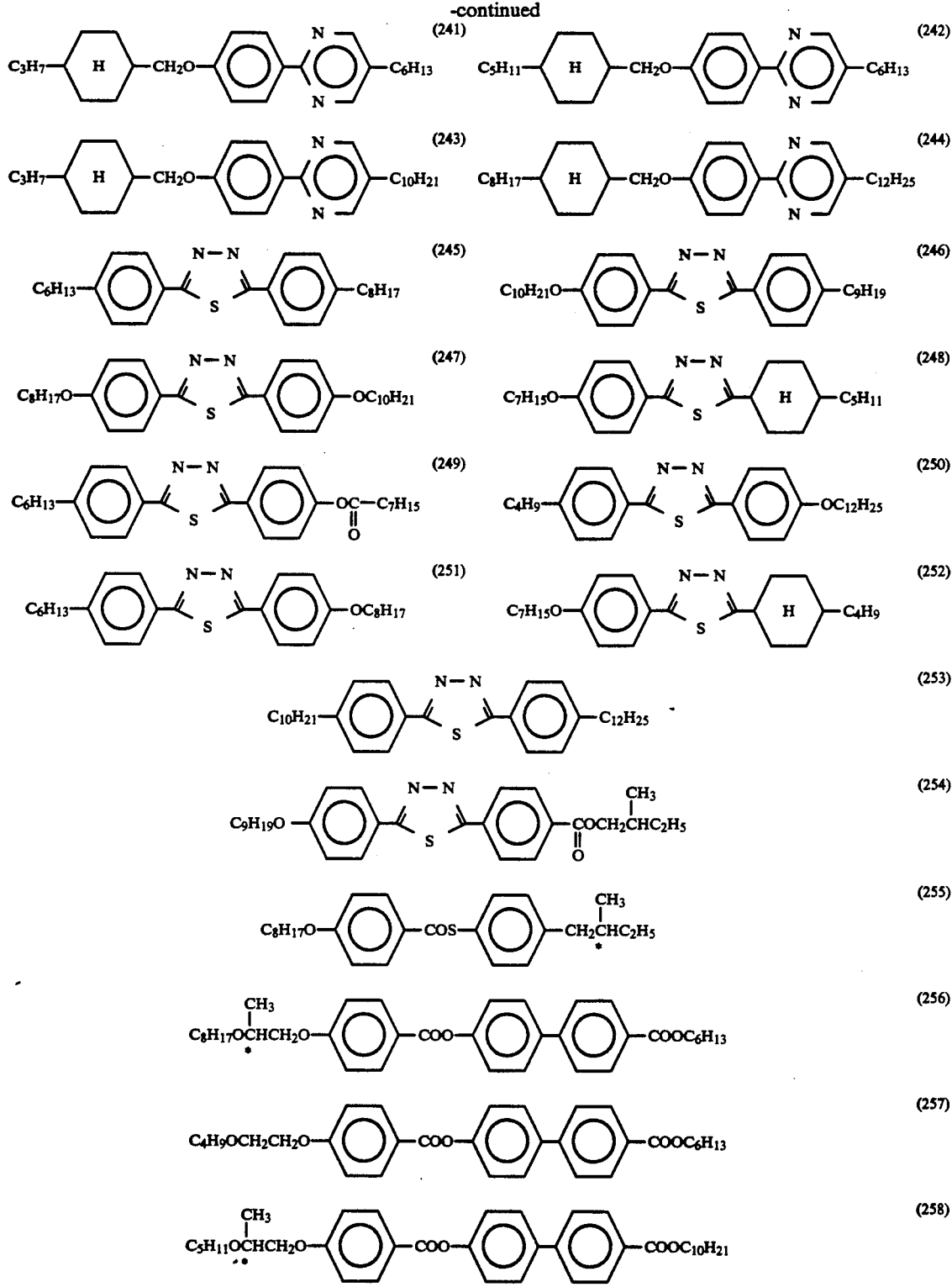

The ferroelectric liquid crystal device according to the present invention may preferably be prepared by heating the liquid crystal composition prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the ferroelectric liquid crystal device prepared as described above for explanation of the structure thereof.

Referring to FIG. 1, the ferroelectric liquid crystal device includes a ferroelectric liquid crystal layer 1 disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2-10 wt. %, by spinner coating, dip coating, screen printing, spray coating or roller coating, followed by curing or hardening under prescribed hardening condition (e.g., by heating). The insulating alignment control layer may have a thickness of ordinarily 30 Å–1 micron, preferably 30–3000 Å, further preferably 50–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a ferroelectric liquid crystal is sealed up to provide a ferroelectric liquid crystal layer 1 in a thickness of generally 0.5 to 20 microns, preferably 1 to 5 microns.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

Figure 2:
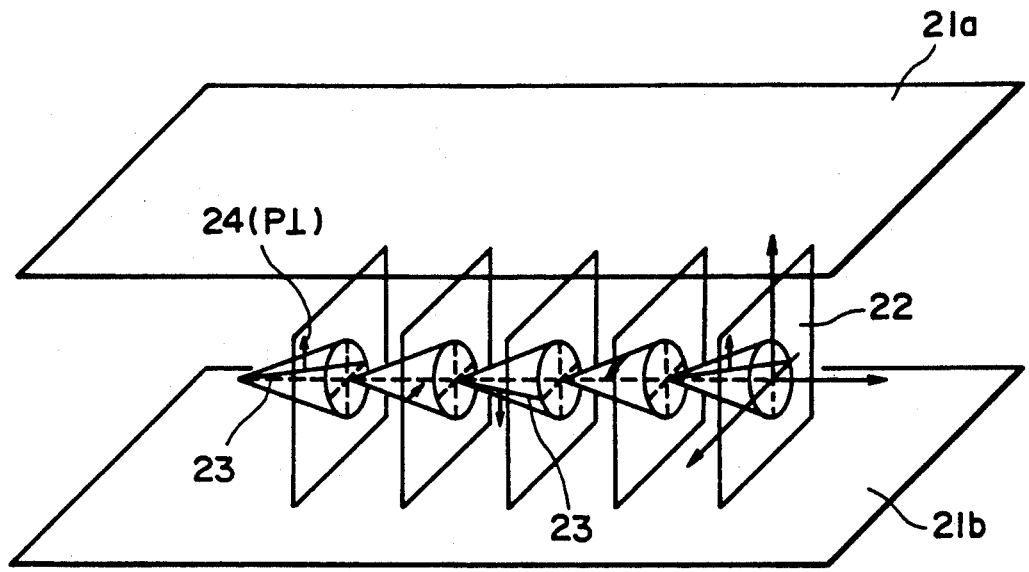
FIGS. 2 and 3 are schematic perspective views of a device cell embodiment for illustrating the operation principle of a ferroelectric liquid crystal device.

FIG. 2 is a schematic illustration of a ferroelectric liquid crystal cell (device) for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment ($P_\perp$) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal. molecule 23 is unwound or released to change the alignment direction of respective liquid crystal molecules 23 so that the dipole moments ($P_\perp$) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
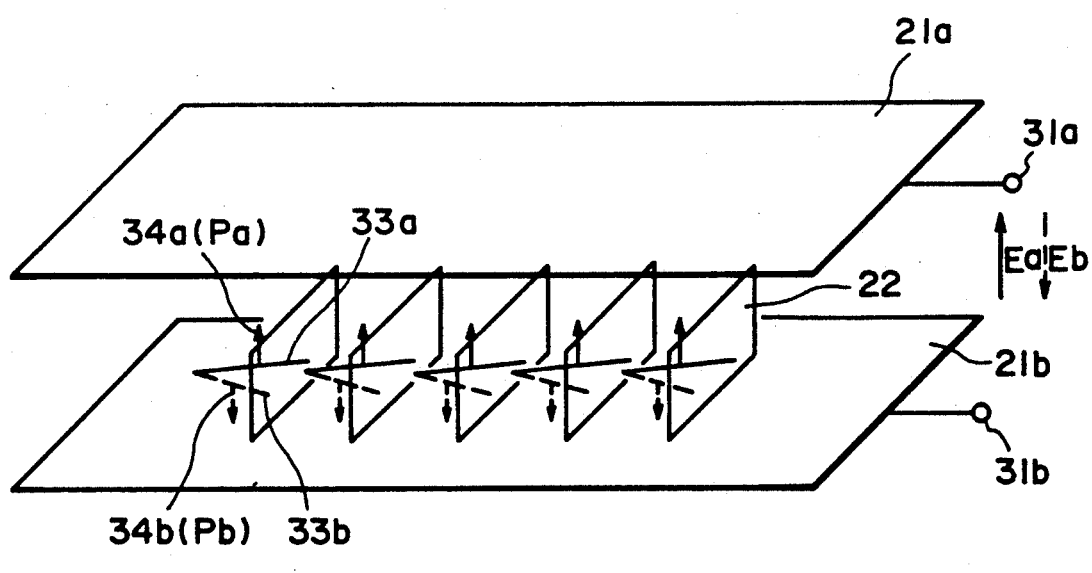

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages as described above. First is that the response speed is quite fast. Second is that the orientation of the liquid crystal molecules shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb, the direction of which is opposite to that of the electric field Ea, is applied thereto, the liquid crystal molecules are oriented to the second stable state 33b, whereby the directions of the molecules are changed. This state is similarly stably retained even if the electric field is removed. Further, as long as the magnitude of the electric field Ea or Eb being applied is not above a certain threshold value, the liquid crystal molecules are placed in the respective orientation states.

When such a ferroelectric liquid crystal device comprising a ferroelectric liquid crystal composition as described above between a pair of electrode plates is constituted as a simple matrix display device, the device may be driven by a driving method as disclosed in Japanese Laid-Open Patent Applications (KOKAI) Nos. 193426/1984, 193427/1984, 156046/1985, 156047/1985, etc.

Hereinbelow, the present invention will be explained more specifically with reference to examples. It is however to be understood that the present invention is not restricted to these examples.

EXAMPLE 1

2-(3-fluoro-4-octyloxyphenyl)-5-(4-decylphenyl)-1,3,4-thiadiazole (Example Compound No. I-84) was synthesized through the following steps i) to iii).

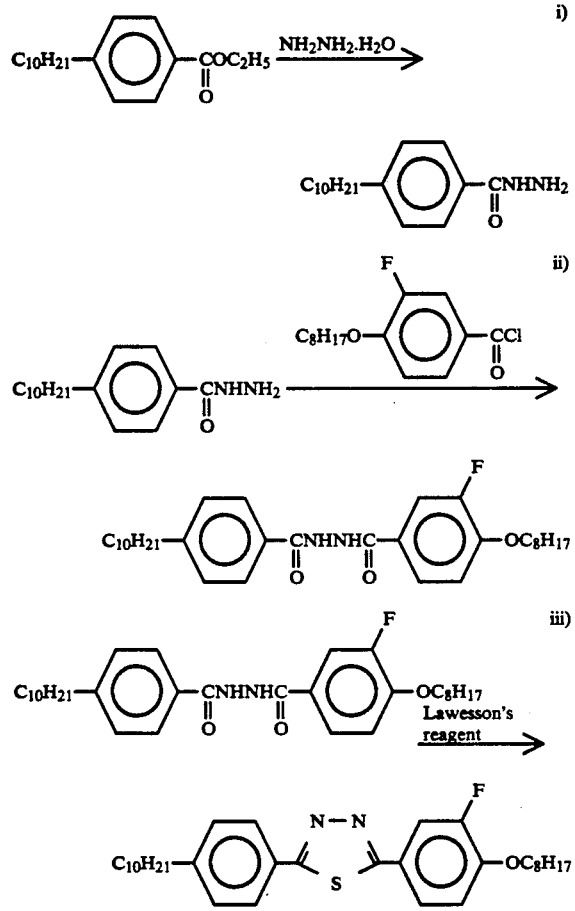

Step i) Production of A-decylbenzohydrazine 18 ml of ethanol was added to 10.0 g of ethyl 4-decylbenzoate, and then 20 g of 80%-hydrazine hydrate was added thereto, followed by refluxing for 16 hours. After the reaction, the reaction mixture was poured into 200 ml of iced water to precipitate a crystal. The crystal was recovered by filtration and recrystallized from ethanol to obtain 6.93 g of 4-decylbenzohydrazide (Yield: 72.9%).

Step ii) Production of N-(4-decylbenzo)-N'-(3-fluoro-4-octyloxybenzo)hydrazide 1.00 g (3.62 mM) of 4-decylbenzohydrazide, 1.13 g (3.78 mM) of 3-fluoro-4-octyloxybenzoyl chloride and 20 ml of dioxane were mixed and heated to 86°–92° C. under stirring. To the mixture, 1.31 ml of pyridine was added, followed by stirring for 50 minutes at 90°–92° C. After the reaction, the reaction mixture was poured into 150 ml of iced water, followed by addition of common salt and stirring at room temperature to precipitate a crystal. The crystal was recovered by filtration, followed by washing with water and further washing with methanol to obtain 1.87 g of N-(4-decylbenzo)-N'-(3-fluoro-4-octyloxybenzo)hydrazide (Yield: 98.1%).

Step iii) Production of 2-(3-fluoro-4-octyloxyphenyl)-5-(4-decylphenyl)-1,3,4-thiadiazole 1.50 g (2.85 mM) of N-(4-decylbenzo-N'-(3-fluoro-4-octyloxybenzo)hydrazide, 1.25 g (3.09 mM) of Lawesson's reagent and 25 ml of tetrahydrofuran (THF) were mixed, followed by refluxing for 1 hour under stirring by using a refluxing apparatus equipped with an alkali trap. After the reaction, the reaction mixture was poured into a solution of 0.98 g of sodium hydroxide in 150 ml of iced water, followed by addition of common salt and stirring at room temperature to precipitate a crystal. The crystal was recovered by filtration and washed with water, followed by purification by silica gel column chromatography (eluent: toluene) and recrystallization from a mixture solvent (toluene/methanol) to obtain 1.21 g of 2-(3-fluoro-4-octyloxyphenyl)-5-(4-decylphenyl)-1,3,4-thiadiazole (Yield: 81.0%).

Phase transition temperature (°C.)

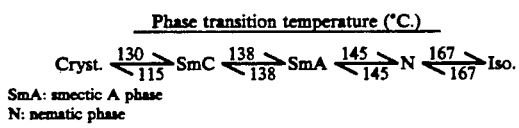

Herein, the respective symbols denote the following phases, Iso.: isotropic phase, SmC: smectic C phase, and Cryst.: crystal.

EXAMPLE 2

2-(3-fluoro-4-acetoxyphenyl)-5-(4-hexylphenyl)-1,3,4-thiadiazole (Example Compound No. I-103) was synthesized in the same manner as in Example 1.

Phase transition temperature (°C.)

Cryst. $\underset{115}{\overset{130}{\rightleftarrows}}$ SmC $\underset{138}{\overset{138}{\rightleftarrows}}$ SmA $\underset{145}{\overset{145}{\rightleftarrows}}$ N $\underset{167}{\overset{167}{\rightleftarrows}}$ Iso.

SmA: smectic A phase
N: nematic phase

EXAMPLE 3

2-(3-fluoro-4-hexyloxyphenyl)-5-(4-hexylphenyl)-1,3,4-thiadiazole (Example Compound No. I-72) was synthesized through the following steps i) and ii).

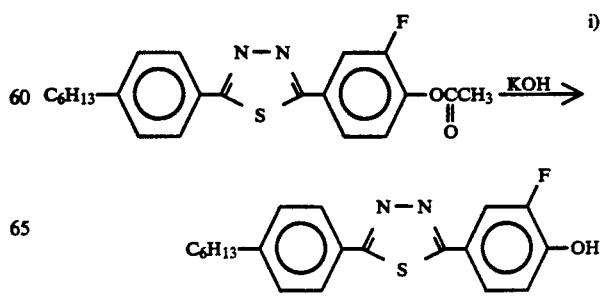

-continued

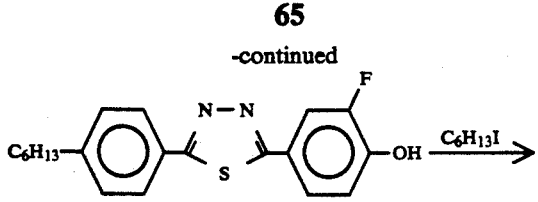

Step i) Production of 2-(3-fluoro-4-hydroxyphenyl)-5-(4-hexylphenyl)-1,3,4-thiadiazole 0.90 g of 85%-potassium hydroxide was added to 40 ml of ethanol and heated to 60°–65° C. on an oil bath. Under stirring, 2.00 g (5.02 mM) of 2-(3-fluoro-4-acetoxyphenyl)-5-(4-hexylphenyl)-1,3,4-thiadiazole was added thereto. To the mixture, 1.20 ml of hydrochloric acid was added (pH=about 3) and then common salt was added, followed by stirring at room temperature to precipitate a crystal. The crystal was recovered by filtration, followed by recrystallization from a mixture solvent (acetone/ethyl acetate) to obtain 1.14 g of 2-(3-fluoro-4-hydroxyphenyl)-5-(4-hexylphenyl)-1,3,4-thiadiazole (Yield: 63.7%).

Step ii) Production of 2-(3-fluoro-4-hexyloxyphenyl)-5-(4-hexylphenyl)-1,3,4-thiadiazole 0.30 g (0.84 mM) of 2-(3-fluoro-4-hydroxyphenyl)-5-(4-hexylphenyl)-1,3,4-thiadiazole, 0.23 g (1.09 mM) of hexyl iodide, 0.08 g of 85%-potassium hydroxide and 6 ml of butanol were mixed, followed by refluxing for 5 hours under stirring. After the reaction, 10 ml of methanol was added to the reaction mixture, followed by cooling to room temperature and further cooling in a freezer to precipitate a crystal. The crystal was recovered by filtration and washed with methanol. The resultant crystal was dissolved in toluene and washed with water, followed by drying with anhydrous magnesium sulfate. The magnesium sulfate was recovered by filtration and the filtrate was condensed into a solid. The solid was purified by silica gel column chromatography (eluent: toluene) and recrystallized from a mixture solvent (ethanol/hexane) to obtain 0.13 g of 2-(3-fluoro-4-hexyloxyphenyl)-5-(4-hexylphenyl)-1,3,4-thiadiazole (Yield: 35.1%).

Phase transition temperature (°C.)

Cryst. $\underset{70}{\overset{75}{\rightleftarrows}}$ SmC $\underset{156}{\overset{157}{\rightleftarrows}}$ N $\underset{164}{\overset{164}{\rightleftarrows}}$ Iso.

EXAMPLE 4

2-(3-fluoro-4-butyloxyphenyl)-5-(4-hexylphenyl)-1,3,4-thiadiazole (Example Compound No. I-70) was synthesized in the same manner as in Example 3.

Phase transition temperature (°C.)

Cryst. $\underset{74}{\overset{84}{\rightleftarrows}}$ SmC $\underset{148}{\overset{152}{\rightleftarrows}}$ N $\underset{167}{\overset{168}{\rightleftarrows}}$ Iso.

EXAMPLE 5

2-hexyl-5-(3-fluoro-4-hetanoyloxyphenyl)-1,3,4-thiadiazole (Example Compound No. I-9) was synthesized through the following steps i) to iv).

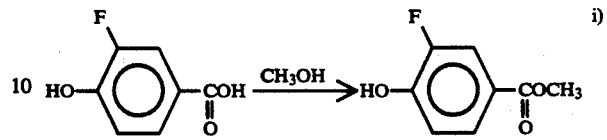

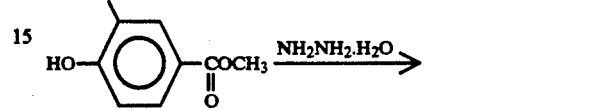

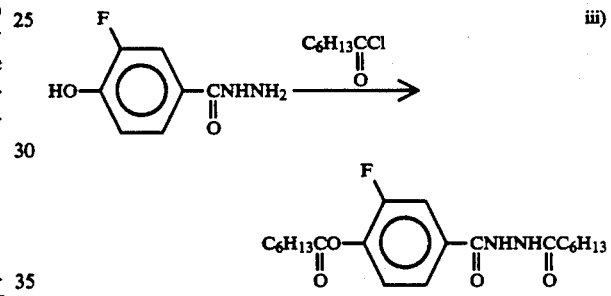

Step i) Production of methyl 3-fluoro-4-hydroxybenzoate 10.0 g (64.1 mM) of 3-fluoro-4-hydroxybenzoic acid, 150 ml of 1,2-dichloroethane, 80 ml of methanol and 10 ml of concentrated sulfuric acid were mixed, followed by refluxing for 5.5 hours under stirring and further stirring for 12 hours at room temperature. After the reaction, a solution of salt was added to the reaction mixture, followed by sufficient shaking to separate the reaction mixture. The organic layer was recovered from the reaction mixture and the water layer was subjected to extraction with methylene chloride to be added thereto. The resultant organic layer was washed with a 5%-aqueous solution of sodium hydrogencarbonate in a solution of salt and further washed with a solution of salt, followed by drying with anhydrous sodium sulfate. The sodium sulfate was recovered by filtration and the filtrate was condensed into a solid. Hexane was added to the solid and subjected to filtration to obtain 9.98 g of methyl 3-fluoro-4-hydroxybenzoate (Yield: 91.6%).

Step ii) Production of 3-fluoro-4-hydroxybenzohydrazide 10.00 g (58.8 mM) of methyl 3-fluoro-4-hydroxybenzoate and 17.5 ml of 80%-hydrazine hydrate were mixed and stirred for 1 hour and 20 minutes at 100° C., followed by cooling to room temperature. The resultant mixture was poured into 150 ml of iced water and 16.8 ml of concentrated hydrochloric acid was added thereto (pH=about 8), followed by addition of common salt and stirring at room temperature to precipitate a crystal. The crystal was recovered by filtration and stirred in methanol at room temperature. The resultant crystal was recovered from the above mixture by filtration to obtain 9.26 g of 3-fluoro-4-hydroxybenzohydrazide (Yield: 92.6%).

Step iii) Production of N-heptanoyl-N'-(3-fluoro-4-heptanoyloxybenzo)hydrazide 5.00 g (29.4 mM) of 3-fluoro-4-hydroxybenzohydrazide and 150 ml of pyridine were mixed and stirred on an iced water bath. To the mixture, 13.5 ml (87.2 mM) of heptanoyl chloride was added dropwise in 10 minutes at 2°-12° C., followed by stirring for 20 minutes on an iced water bath and further stirring for 10 minutes at room temperature. The resultant mixture was poured into 500 ml of iced water and common salt was added thereto, followed by stirring at room temperature to precipitate a crystal. The crystal was recovered by filtration and dissolved in 300 ml of ethyl acetate, followed by washing with water. The resultant water layer was subjected to extraction with ethyl acetate to be added to the resultant organic layer, followed by drying with anhydrous sodium sulfate. The sodium sulfate was recovered by filtration and the filtrate was condensed into a solid. Hexane was added to the solid, followed by cooling with iced water to precipitate a crystal. The crystal was recovered by filtration to obtain 5.96 g of N-heptanoyl-N'-(3-fluoro-4-heptanoyloxybenzo)hydrazide (Yield: 51.4%).

Step iv) Production of 2-hexyl-5-(3-fluoro-4-heptanoyloxyphenyl)-1,3,4-thiadiazole 5.80 g (14.7 mM) of N-heptanoyl-N'-(3-fluoro-4-heptanoyloxybenzo)hydrazide, 6.40 g (15.8 mM) of Lawesson's reagent and 100 ml of tetrahydrofuran (THF) were mixed, followed by refluxing for 1 hour under stirring by using a refluxing apparatus equipped with an alkali trap. After the reaction, the reaction mixture was cooled to room temperature and poured into a solution of 5.19 g of sodium hydroxide in 400 ml of iced water, followed by addition of common salt and stirring at room temperature. After stirring, the resultant mixture was subjected to extraction with ethyl acetate at room temperature. The resultant ethyl acetate layer was washed with saturated saline solution, followed by drying with anhydrous sodium sulfate. The sodium sulfate was recovered by filtration and the filtrate was condensed into a solid. The solid was purified by silica gel column chromatography (eluent: toluene) and recrystallized from methanol to obtain 3.71 g of 2-hexyl-5-(3-fluoro-4-heptanoyloxyphenyl)-1,3,4-thiadiazole (Yield: 64.3%).

Phase transition temperature (°C.)

$$\text{Cryst.} \underset{36}{\overset{51}{\rightleftarrows}} \text{Iso.}$$

EXAMPLE 6

A liquid crystal composition A was prepared by mixing the following compounds in the respectively indicated proportions.

| Ex. Comp. No. | Structural formula | wt. parts |
|---|---|---|
| 173 | $C_8H_{17}$—[N=N phenyl]—[phenyl]—$OC_6H_{13}$ | 54.3 |
| 174 | $C_8H_{17}$—[N=N phenyl]—[phenyl]—$OC_9H_{19}$ | 27.1 |
| 175 | $C_{10}H_{21}$—[N=N phenyl]—[phenyl]—$OC_8H_{17}$ | 13.6 |
| 132 | $C_{12}H_{25}$—[N=N phenyl]—[phenyl]—$OCH_2\overset{*}{C}HC_6H_{13}$ (F) | 2.5 |
| 150 | $C_{10}H_{21}$—[N=N phenyl]—[phenyl]—$OCH_2\overset{*}{C}HC_6H_{13}$ (F) | 2.5 |

The liquid crystal composition A was further mixed with the following Example Compound No. I-84 in the proportions indicated below to provide a liquid crystal composition B.

| Ex. Comp. No. | Structural formula | wt. parts |
|---|---|---|
| I-84 | 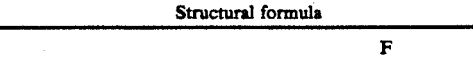 | 5 |
| | Composition A | 95 |

The liquid crystal composition B showed the following phase transition series.

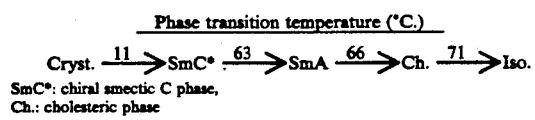

SmC*: chiral smectic C phase,
Ch.: cholesteric phase

Then, two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 2 microns as measured by a Berek compensator.

Then, the liquid crystal composition B was heated into an isotropic liquid, and injected into the above prepared cell under vacuum and, after sealing, was gradually cooled at a rate of 20° C./hour to 25° C. to prepare a ferroelectric liquid crystal device.

The ferroelectric liquid crystal device was subjected to measurement of the magnitude of spontaneous polarization Ps and optical response time (time from voltage application until the transmittance change reaches 90% of the maximum under the application of a peak-to-peak voltage Vpp of 20 V in combination with right-angle cross-nicol polarizers).

The results are shown below.

| | 10° C. | 30° C. | 45° C. |
|---|---|---|---|
| Response time (μsec) | 450 | 212 | 122 |
| Ps (nC/cm²) | 3.68 | 2.61 | 1.74 |

EXAMPLE 7

A liquid crystal composition C was prepared by mixing the following compounds in the respectively indicated proportions.

| Ex. Comp. No. | Structural formula | wt. parts |
|---|---|---|
| 8 | 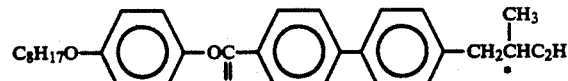 | 16 |
| 9 |  | 22.5 |
| 18 | 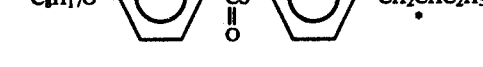 | 64 |
| 23 | 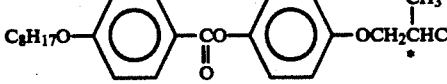 | 10 |

| Ex. Comp. No. | Structural formula | wt. parts |
| --- | --- | --- |
| 24 | $C_{11}H_{23}O$–⟨N=⟩–⟨⟩–O(CH$_2$)$_2$CH(CH$_3$)C$_2$H$_5$ | 10 |
| 43 | $C_{10}H_{21}O$–⟨⟩–CS(O)–⟨⟩–OCH$_2$CH(CH$_3$)C$_2$H$_5$ | 22.5 |
| 63 | $C_{10}H_{21}OCO$–⟨⟩–⟨⟩–OCO–⟨⟩–OCH$_2$CH(CH$_3$)OC$_5$H$_{11}$ | 15 |
| 87 | $C_6H_{13}OCO$–⟨⟩–⟨⟩–OCO–⟨⟩–OCH$_2$CH(CH$_3$)OC$_8$H$_{17}$ | 15 |
| 124 | $C_{12}H_{25}O$–⟨⟩–COO–⟨⟩–OCH$_2$CH(F)C$_6$H$_{13}$ | 6.75 |
| 136 | $C_8H_{17}O$–⟨⟩–COO–⟨⟩–OCH$_2$CH(F)C$_5$H$_{11}$ | 18.75 |
| 236 | $C_3H_7$–⟨H⟩–COO–⟨⟩–⟨N=N⟩–C$_{12}H_{25}$ | 20 |

The liquid crystal composition C was further mixed with the following Example Compounds in the proportions indicated below to provide a liquid crystal composition D.

| Ex. Comp. No. | Structural formula | wt. parts |
| --- | --- | --- |
| 1-4 | $C_{12}H_{25}$–⟨N–N/S⟩–⟨F⟩–$C_{10}H_{21}$ | 4 |
| 1-16 | $C_{10}H_{21}$–⟨N–N/S⟩–⟨F⟩–$OC_{16}H_{33}$ | 2 |
| 1-23 | $C_2H_5CH(CH_3)(CH_2)_2$–⟨N–N/S⟩–⟨F⟩–OCOC$_6$H$_{13}$ | 4 |
| Composition C | | 90 |

A ferroelectric liquid crystal device was prepared in the same manner as in Example 6 except for using the composition D. In the ferroelectric liquid crystal device, a monodomain with a good and uniform alignment characteristic was observed. The ferroelectric liquid crystal device was subjected to measurement of response time and observation of a switching state, etc. in the same manner as in Example 6, whereby the following results were obtained.

Compounds Nos. I-4, I-16 and I-23 in the respectively indicated proportions.

| Ex. Comp. No. | Structural formula | wt. parts |
|---|---|---|
| 1-14 | $C_8H_{17}$—\<(N=N)(S)\>—\<C_6H_3(F)\>—$OC_8H_{17}$ | 3 |
| 1-20 | $C_{14}H_{29}$—\<(N=N)(S)\>—\<C_6H_3(F)\>—$OC_{16}H_{33}$ | 3 |
| 1-43 | $C_5H_{11}$—\<Ph\>—\<(N=N)(S)\>—\<C_6H_3(F)\>—$C_5H_{11}$ | 2 |
| 1-167 | $C_5H_{11}$—\<H\>—\<(N=N)(S)\>—\<C_6H_3(F)\>—$OCH_2\overset{*}{C}H(CH_3)C_2H_5$ | 2 |
| Composition C | | 90 |

|  | 15° C. | 25° C. | 35° C. |
|---|---|---|---|
| Response time (μsec) | 310 | 211 | 170 |

COMPARATIVE EXAMPLE 7

A ferroelectric liquid crystal device was prepared in the same manner as in Example 6 except that the above liquid crystal composition C prepared in Example 7 was injected into a cell, and the device was subjected to measurement of optical response time. The results are shown below.

|  | 15° C. | 25° C. | 35° C. |
|---|---|---|---|
| Response time (μsec) | 450 | 270 | 195 |

EXAMPLE 8

A liquid crystal composition E was prepared in the same manner as in Example 7 except that the following Example Compounds were used instead of Example Compounds Nos. I-4, I-16 and I-23 in the respectively indicated proportions.

A ferroelectric liquid crystal device was prepared in the same manner as in Example 6 except for using the composition E. In the ferroelectric liquid crystal device, a monodomain with a good and uniform alignment characteristic was observed. The ferroelectric liquid crystal device was subjected to measurement of response time and observation of a switching state, etc. in the same manner as in Example 6, whereby the following results were obtained.

|  | 15° C. | 25° C. | 35° C. |
|---|---|---|---|
| Response time (μsec) | 318 | 221 | 179 |

Further, when the device was driven, a clear switching action was observed, and good bistability was shown after the termination of the voltage application.

EXAMPLE 9

A liquid crystal composition F was prepared in the same manner as in Example 7 except that the following Example Compounds were used instead of Example Compounds Nos. I-4, I-16 and I-23 in the respectively indicated proportions.

| Ex. Comp. No. | Structural formula | wt. parts |
|---|---|---|
| 1-77 |  | 2 |

-continued

| Ex. Comp. No. | Structural formula | wt. parts |
|---|---|---|
| I-84 | $C_{10}H_{21}$—⌬—C(S)=N—N=C—⌬(F)—$OC_8H_{17}$ | 2 |
| I-162 | $C_8H_{17}$—H(cyclohexyl)—C(S)=N—N=C—⌬(F)—$OCOC_{14}H_{29}$ | 1 |
| I-175 | $C_4H_9$—(pyridyl)—C(S)=N—N=C—⌬(F)—$OCOC_8H_{17}$ | 1 |
| I-176 | $C_8H_{17}$—(pyridyl)—C(S)=N—N=C—⌬(F)—$COC_6H_{13}$ | 2 |
| Composition C | | 92 |

A ferroelectric liquid crystal device was prepared in the same manner as in Example 6 except for using the composition F. In the ferroelectric liquid crystal device, a monodomain with a good and uniform alignment characteristic was observed. The ferroelectric liquid crystal device was subjected to measurement of response time and observation of a switching state, etc. in the same manner as in Example 6, whereby the following results were obtained.

|  | 15° C. | 25° C. | 35° C. |
|---|---|---|---|
| Response time (μsec) | 325 | 224 | 181 |

Further, when the device was driven, a clear switching action was observed, and good bistability was shown after the termination of the voltage application.

EXAMPLE 10

A liquid crystal composition G was prepared in the same manner as in Example 7 except that the following Example Compounds were used instead of Example Compounds Nos. I-4, I-16 and I-23 in the respectively indicated proportions.

| Ex. Comp. No. | Structural formula | wt. parts |
|---|---|---|
| I-84 | $C_{10}H_{21}$—⌬—C(S)=N—N=C—⌬(F)—$OC_8H_{17}$ | 2 |
| I-135 | $C_{10}H_{21}CO$—⌬—C(S)=N—N=C—⌬(F)—$OC_8H_{17}$ | 2 |
| I-196 | $C_8H_{17}$—(pyrazinyl)—C(S)=N—N=C—⌬(F)—$OCC_6H_{13}$ | 2 |

-continued

| Ex. Comp. No. | Structural formula | wt. parts |
|---|---|---|
| I-203 | C$_{10}$H$_{21}$–[pyrimidine]–CH=N–N=CH–[phenyl(F)]–OC$_{12}$H$_{25}$ (with S linkage) | 2 |
| I-209 | C$_2$H$_5$CH(CH$_3$)(CH$_2$)$_3$O–[pyrimidine]–CH=N–N=CH–[phenyl(F)]–OCOC$_8$H$_{17}$ (with S linkage) | 2 |
| Composition C | | 90 |

A ferroelectric liquid crystal device was prepared in the same manner as in Example 6 except for using the composition G. In the ferroelectric liquid crystal device, a monodomain with a good and uniform alignment characteristic was observed. The ferroelectric liquid crystal device was subjected to measurement of response time and observation of a switching state, etc. in the same manner as in Example 6, whereby the following results were obtained.

|  | 15° C. | 25° C. | 35° C. |
|---|---|---|---|
| Response time (μsec) | 321 | 217 | 180 |

Further, when the device was driven, a clear switching action was observed, and good bistability was shown after the termination of the voltage application.

EXAMPLE 11

A liquid crystal composition H was prepared by mixing the following compounds in the respectively indicated proportions.

| Ex. Comp. No. | Structural formula | wt. parts |
|---|---|---|
| 20 | C$_{10}$H$_{21}$O–[pyrimidine]–[phenyl]–O(CH$_2$)$_3$CH(CH$_3$)C$_2$H$_5$ | 15 |
| 21 | C$_8$H$_{17}$O–[pyrimidine]–[phenyl]–O(CH$_2$)$_3$CH(CH$_3$)C$_2$H$_5$ | 15 |
| 58 | C$_8$H$_{17}$–[pyrimidine]–[phenyl]–O(CH$_2$)$_3$CH(CH$_3$)OC$_5$H$_{11}$ | 10 |
| 89 | C$_{10}$H$_{21}$–[pyrimidine]–[phenyl]–O(CH$_2$)$_3$CH(CH$_3$)OC$_3$H$_7$ | 20 |
| 120 | C$_{10}$H$_{21}$–[pyrimidine]–[phenyl]–OCO–[phenyl]–OCH$_2$CH(F)C$_6$H$_{13}$ | 13 |
| 129 | C$_{10}$H$_{21}$–[pyrimidine]–[phenyl]–OCH$_2$CH(F)C$_8$H$_{17}$ | 7 |
| 236 | C$_3$H$_7$–[cyclohexyl]–CO–O–[phenyl]–[pyrimidine]–C$_{12}$H$_{25}$ | 15 |

| Ex. Comp. No. | Structural formula | wt. parts |
| --- | --- | --- |
| 242 | $C_5H_{11}$—⟨H⟩—$CH_2O$—⟨⟩—⟨N,N⟩—$C_6H_{13}$ | 5 |

The liquid crystal composition H was further mixed with the following Example Compounds in the proportions respectively indicated below to provide a liquid crystal composition I.

| Ex. Comp. No. | Structural formula | wt. parts |
| --- | --- | --- |
| I-3 | $C_8H_{17}$—(N—N,S)—⟨F⟩—$C_8H_{17}$ | 3 |
| I-13 | $C_8H_{17}$—(N—N,S)—⟨F⟩—$OC_6H_{13}$ | 3 |
| I-72 | $C_6H_{13}$—⟨⟩—(N—N,S)—⟨F⟩—$OC_6H_{13}$ | 2 |
| Composition H | | 92 |

A ferroelectric liquid crystal device was prepared in the same manner as in Example 6 except that the above liquid crystal composition I was used, and the device was subjected to measurement of optical response time. The results are shown below.

| | 15° C. | 25° C. | 35° C. |
| --- | --- | --- | --- |
| Response time (μsec) | 119 | 87 | 74 |

COMPARATIVE EXAMPLE 11

A ferroelectric liquid crystal device was prepared in the same manner as in Example 6 except that the liquid crystal composition H prepared in Example 11 was injected into a cell, and the device was subjected to measurement of optical response time. The results are shown below.

| | 15° C. | 25° C. | 35° C. |
| --- | --- | --- | --- |
| Response time (μsec) | 155 | 100 | 80 |

EXAMPLE 12

A liquid crystal composition J was prepared in the same manner as in Example 11 except that the following Example Compounds were used instead of Example Compounds Nos. I-3, I-13 and I-72 in respectively indicated proportions.

| Ex. Comp. No. | Structural formula | wt. parts |
| --- | --- | --- |
| I-9 | $C_6H_{13}$—(N—N,S)—⟨F⟩—$OCC_6H_{13}$‖O | 3 |
| I-17 | $C_{12}H_{25}$—(N—N,S)—⟨F⟩—$OCC_{10}H_{21}$‖O | 3 |

-continued

| Ex. Comp. No. | Structural formula | wt. parts |
|---|---|---|
| I-30 | $C_6H_{13}$-C(=N-N)-S- connected to phenyl with F and -O(CH$_2$)$_3$CH(CH$_3$)CH$_2$C$_2$H$_5$ | 3 |
| | Composition H | 91 |

A ferroelectric liquid crystal device was prepared in the same manner as in Example 6 except for using the composition J. The ferroelectric liquid crystal device was subjected to measurement of response time in the same manner as in Example 6, whereby the following results were obtained.

|  | 15° C. | 25° C. | 35° C. |
|---|---|---|---|
| Response time (μsec) | 112 | 82 | 70 |

EXAMPLE 13

A liquid crystal composition K was prepared in the same manner as in Example 11 except that the following Example Compounds were used instead of Example Compounds Nos. I-3, I-13 and I-72 in the respectively indicated proportions.

| Ex. Comp. No. | Structural formula | wt. parts |
|---|---|---|
| I-44 | $C_5H_{11}$-phenyl-C(=N-N)-S-phenyl(F)-$C_7H_{15}$ | 4 |
| I-70 | $C_6H_{13}$-phenyl-C(=N-N)-S-phenyl(F)-$OC_4H_9$ | 2 |
| I-81 | $C_8H_{17}$-phenyl-C(=N-N)-S-phenyl(F)-$OC_{16}H_{33}$ | 2 |
| | Composition H | 92 |

A ferroelectric liquid crystal device was prepared in the same manner as in Example 6 except for using the composition K. The ferroelectric liquid crystal device was subjected to measurement of response time in the same manner as in Example 6, whereby the following results were obtained.

|  | 15° C. | 25° C. | 35° C. |
|---|---|---|---|
| Response time (μsec) | 139 | 99 | 82 |

EXAMPLE 14

A liquid crystal composition L was prepared in the same manner as in Example 11 except that the following Example Compounds were used instead of Example Compounds Nos. I-3, I-13 and I-72 in the respectively indicated proportions.

| Ex. Comp. No. | Structural formula | wt. parts |
|---|---|---|
| I-77 | $C_8H_{17}$-phenyl-C(=N-N)-S-phenyl(F)-$OC_6H_{13}$ | 3 |
| I-84 | $C_{10}H_{21}$-phenyl-C(=N-N)-S-phenyl(F)-$OC_8H_{17}$ | 3 |

-continued

| Ex. Comp. No. | Structural formula | wt. parts |
| --- | --- | --- |
| I-126 |  | 2 |
| I-141 |  | 2 |
| | Composition H | 90 |

A ferroelectric liquid crystal device was prepared in the same manner as in Example 6 except for using the composition L. The ferroelectric liquid crystal device was subjected to measurement of response time in the same manner as in Example 6, whereby the following results were obtained.

| | 15° C. | 25° C. | 35° C. |
| --- | --- | --- | --- |
| Response time (μsec) | 137 | 96 | 83 |

EXAMPLE 15

A liquid crystal composition M was prepared by mixing the following compounds in the respectively indicated proportions.

| Ex. Comp. No. | Structural formula | wt. parts |
| --- | --- | --- |
| 255 |  | 18 |
| 19 | 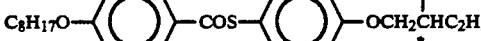 | 18 |
| 81 |  | 8 |
| 11 |  | 8 |
| 256 | 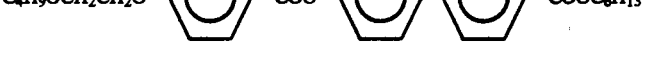 | 12 |
| 257 | | 12 |
| 258 | | 6 |
| 170 | 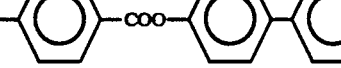 | 6 |

-continued

| Ex. Comp. No. | Structural formula | wt. parts |
|---|---|---|
| 174 | $C_8H_{17}$—[pyrazine]—[phenyl]—$OC_9H_{19}$ | 6 |
| 195 | $C_{10}H_{21}$—[pyrimidine]—[phenyl]—[phenyl]—$OC_5H_{11}$ | 4 |
| 203 | $C_9H_{19}$—[phenyl]—[pyrimidine]—[phenyl]—$C_6H_{13}$ | 2 |

The liquid crystal composition M was further mixed with the following Example Compounds in the proportions respectively indicated below to provide a liquid crystal composition N.

| | 10° C. | 25° C. | 40° C. |
|---|---|---|---|
| Response time (μsec) | 1622 | 488 | 164 |

| Ex. Comp. No. | Structural formula | wt. parts |
|---|---|---|
| I-93 | $C_{16}H_{33}$—[phenyl]—[thiadiazole(N—N,S)]—[phenyl(F)]—$OC_{12}H_{25}$ | 1 |
| I-144 | $C_2H_5\overset{*}{C}H(CH_3)(CH_2)_3O$—[phenyl]—[thiadiazole(N—N,S)]—[phenyl(F)]—$C_{10}H_{21}$ | 2 |
| I-151 | $C_{10}H_{21}O$—[phenyl]—[thiadiazole(N—N,S)]—[phenyl(F)]—$OCH_2\overset{*}{C}H(CH_3)OC_2H_5$ | 1 |
| I-157 | $C_4H_9$—[cyclohexyl(H)]—[thiadiazole(N—N,S)]—[phenyl(F)]—$OC_5H_{11}$ | 2 |
| I-166 | $C_3H_7$—[cyclohexyl(H)]—[thiadiazole(N—N,S)]—[phenyl(F)]—$OCH_2\overset{*}{C}H(CH_3)C_2H_5$ | 2 |
| Composition M | | 92 |

A ferroelectric liquid crystal device was prepared in the same manner as in Example 6 except for using the composition N. In the ferroelectric liquid crystal device, a monodomain with a good and uniform alignment characteristic was observed. The ferroelectric liquid crystal device was subjected to measurement of response time and observation of a switching state, etc. in the same manner as in Example 6, whereby the following results were obtained.

COMPARATIVE EXAMPLE 13

A ferroelectric liquid crystal device was prepared in the same manner as in Example 6 except that the liquid crystal composition M prepared in Example 15 was injected into a cell, and the device was subjected to measurement of optical response time. The results are shown below.

|  | 10° C. | 25° C. | 40° C. |
| --- | --- | --- | --- |
| Response time (μsec) | 1980 | 548 | 170 |

EXAMPLE 16

A liquid crystal composition O was prepared in the same manner as in Example 15 except that the following Example Compounds were used instead of Example Compounds Nos. I-93, I-144, I-151, I-157 and I-166 in the respectively indicated proportions.

was subjected to measurement of response time in the same manner as in Example 6, whereby the following results were obtained.

|  | 10° C. | 25° C. | 40° C. |
| --- | --- | --- | --- |
| Response time (μsec) | 1673 | 515 | 168 |

EXAMPLE 17

A liquid crystal composition P was prepared in the same manner as in Example 17 except that the following

| Ex. Comp. No. | Structural formula | wt. parts |
| --- | --- | --- |
| I-172 | C$_4$H$_9$—[pyridine]—C(S)=N—N=CH—[phenyl(F)]—C$_5$H$_{11}$ | 2 |
| I-173 | C$_6$H$_{13}$—[pyridine]—C(S)=N—N=CH—[phenyl(F)]—OC$_6$H$_{13}$ | 2 |
| I-213 | C$_{10}$H$_{21}$—[pyrazine]—C(S)=N—N=CH—[phenyl(F)]—OC(O)(CH$_2$)$_2$CH(CH$_3$)OC$_5$H$_{11}$ | 2 |
| I-216 | C$_{12}$H$_{25}$—[pyrazine]—C(S)=N—N=CH—[phenyl(F)]—OC(O)(CH$_2$)$_2$CH(CH$_3$)CHC$_2$H$_5$ | 1 |
| Composition M |  | 93 |

A ferroelectric liquid crystal device was prepared in the same manner as in Example 6 except for using the composition O. The ferroelectric liquid crystal device Example Compounds were used instead of Example Compounds Nos. I-4, I-16 and I-23 in the respectively indicated proportions.

| Ex. Comp. No. | Structural formula | wt. parts |
| --- | --- | --- |
| I-70 | C$_6$H$_{13}$—[phenyl]—C(S)=N—N=CH—[phenyl(F)]—OC$_4$H$_9$ | 2 |
| I-77 | C$_8$H$_{17}$—[phenyl]—C(S)=N—N=CH—[phenyl(F)]—OC$_6$H$_{13}$ | 3 |
| 245 | C$_6$H$_{13}$—[phenyl]—C(S)=N—N=CH—[phenyl]—C$_8$H$_{17}$ | 2 |
| 251 | C$_6$H$_{13}$—[phenyl]—C(S)=N—N=CH—[phenyl]—OC$_8$H$_{17}$ | 3 |

-continued

| Ex. Comp. No. | Structural formula | wt. parts |
|---|---|---|
| | Composition C | 90 |

A ferroelectric liquid crystal device was prepared in the same manner as in Example 6 except for using the composition P. The ferroelectric liquid crystal device was subjected to measurement of response time in the same manner as in Example 6, whereby the following results were obtained.

| | 15° C. | 25° C. | 35° C. |
|---|---|---|---|
| Response time (μsec) | 316 | 223 | 180 |

COMPARATIVE EXAMPLE 17

A liquid crystal composition Q was prepared in the same manner as in Example 17 except that the following Example Compounds were used instead of Example Compounds Nos. I-70, I-77, 245 and 251 in the respectively indicated proportions.

| Ex. Comp. No. | Structural formula | wt. parts |
|---|---|---|
| 245 | $C_6H_{13}$—⟨phenyl⟩—(thiadiazole N—N/S)—⟨phenyl⟩—$C_8H_{17}$ | 2 |
| 251 | $C_6H_{13}$—⟨phenyl⟩—(thiadiazole N—N/S)—⟨phenyl⟩—$OC_8H_{17}$ | 3 |
| | Composition C | 90 |

A ferroelectric liquid crystal device was prepared in the same manner as in Example 6 except for using the composition J. The ferroelectric liquid crystal device was subjected to measurement of response time in the same manner as in Example 6, whereby the following results were obtained.

| | 15° C. | 25° C. | 35° C. |
|---|---|---|---|
| Response time (μsec) | 364 | 241 | 184 |

As is apparent from the above Example 17 and Comparative Example 17, 4-substituted-3-fluorophenyl-thiadiazole derivatives according to the present invention were added to a liquid crystal composition Q containing conventional thiadiazole compounds to provide a ferroelectric liquid crystal composition P of the invention, which showed improved response speed at a lower temperature and also decreased temperature-dependence of response speed.

EXAMPLE 18

A liquid crystal composition R was prepared in the same manner as in Example 11 except that the following Example Compounds were used instead of Example Compounds Nos. I-3, I-13 and I-72 in the respectively indicated proportions.

| Ex. Comp. No. | Structural formula | wt. parts |
|---|---|---|
| I-72 | $C_6H_{13}$—⟨phenyl⟩—(thiadiazole N—N/S)—⟨phenyl, F⟩—$OC_6H_{13}$ | 2 |
| I-113 | $C_8H_{17}$—⟨phenyl⟩—(thiadiazole N—N/S)—⟨phenyl, F⟩—$OCC_6H_{13}$ (C=O) | 3 |
| 249 | $C_6H_{13}$—⟨phenyl⟩—(thiadiazole N—N/S)—⟨phenyl⟩—$OCC_7H_{15}$ (C=O) | 2 |
| 252 | $C_7H_{15}O$—⟨phenyl⟩—(thiadiazole N—N/S)—⟨cyclohexyl H⟩—$C_4H_9$ | 3 |

| Ex. Comp. No. | Structural formula | wt. parts |
|---|---|---|
| | Composition H | 90 |

A ferroelectric liquid crystal device was prepared in the same manner as in Example 6 except for using the composition R. The ferroelectric liquid crystal device was subjected to measurement of response time in the same manner as in Example 6, whereby the following results were obtained.

| | 15° C. | 25° C. | 35° C. |
|---|---|---|---|
| Response time (μsec) | 132 | 96 | 81 |

COMPARATIVE EXAMPLE 18

A liquid crystal composition S was prepared in the same manner as in Example 18 except that the following Example Compounds were used instead of Example Compounds Nos. I-72, I-113, 249 and 252 in the respectively indicated proportions.

| Ex. Comp. No. | Structural formula | wt. parts |
|---|---|---|
| 249 | $C_6H_{13}$—⟨phenyl⟩—(N=N, S thiadiazole)—⟨phenyl⟩—$OCC_7H_{15}$ (C=O) | 2 |
| 252 | $C_7H_{15}O$—⟨phenyl⟩—(N=N, S thiadiazole)—⟨cyclohexyl H⟩—$C_4H_9$ | 3 |
| | Composition H | 90 |

A ferroelectric liquid crystal device was prepared in the same manner as in Example 6 except for using the composition S. The ferroelectric liquid crystal device was subjected to measurement of response time in the same manner as in Example 6, whereby the following results were obtained.

| | 15° C. | 25° C. | 35° C. |
|---|---|---|---|
| Response time (μsec) | 146 | 99 | 83 |

As is apparent from the above Example 18 and Comparative Example 18, 4-substituted-3-fluorophenyl-thiadiazole derivatives according to the present invention were added to a liquid crystal composition S containing conventional thiadiazole compounds to provide a ferroelectric liquid crystal composition R of the invention, which showed improved response speed at a lower temperature and also decreased temperature-dependence of response speed.

EXAMPLE 19

A liquid crystal composition T was prepared in the same manner as in Example 7 except that the following Example Compounds were used instead of Example Compounds Nos. I-4, I-16 and I-23 in respectively indicated proportions.

| Ex. Comp. No. | Structural formula | wt. parts |
|---|---|---|
| I-84 | $C_{10}H_{21}$—⟨phenyl⟩—(N=N, S thiadiazole)—⟨phenyl-F⟩—$OC_8H_{17}$ | 2 |
| I-105 | $C_6H_{13}$—⟨phenyl⟩—(N=N, S thiadiazole)—⟨phenyl-F⟩—$OCC_6H_{13}$ (C=O) | 3 |
| 245 | $C_6H_{13}$—⟨phenyl⟩—(N=N, S thiadiazole)—⟨phenyl⟩—$C_8H_{17}$ | 2 |
| 246 | $C_{10}H_{21}O$—⟨phenyl⟩—(N=N, S thiadiazole)—⟨phenyl⟩—$C_9H_{19}$ | 3 |

| Ex. Comp. No. | Structural formula | wt. parts |
|---|---|---|
| | Composition C | 90 |

A ferroelectric liquid crystal device was prepared in the same manner as in Example 6 except for using the composition T. The ferroelectric liquid crystal device was subjected to measurement of response time in the same manner as in Example 6, whereby the following results were obtained.

| | 15° C. | 25° C. | 35° C. |
|---|---|---|---|
| Response time (μsec) | 319 | 221 | 181 |

COMPARATIVE EXAMPLE 19

A liquid crystal composition U was prepared in the same manner as in Example 19 except that the following Example Compounds were used instead of Example Compounds Nos. I-84, I-105, 245 and 246 in the respectively indicated proportions.

| | 15° C. | 25° C. | 35° C. |
|---|---|---|---|
| Response time (μsec) | 334 | 220 | 173 |

As is apparent from the above Example 19 and Comparative Example 19, 4-substituted-3-fluorophenylthiadiazole derivatives according to the present invention were added to a liquid crystal composition U containing conventional thiadiazole compounds to provide a ferroelectric liquid crystal composition T containing 4-substituted-3-fluorophenylthiadiazole derivatives of the invention, which showed improved response speed at a lower temperature and also decreased temperature-dependence of response speed compared with that containing 4-substituted-2-fluorophenylthiadiazole derivatives.

| Ex. Comp. No. | Structural formula | wt. parts |
|---|---|---|
| | $C_6H_{13}$—〇—(N—N, S thiadiazole)—〇(F)—$OC_5H_{11}$ | 2 |
| | $C_8H_{17}$—〇—(N—N, S thiadiazole)—〇(F)—$OCC_6H_{13}$(=O) | 3 |
| 245 | $C_6H_{13}$—〇—(N—N, S thiadiazole)—〇—$C_8H_{17}$ | 2 |
| 246 | $C_{10}H_{21}O$—〇—(N—N, S thiadiazole)—〇—$C_9H_{19}$ | 3 |
| | Composition C | 90 |

A ferroelectric liquid crystal device was prepared in the same manner as in Example 6 except for using the composition U. The ferroelectric liquid crystal device was subjected to measurement of response time in the same manner as in Example 6, whereby the following results were obtained.

EXAMPLE 20

A liquid crystal composition V was prepared in the same manner as in Example 11 except that the following Example Compounds were used instead of Example Compounds Nos. I-3, I-13 and I-72 in the respectively indicated proportions.

| Ex. Comp. No. | Structural formula | wt. parts |
|---|---|---|
| I-45 | $C_5H_{11}$—〇—(N—N, S thiadiazole)—〇(F)—$C_8H_{17}$ | 2 |

| Ex. Comp. No. | Structural formula | wt. parts |
|---|---|---|
| I-78 | C$_8$H$_{17}$—⌬—[N—N/S]—(F)⌬—OC$_8$H$_{17}$ | 3 |
| 248 | C$_7$H$_{15}$O—⌬—[N—N/S]—⌬(H)—C$_5$H$_{11}$ | 2 |
| 251 | C$_6$H$_{13}$—⌬—[N—N/S]—⌬—OC$_8$H$_{17}$ | 3 |
| Composition H | | 90 |

A ferroelectric liquid crystal device was prepared in the same manner as in Example 6 except for using the composition V. The ferroelectric liquid crystal device was subjected to measurement of response time in the same manner as in Example 6, whereby the following results were obtained.

|  | 15° C. | 25° C. | 35° C. |
|---|---|---|---|
| Response time (μsec) | 128 | 95 | 81 |

COMPARATIVE EXAMPLE 20

A liquid crystal composition W was prepared in the same manner as in Example 20 except that the following Example Compounds were used instead of Example Compounds Nos. I-3, I-13 and I-72 in the respectively indicated proportions.

| Ex. Comp. No. | Structural formula | wt. parts |
|---|---|---|
|  | C$_5$H$_{11}$—⌬—[N—N/S]—(F)⌬—C$_4$H$_9$ | 2 |
|  | C$_8$H$_{17}$O—⌬—[N—N/S]—(F)⌬—OC$_6$H$_{13}$ | 3 |
| 248 | C$_7$H$_{15}$O—⌬—[N—N/S]—⌬(H)—C$_5$H$_{11}$ | 2 |
| 251 | C$_6$H$_{13}$—⌬—[N—N/S]—⌬—OC$_8$H$_{17}$ | 3 |
| Composition H | | 90 |

A ferroelectric liquid crystal device was prepared in the same manner as in Example 6 except for using the composition W. The ferroelectric liquid crystal device was subjected to measurement of response time in the same manner as in Example 6, whereby the following results were obtained.

|  | 15° C. | 25° C. | 35° C. |
|---|---|---|---|
| Response time (μsec) | 135 | 87 | 75 |

As is apparent from the above Example 20 and Comparative Example 20, 4-substituted-3-fluorophenylthiadiazole derivatives according to the present invention were added to a liquid crystal composition W containing conventional thiadiazole compounds to provide a ferroelectric liquid crystal composition V containing 4-substituted-3-fluorophenylthiadiazole derivatives of the invention, which showed improved response speed at a lower temperature and also decreased temperature-dependence of response speed compared with that containing 4-substituted-2-fluorophenylthiadiazole derivatives.

EXAMPLE 21

A blank cell was prepared in the same manner as in Example 7 by using a 2% aqueous solution of polyvinyl alcohol resin (PVA-117, available from Kuraray K.K.) instead of the 1.5%-solution of polyimide resin precursor in dimethylacetoamide on each electrode plate. A ferroelectric liquid crystal device was prepared by filling the blank cell with the liquid crystal composition D prepared in Example 7. The liquid crystal device was subjected to measurement of optical response time in the same manner as in Example 7. The results are shown below.

|  | 15° C. | 25° C. | 35° C. |
| --- | --- | --- | --- |
| Response time (μsec) | 298 | 201 | 164 |

EXAMPLE 22

A blank cell was prepared in the same manner as in Example 7 except for omitting the $SiO_2$ layer to form an alignment control layer composed of the polyimide resin layer alone on each electrode plate. A ferroelectric liquid crystal device was prepared by filling the blank cell with the liquid crystal composition D prepared in Example 7. The liquid crystal device was subjected to measurement of optical response time in the same manner as in Example 7. The results are shown below.

|  | 15° C. | 25° C. | 35° C. |
| --- | --- | --- | --- |
| Response time (μsec) | 291 | 196 | 157 |

As is apparent from the above Examples 21 and 22, also in the cases of different device structures, the devices containing the ferroelectric liquid crystal composition D according to the present invention respectively provided a remarkably improved operation characteristic at a lower temperature and also a decreased temperature-dependence of the response speed similar to those in Example 7.

EXAMPLE 23

2-decyl-5-(3-fluoro-4-pentanoyloxyphenyl)-1,3,4-thiadiazole (Example Compound No. I-220) was synthesized through the following steps i) to v).

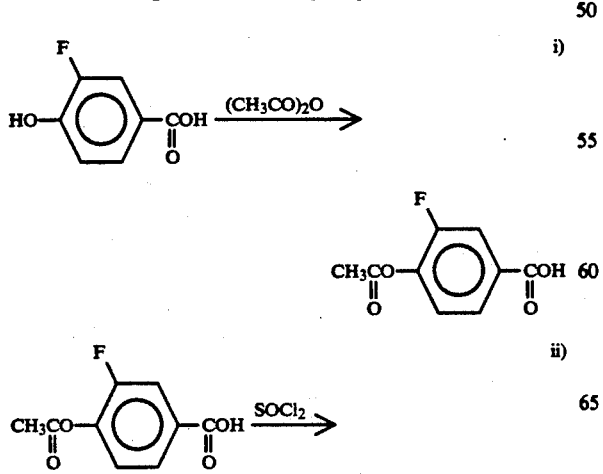

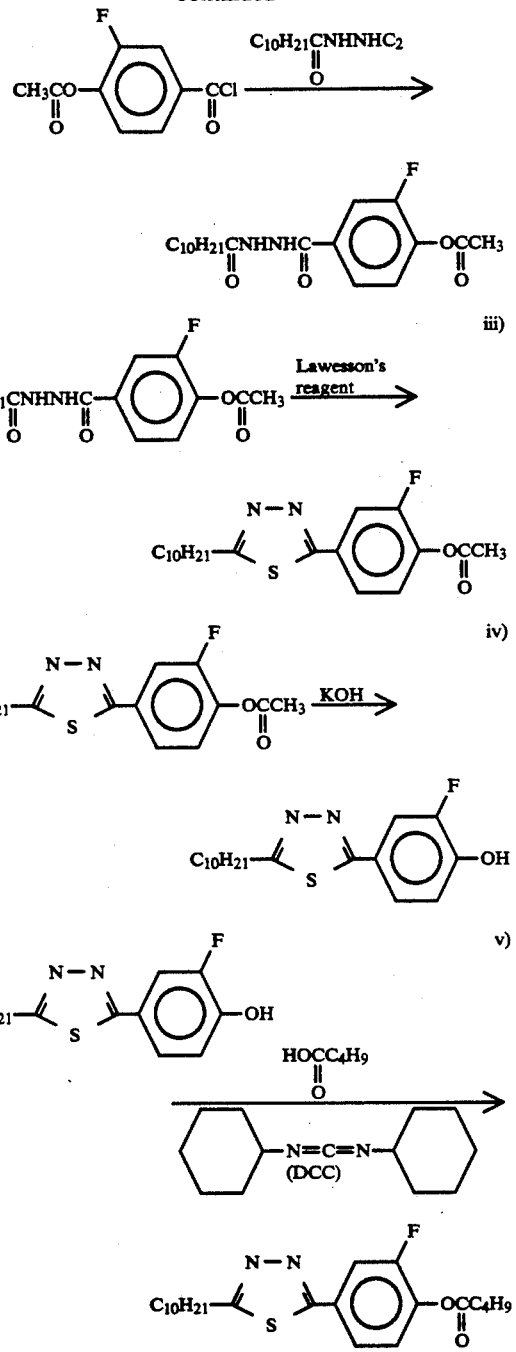

Step i) Production of 4-acetoxy-3-fluorobenzoic acid 6.40 ml of acetic anhydride was added to 5.00 g (32.00 mM) of 3-fluoro-4-hydroxybenzoic acid. Under stirring at room temperature, two drops of concentrated sulfuric acid was added thereto (the mixture solidified as soon as the concentrated sulfuric acid was added), followed by heat-stirring for 10 minutes at 107°–111° C. on an oil bath (the mixture became transparent and melted by heating). After the reaction, the reaction mixture was poured into 150 ml of iced water to precipitate a crystal. The crystal was recovered by filtration and recrystallized from 20 ml of methanol to obtain 5.04 g of 4-acetoxy-3-fluorobenzoic acid (Yield: 79.4%).

Step ii) Production of N-undecanoyl-N'-(4-acetoxy-3-fluorobenzo)hydrazide 2.90 ml of thionyl chloride was added to 2.50 g (12.6 mM) of 4-acetoxy-3-fluorobenzoic acid. Under stirring at room temperature, two drops of N,N-dimethylformamide (DMF) was added thereto, followed by refluxing for 40 minutes. After the reaction, dry benzene was added to the reaction mixture, followed by two times of distilling-off of excessive thionyl chloride under reduced pressure to obtain 4-acetoxy-3-fluorobenzoyl chloride.

A solution of the above-prepared 4-acetoxy-3-fluorobenzoyl chloride in 10 ml of dioxane was added to a solution of 2.40 g (12.0 mM) of undecanoylhydrazide in 20 ml of dioxane. Under stirring at about 80° C., 4.3 ml of pyridine was added thereto, followed by stirring for 40 minutes at about 80° C. After the reaction, the reaction mixture was poured into about 150 ml of iced water and common salt was added thereto, followed by stirring at room temperature to precipitate a crystal. The crystal was recovered by filtration and washed with water, followed by recrystallization from acetone to obtain 3.87 g of N-undecanoyl-N'-(4-acetoxy-3-fluorobenzo)hydrazide (Yield: 84.9%).

Step iii) Production of 2-decyl-5-(4-acetoxy-3-fluorophenyl)-1,3,4-thiadiazole 60 ml of tetrahydrofuran (THF) was added to a mixture of 3.80 g (9.99 mM) of N-undecanoyl-N'-(4-acetoxy-3-fluorobenzo)hydrazide and 4.30 g (10.6 mM) of Lawesson's reagent, followed by refluxing for 40 minutes under stirring. After the reaction, the reaction mixture was poured into a solution of 3.19 g of sodium hydroxide in 300 ml of iced water, followed by addition of common salt and stirring at room temperature to precipitate a crystal. The crystal was recovered by filtration and washed with water, followed by recrystallization from about 100 ml of methanol to obtain 3.39 g (wet) of 2-decyl-5-(4-acetoxy-3-fluorophenyl)-1,3,4-thiadiazole.

Step iv) Production of 2-decyl-5-(3-fluoro-4-hydroxyphenyl)-1,3,4-thiadiazole 1.59 g (24.1 mM) of 85%-potassium hydroxide was dissolved in 50 ml of ethanol on an oil bath (bath temperature: about 70° C.). To the solution, 3.37 g (wet, 8.90 mM) of 2-decyl-5-(4-acetoxy-3-fluorophenyl)-1,3,4-thiadiazole was added, followed by stirring for 10 minutes at about 70° C. After the reaction, the reaction mixture was poured into iced water, followed by filtration under reduced pressure. The filtrate was condensed, followed by successive addition of about 100 ml of water, 2.3 ml of concentrated sulfuric acid and common salt and stirring at room temperature to precipitate a crystal. The crystal was dissolved in ethyl acetate and dried with anhydrous sodium sulfuric acid. The sodium sulfuric acid was recovered by filtration and the filtrate was condensed into a solid; n-hexane was added to the solid and stirred at room temperature, followed by filtration to obtain 2.78 g of 2-decyl-5-(3-fluoro-4-hydroxyphenyl)-1,3,4-thiadiazole (Yield: 92.8%, Yield through the steps iii) and iv): 82.7%).

Step v) Production of 2-decyl-5-(3-fluoro-4-pentanoyloxyphenyl)-1,3,4-thiadiazole 40 ml of dichloromethane was added to a mixture of 2.0 g (5.94 mM) of 2-decyl-5-(3-fluoro-4-hydroxyphenyl)-1,3,4-thiadiazole and 0.61 g (5.97 mM) of pentanoic acid. Under stirring at room temperature, 1.21 g (5.86 mM) of N,N'-dicyclohexylcarbodiimide (DCC) and 0.05 g of 4-pyrrolidinopyridine were successively added to the above mixture, followed by stirring for 19 hours at room temperature. After the reaction, precipitated N,N'-dicyclohexylurea was recovered by filtration, washed with dichloromethane and added to the filtrate. The resultant dichloromethane solution was subjected to distillation under reduced pressure to obtain a residue. The residue was purified by silica gel column chromatography (eluent: benzene) and recrystallized from ethanol to obtain 1.40 g of 2-decyl-5-(3-fluoro-4-pentanoyloxyphenyl)-1,3,4-thiadiazole (Yield: 56.9%).

Phase transition temperature (°C.)

Cryst. —56→ Iso.
30 ↖ ↗ 53
  Sm1

Sm1: smectic phase (unidentified) other than SmC and SmA.

EXAMPLES 24-28

Mesomorphic compounds were synthesized in the same manner as in Example 23, respectively. The results are shown below.

| Ex. No. | Ex. Comp. No. | Structural Formula | Phase transition temp. (°C.) |
|---|---|---|---|
| 24 | I-221 | | Cryst. —61→ Iso. 44 ↖↗ 58 Sm1 |
| 25 | I-222 | | Cryst. —65→ Iso. 51 ↖↗ 59 Sm1 |

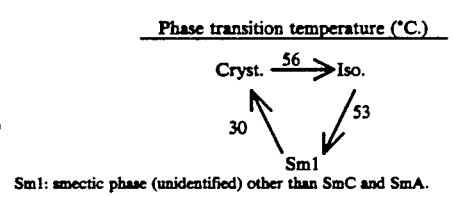

-continued

| Ex. No. | Ex. Comp. No. | Structural Formula | Phase transition temp. (°C.) |
|---|---|---|---|
| 26 | I-223 | $C_{10}H_{21}-\underset{S}{\overset{N-N}{\diagup}}-\underset{}{\bigcirc}-\overset{F}{\underset{}{}}-OCC_7H_{15}$ (C=O) | Cryst. $\xrightarrow{68}$ Iso. ↖53 ↙63 Sm1 |
| 27 | I-224 | $C_{10}H_{21}-\underset{S}{\overset{N-N}{\diagup}}-\underset{}{\bigcirc}-\overset{F}{\underset{}{}}-OCC_8H_{17}$ (C=O) | Cryst. $\xrightarrow{66}$ Iso. ↖50 ↙64 Sm1 |
| 28 | I-225 | $C_{10}H_{21}-\underset{S}{\overset{N-N}{\diagup}}-\underset{}{\bigcirc}-\overset{F}{\underset{}{}}-OC(CH_2)_2CH(CH_3)CHCH_3$ | Cryst. $\xrightarrow{60}$ Iso. 34 ↖ ↙52 Sm2 $\xleftarrow{44}$ Sm1 |

Sm2: smectic phase (unidentified) other than SmC and SmA.

As described hereinabove, the present invention provides a liquid crystal device which shows a good switching characteristic, an improved operation characteristic at a lower temperature and a decreased temperature dependence of response speed. Further, the present invention provides a mesomorphic compound and a liquid crystal composition useful for providing such a liquid crystal device.

What is claimed is:

1. A mesomorphic compound represented by the following formula (I):

$$R_1 +\!\!\fbox{A}\!\!+_n \overset{N-N}{\underset{S}{\diagup}} -\!\!\bigcirc\!\!-\overset{F}{}\!-R_2, \quad (I)$$

wherein $R_1$ and $R_2$ respectively denote a linear or branched alkyl group having 1-18 carbon atoms capable of including one or non-neighboring two or more methylene groups which can be replaced with at least one species of —O—, —S—, —CO—, —COO—, —OCO— and —OCOO—;

$-\fbox{A}-$ denotes $-\bigcirc-$ or $-\fbox{H}-$ and n is 0 or 1.

2. A mesomorphic compound according to claim 1, wherein $R_1$ and $R_2$ are represented by any one of the following combinations (i) to (vi):

(i) $R_1$ is n—$C_mH_{2m+1}$—$X_1$— and $R_2$ is n—$C_lH_{2l+1}$—$X_2$—;

(ii) $R_1$ is n—$C_mH_{2m+1}$—$X_1$— and $R_2$ is $$R_3CH(CH_3)(CH_2)_pX_2—;$$

(iii) $R_1$ is n—$C_mH_{2m+1}$—$X_1$— and $R_2$ is $$R_4O(CH_2)_qCH(CH_3)(CH_2)_rX_2—;$$

(iv) $R_1$ is $$R_5—CH(CH_3)(CH_2)_sX_1—$$

and $R_2$ is n—$C_mH_{2m+1}$—$X_2$—;

(v) $R_1$ is $$R_5—CH(CH_3)(CH_2)_sX_1—$$

and $R_2$ is $$R_3—CH(CH_3)(CH_2)_pX_2—;$$

and (vi) $R_1$ is $$R_5—CH(CH_3)(CH_2)_sX_1—$$

and $R_2$ is $$R_4—O(CH_2)_qCH(CH_3)(CH_2)_rX_2—,$$

wherein m and l respectively denote an integer of 1-17; p, r and s respectively denote an integer of 0-7; q is 0 or 1; $R_3$, $R_4$ and $R_5$ respectively denote a linear or branched alkyl group; and $X_1$ and $X_2$ respectively denote a single bond, —O—, $$-\underset{O}{\overset{\|}{OC}}—, \quad -\underset{O}{\overset{\|}{CO}}— \text{ or } -\underset{O}{\overset{\|}{OCO}}—$$

with the proviso that $X_1$ denotes a single bond when n is 0.

3. A mesomorphic compound according to claim 1, wherein

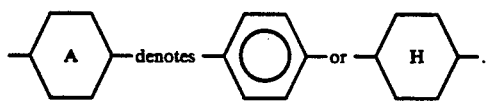

4. A mesomorphic compound according to claim 3, wherein

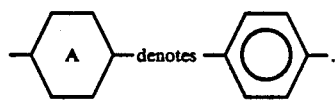

5. A compound according to claim 1, of the formula:

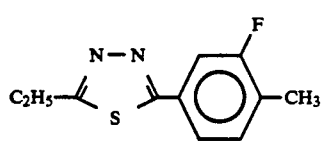

6. A compound according to claim 1, of the formula:

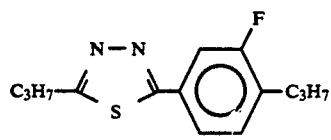

7. A compound according to claim 1, of the formula:

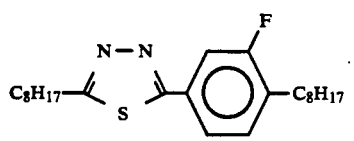

8. A compound according to claim 1, of the formula:

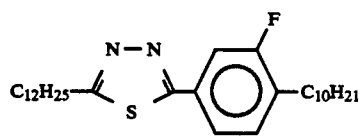

9. A compound according to claim 1, of the formula:

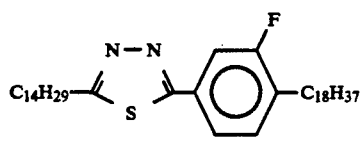

10. A compound according to claim 1, of the formula:

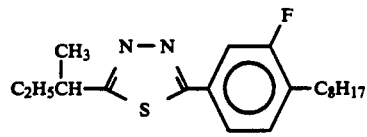

11. A compound according to claim 1, of the formula:

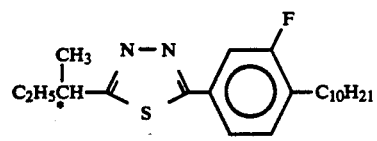

12. A compound according to claim 1, of the formula:

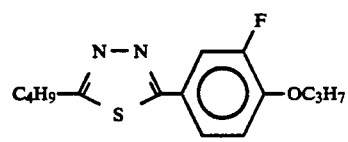

13. A compound according to claim 1, of the formula:

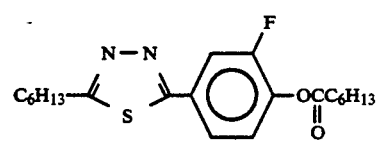

14. A compound according to claim 1, of the formula:

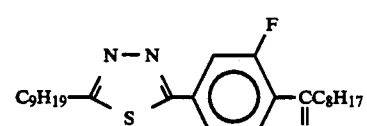

15. A compound according to claim 1, of the formula:

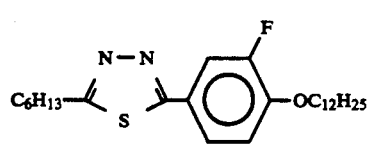

16. A compound according to claim 1, of the formula:

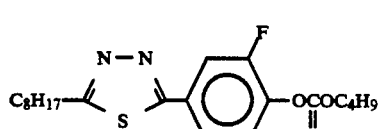

17. A compound according to claim 1, of the formula:

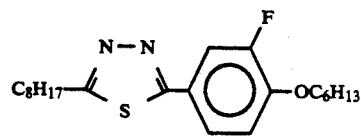

18. A compound according to claim 1, of the formula:

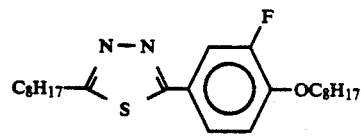

19. A compound according to claim 1, of the formula:

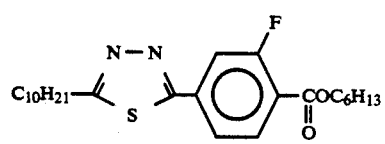

20. A compound according to claim 1, of the formula:

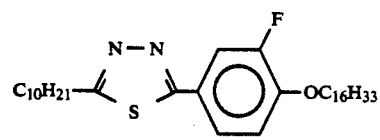

21. A compound according to claim 1, of the formula:

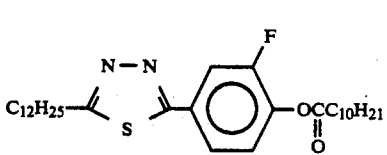

22. A compound according to claim 1, of the formula:

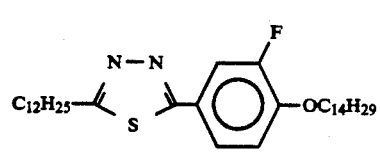

23. A compound according to claim 1, of the formula:

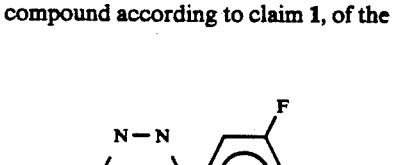

24. A compound according to claim 1, of the formula:

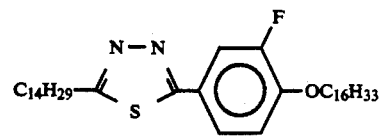

25. A compound according to claim 1, of the formula:

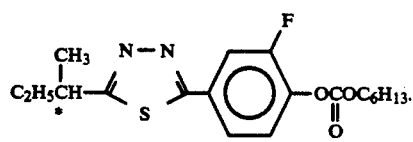

26. A compound according to claim 1, of the formula:

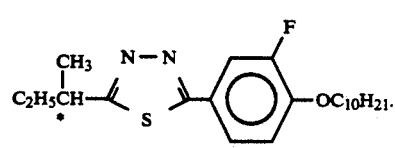

27. A compound according to claim 1, of the formula:

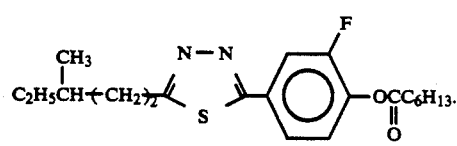

28. A compound according to claim 1, of the formula:

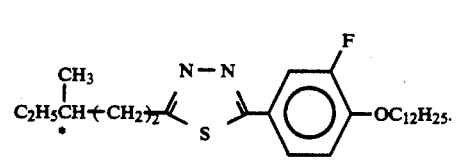

29. A compound according to claim 1, of the formula:

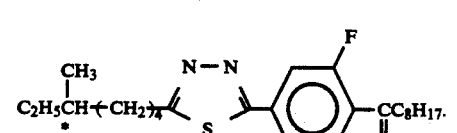

30. A compound according to claim 1, of the formula:

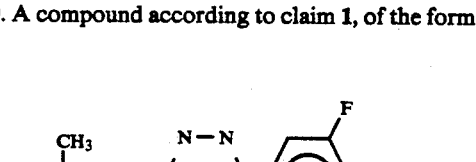

31. A compound according to claim 1, of the formula:

32. A compound according to claim 1, of the formula:

C₂H₅CH(CH₃)–(CH₂)₂–⟨N–N / S⟩–⟨C₆H₃(F)⟩–COOC₆H₁₃
       *
                ‖
                O

33. A compound according to claim 1, of the formula:

C₂H₅CH(CH₃)–(CH₂)₄–⟨N–N / S⟩–⟨C₆H₃(F)⟩–OC₁₂H₂₅
       *

34. A compound according to claim 1, of the formula:

C₆H₁₃–⟨N–N / S⟩–⟨C₆H₃(F)⟩–OCH(CH₃)C(O)C₂H₅

35. A compound according to claim 1, of the formula:

C₆H₁₃–⟨N–N / S⟩–⟨C₆H₃(F)⟩–O–(CH₂)₃CH(CH₃)C₂H₅
                                            *

36. A compound according to claim 1, of the formula:

C₁₀H₂₁–⟨N–N / S⟩–⟨C₆H₃(F)⟩–CO–(CH₂)₃CH(CH₃)C₂H₅
                              ‖                    *
                              O

37. A compound according to claim 1, of the formula:

C₆H₁₃–⟨N–N / S⟩–⟨C₆H₃(F)⟩–OCH₂CH(CH₃)OC₃H₇
                                        *

38. A compound according to claim 1, of the formula:

C₆H₁₃–⟨N–N / S⟩–⟨C₆H₃(F)⟩–OCH₂CH(CH₃)OC₆H₁₃
                                        *

39. A compound according to claim 1, of the formula:

C₈H₁₇–⟨N–N / S⟩–⟨C₆H₃(F)⟩–O–(CH₂)₃CH(CH₃)OC₃H₇
                                              *

40. A compound according to claim 1, of the formula:

C₁₂H₂₅–⟨N–N / S⟩–⟨C₆H₃(F)⟩–O–(CH₂)₃CH(CH₃)OC₅H₁₁
                                              *

41. A compound according to claim 1, of the formula:

C₁₂H₂₅–⟨N–N / S⟩–⟨C₆H₃(F)⟩–OCH₂CH(CH₃)CH₂OC₈H₁₇
                                  *

42. A compound according to claim 1, of the formula:

C₂H₅CH(CH₃)–⟨N–N / S⟩–⟨C₆H₃(F)⟩–O–(CH₂)₃CH(CH₃)C₂H₅
       *                                          *

43. A compound according to claim 1, of the formula:

C₂H₅CH(CH₃)–(CH₂)₂–⟨N–N / S⟩–⟨C₆H₃(F)⟩–O–(CH₂)₃CH(CH₃)OC₃H₇
       *                                              *

44. A compound according to claim 1, of the formula:

CH₃–⟨C₆H₄⟩–⟨N–N / S⟩–⟨C₆H₃(F)⟩–CH₃

45. A compound according to claim 1, of the formula:

C₂H₅–⟨C₆H₄⟩–⟨N–N / S⟩–⟨C₆H₃(F)⟩–C₃H₇

46. A compound according to claim 1, of the formula:

C₂H₅—⟨phenyl⟩—C(S)=N—N=C—⟨phenyl-F⟩—C₅H₁₁.

47. A compound according to claim 1, of the formula:

C₃H₇—⟨phenyl⟩—C(S)=N—N=C—⟨phenyl-F⟩—C₇H₁₅.

48. A compound according to claim 1, of the formula:

C₅H₁₁—⟨phenyl⟩—C(S)=N—N=C—⟨phenyl-F⟩—C₅H₁₁.

49. A compound according to claim 1, of the formula:

C₅H₁₁—⟨phenyl⟩—C(S)=N—N=C—⟨phenyl-F⟩—C₇H₁₅.

50. A compound according to claim 1, of the formula:

C₅H₁₁—⟨phenyl⟩—C(S)=N—N=C—⟨phenyl-F⟩—C₈H₁₇.

51. A compound according to claim 1, of the formula:

C₆H₁₃—⟨phenyl⟩—C(S)=N—N=C—⟨phenyl-F⟩—C₄H₉.

52. A compound according to claim 1, of the formula:

C₆H₁₃—⟨phenyl⟩—C(S)=N—N=C—⟨phenyl-F⟩—C₆H₁₃.

53. A compound according to claim 1, of the formula:

C₈H₁₇—⟨phenyl⟩—C(S)=N—N=C—⟨phenyl-F⟩—C₉H₁₉.

54. A compound according to claim 1, of the formula:

C₈H₁₇—⟨phenyl⟩—C(S)=N—N=C—⟨phenyl-F⟩—C₁₆H₃₃.

55. A compound according to claim 1, of the formula:

C₁₀H₂₁—⟨phenyl⟩—C(S)=N—N=C—⟨phenyl-F⟩—C₆H₁₃.

56. A compound according to claim 1, of the formula:

C₁₀H₂₁—⟨phenyl⟩—C(S)=N—N=C—⟨phenyl-F⟩—C₈H₁₇.

57. A compound according to claim 1, of the formula:

C₁₀H₂₁—⟨phenyl⟩—C(S)=N—N=C—⟨phenyl-F⟩—C₁₀H₂₁.

58. A compound according to claim 1, of the formula:

C₁₂H₂₅—⟨phenyl⟩—C(S)=N—N=C—⟨phenyl-F⟩—C₈H₁₇.

59. A compound according to claim 1, of the formula:

C₁₂H₂₅—⟨phenyl⟩—C(S)=N—N=C—⟨phenyl-F⟩—C₁₈H₃₇.

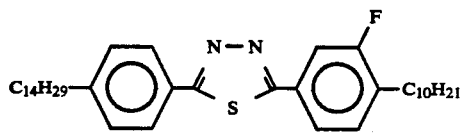

60. A compound according to claim 1, of the formula:

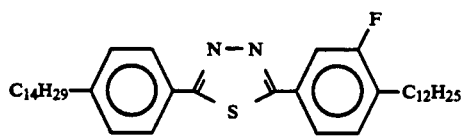

61. A compound according to claim 1, of the formula:

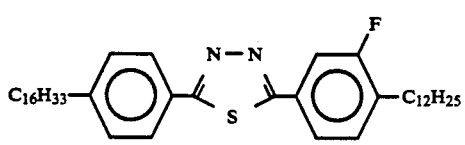

62. A compound according to claim 1, of the formula:

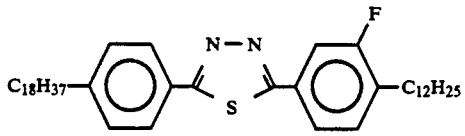

63. A compound according to claim 1, of the formula:

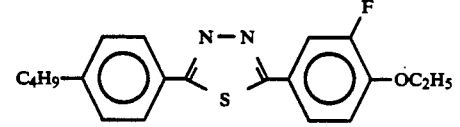

64. A compound according to claim 1, of the formula:

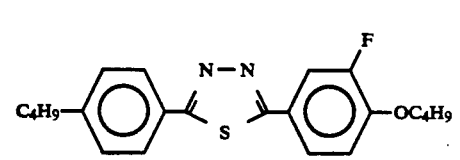

65. A compound according to claim 1, of the formula:

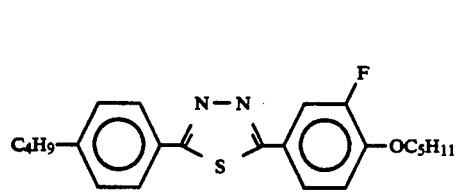

66. A compound according to claim 1, of the formula:

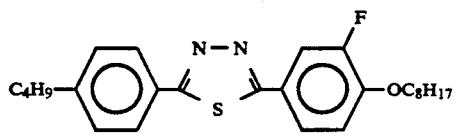

67. A compound according to claim 1, of the formula:

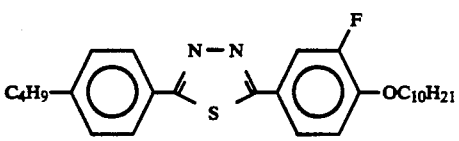

68. A compound according to claim 1, of the formula:

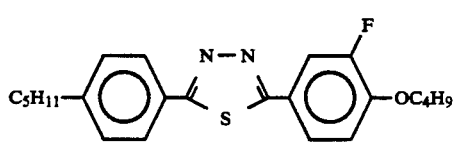

69. A compound according to claim 1, of the formula:

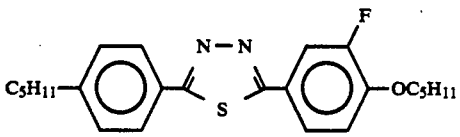

70. A compound according to claim 1, of the formula:

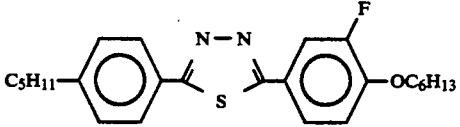

71. A compound according to claim 1, of the formula:

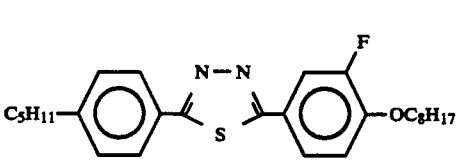

72. A compound according to claim 1, of the formula:

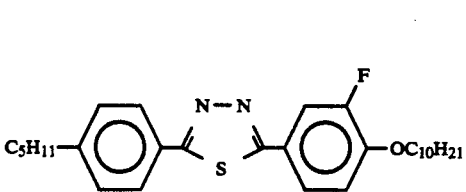

73. A compound according to claim 1, of the formula:

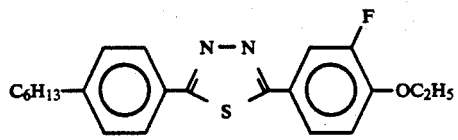

74. A compound according to claim 1, of the formula:

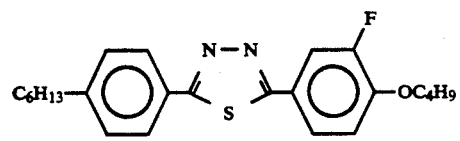

75. A compound according to claim 1, of the formula:

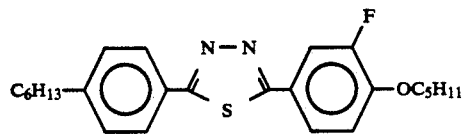

76. A compound according to claim 1, of the formula:

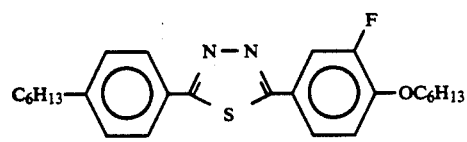

77. A compound according to claim 1, of the formula:

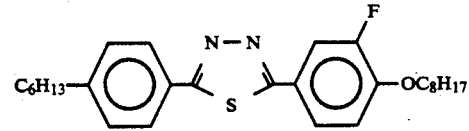

78. A compound according to claim 1, of the formula:

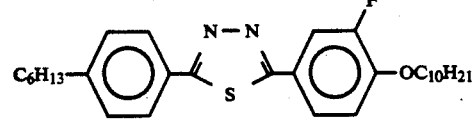

79. A compound according to claim 1, of the formula:

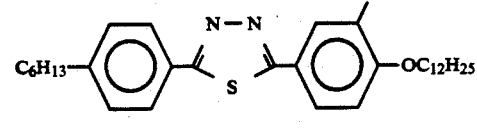

80. A compound according to claim 1, of the formula:

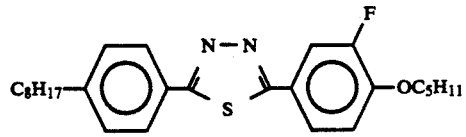

81. A compound according to claim 1, of the formula:

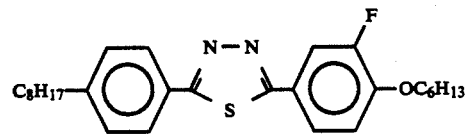

82. A compound according to claim 1, of the formula:

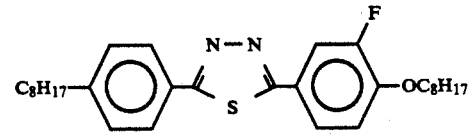

83. A compound according to claim 1, of the formula:

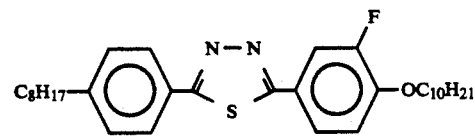

84. A compound according to claim 1, of the formula:

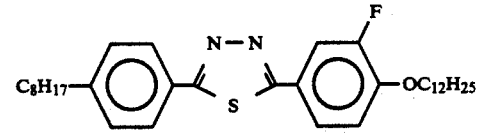

85. A compound according to claim 1, of the formula:

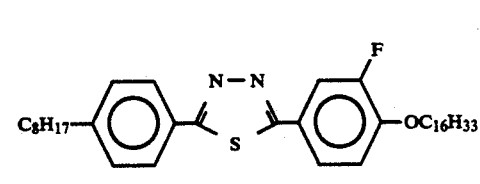

86. A compound according to claim 1, of the formula:

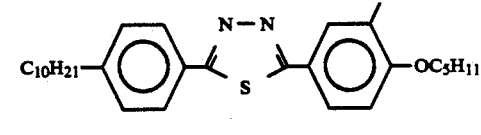

87. A compound according to claim 1, of the formula:

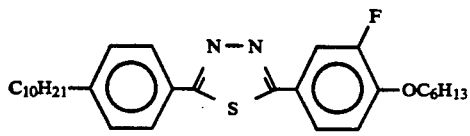

88. A compound according to claim 1, of the formula:

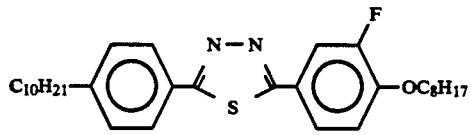

89. A compound according to claim 1, of the formula:

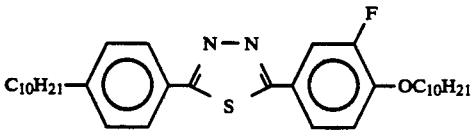

90. A compound according to claim 1, of the formula:

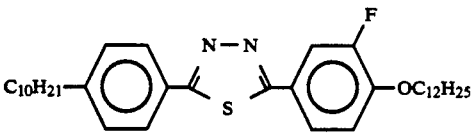

91. A compound according to claim 1, of the formula:

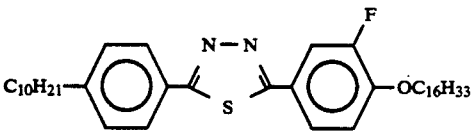

92. A compound according to claim 1, of the formula:

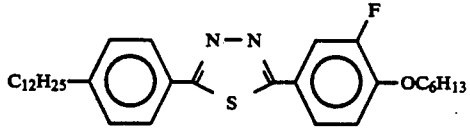

93. A compound according to claim 1, of the formula:

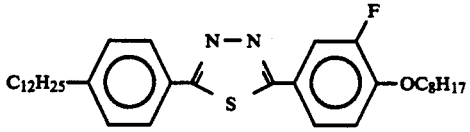

94. A compound according to claim 1, of the formula:

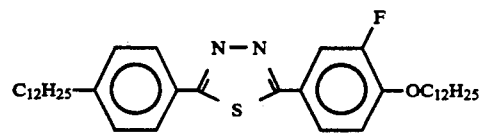

95. A compound according to claim 1, of the formula:

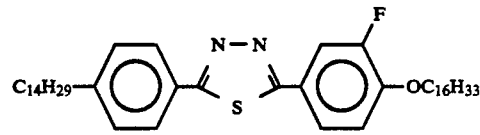

96. A compound according to claim 1, of the formula:

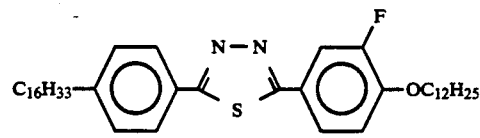

97. A compound according to claim 1, of the formula:

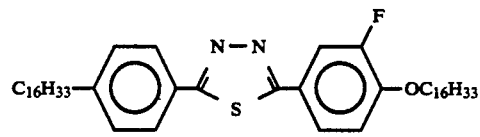

98. A compound according to claim 1, of the formula:

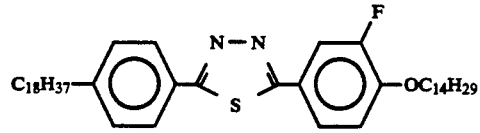

99. A compound according to claim 1, of the formula:

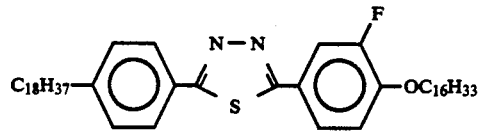

100. A compound according to claim 1, of the formula:

101. A compound according to claim 1, of the formula:

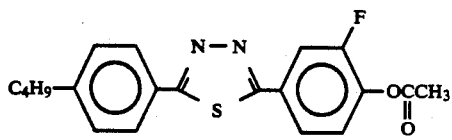

102. A compound according to claim 1, of the formula:

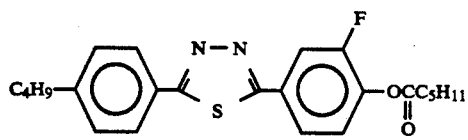

103. A compound according to claim 1, of the formula:

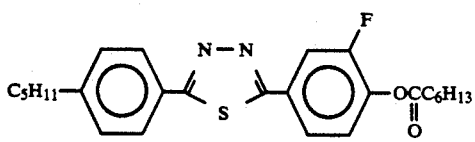

104. A compound according to claim 1, of the formula:

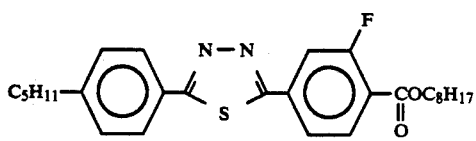

105. A compound according to claim 1, of the formula:

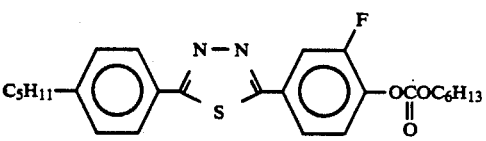

106. A compound according to claim 1, of the formula:

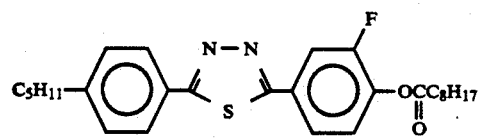

107. A compound according to claim 1, of the formula:

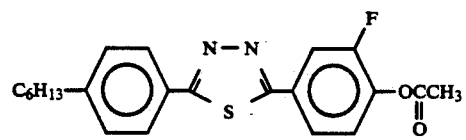

108. A compound according to claim 1, of the formula:

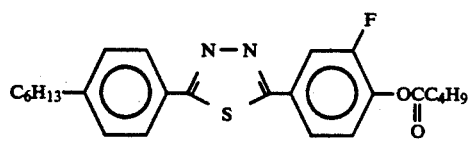

109. A compound according to claim 1, of the formula:

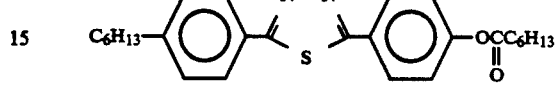

110. A compound according to claim 1, of the formula:

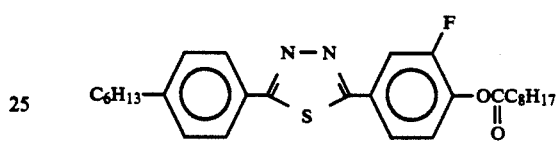

111. A compound according to claim 1, of the formula:

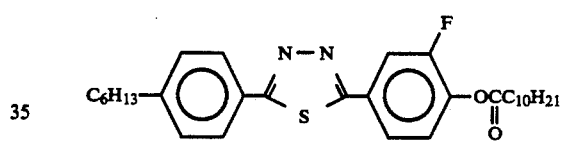

112. A compound according to claim 1, of the formula:

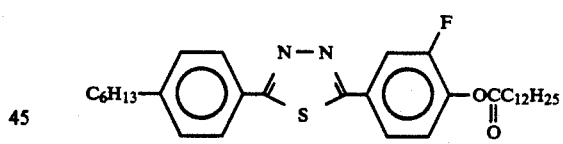

113. A compound according to claim 1, of the formula:

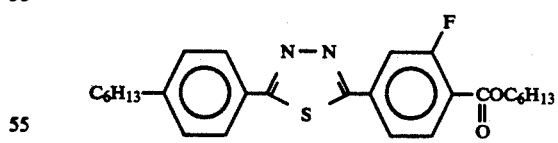

114. A compound according to claim 1, of the formula:

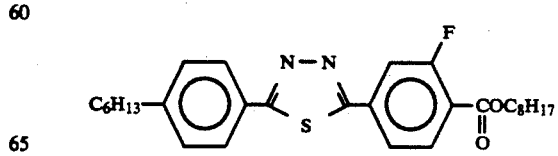

115. A compound according to claim 1, of the formula:

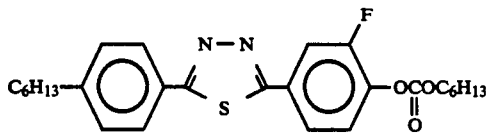

116. A compound according to claim 1, of the formula:

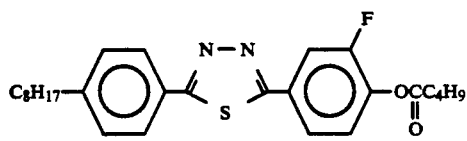

117. A compound according to claim 1, of the formula:

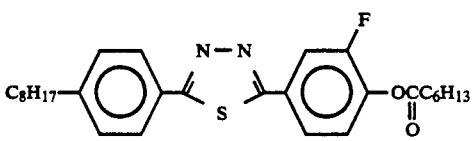

118. A compound according to claim 1, of the formula:

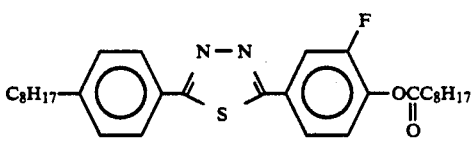

119. A compound according to claim 1, of the formula:

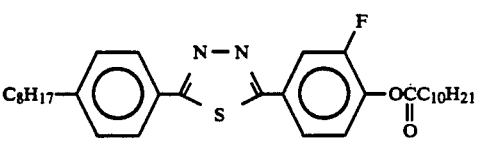

120. A compound according to claim 1, of the formula:

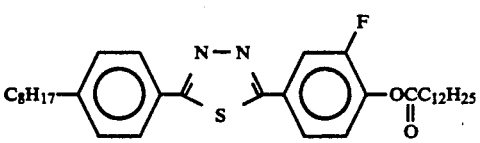

121. A compound according to claim 1, of the formula:

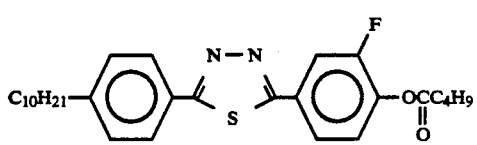

122. A compound according to claim 1, of the formula:

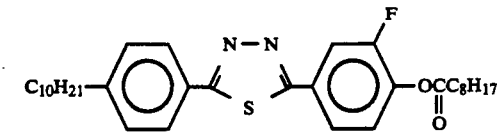

123. A compound according to claim 1, of the formula:

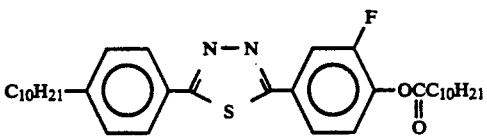

124. A compound according to claim 1, of the formula:

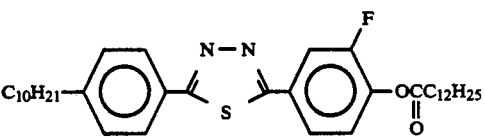

125. A compound according to claim 1, of the formula:

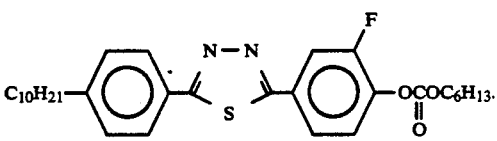

126. A compound according to claim 1, of the formula:

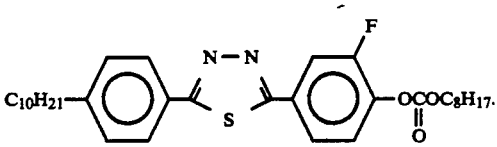

127. A compound according to claim 1, of the formula:

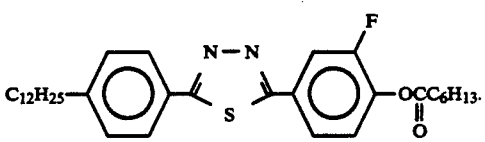

128. A compound according to claim 1, of the formula:

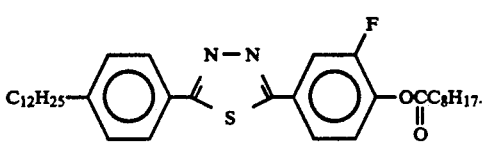

129. A compound according to claim 1, of the formula:

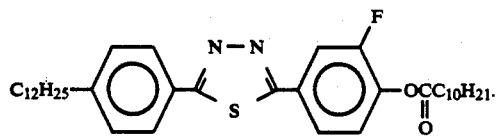

130. A compound according to claim 1, of the formula:

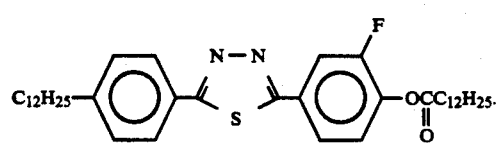

131. A compound according to claim 1, of the formula:

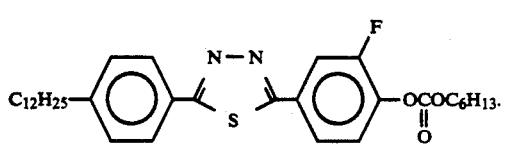

132. A compound according to claim 1, of the formula:

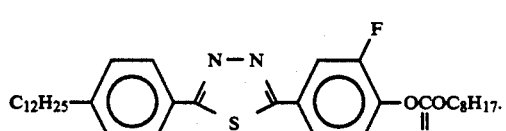

133. A compound according to claim 1, of the formula:

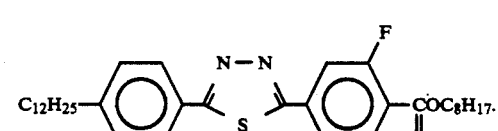

134. A compound according to claim 1, of the formula:

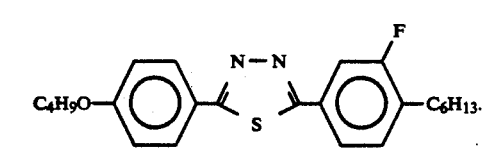

135. A compound according to claim 1, of the formula:

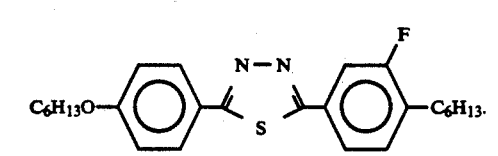

136. A compound according to claim 1, of the formula:

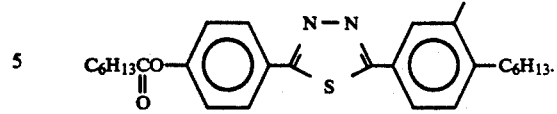

137. A compound according to claim 1, of the formula:

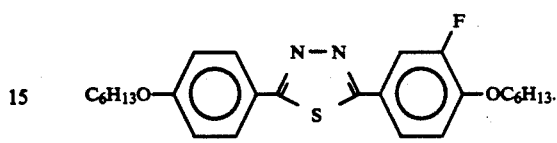

138. A compound according to claim 1, of the formula:

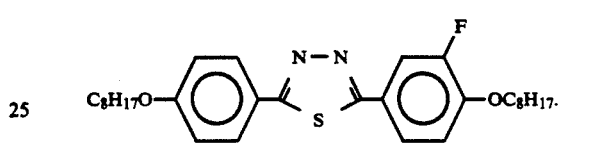

139. A compound according to claim 1, of the formula:

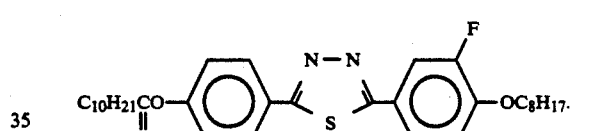

140. A compound according to claim 1, of the formula:

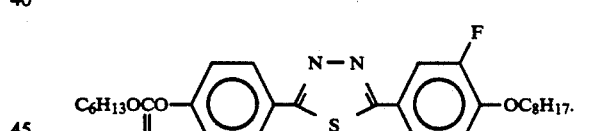

141. A compound according to claim 1, of the formula:

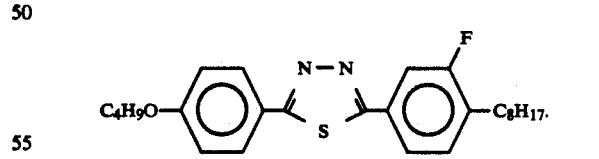

142. A compound according to claim 1, of the formula:

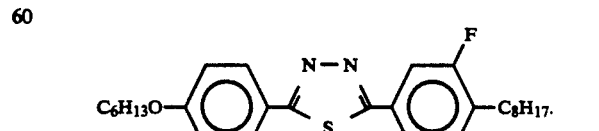

143. A compound according to claim 1, of the formula:

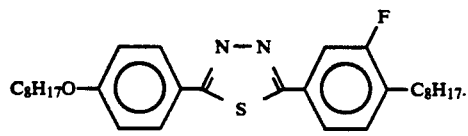

144. A compound according to claim 1, of the formula:

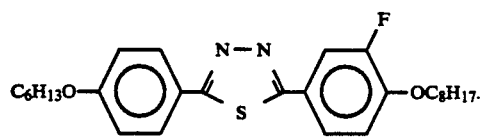

145. A compound according to claim 1, of the formula:

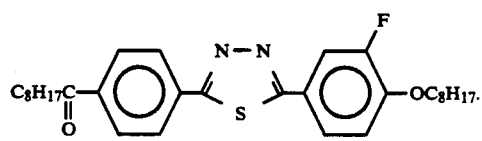

146. A compound according to claim 1, of the formula:

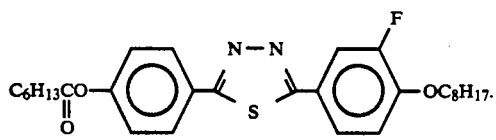

147. A compound according to claim 1, of the formula:

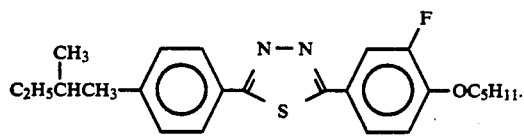

148. A compound according to claim 1, of the formula:

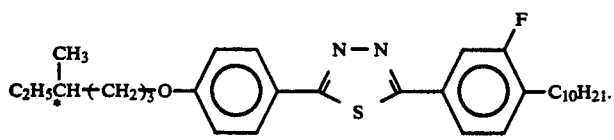

149. A compound according to claim 1, of the formula:

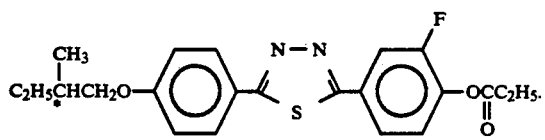

150. A compound according to claim 1, of the formula:

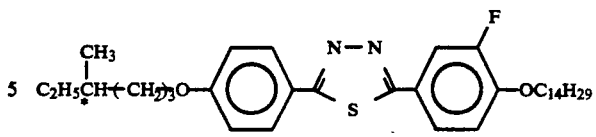

151. A compound according to claim 1, of the formula:

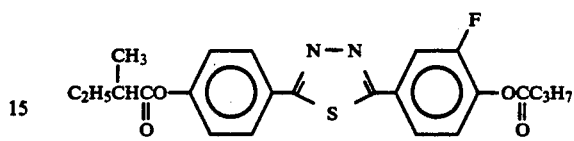

152. A compound according to claim 1, of the formula:

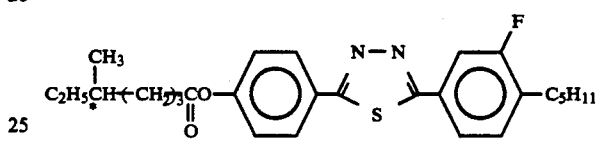

153. A compound according to claim 1, of the formula:

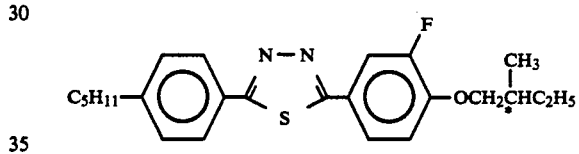

154. A compound according to claim 1, of the formula:

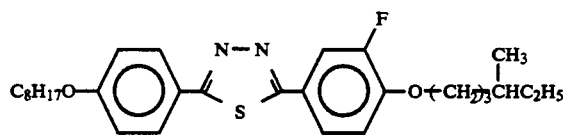

155. A compound according to claim 1, of the formula:

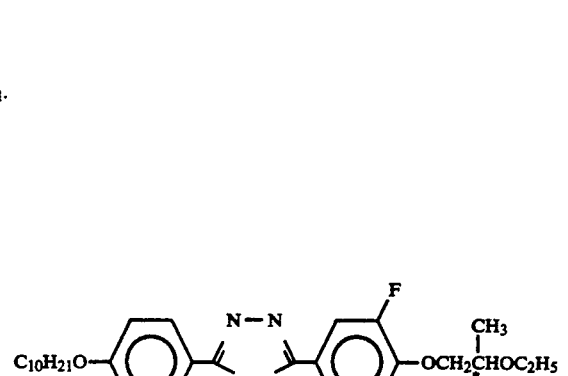

156. A compound according to claim 1, of the formula:

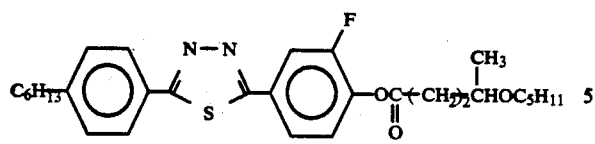

157. A compound according to claim 1, of the formula:

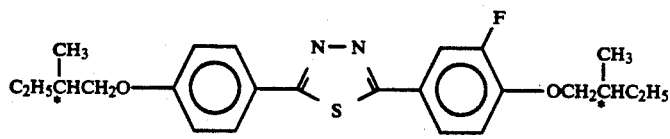

158. A compound according to claim 1, of the formula:

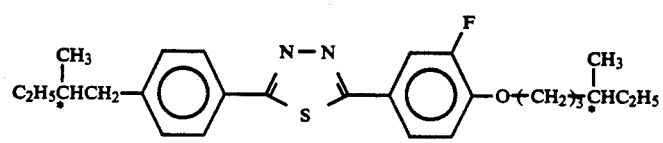

159. A compound according to claim 1, of the formula:

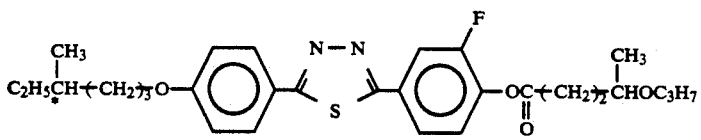

160. A compound according to claim 1, of the formula:

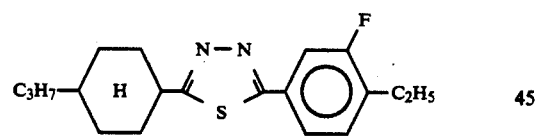

161. A compound according to claim 1, of the formula:

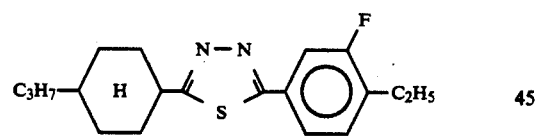

162. A compound according to claim 1, of the formula:

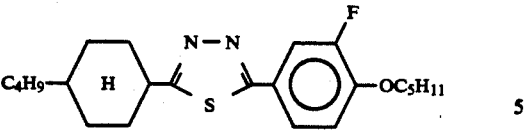

163. A compound according to claim 1, of the formula:

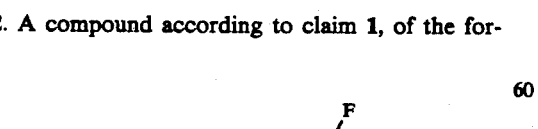

164. A compound according to claim 1, of the formula:

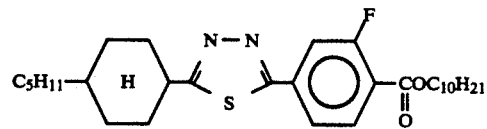

165. A compound according to claim 1, of the formula:

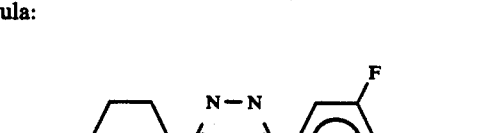

166. A compound according to claim 1, of the formula:

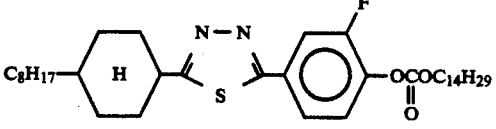

167. A compound according to claim 1, of the formula:

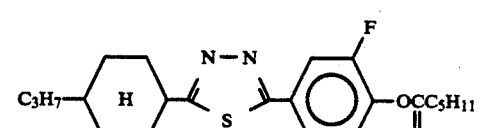

168. A compound according to claim 1, of the formula:

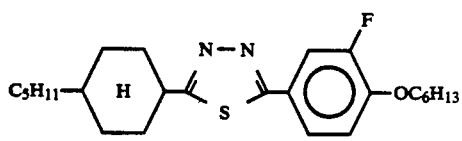

169. A compound according to claim 1, of the formula:

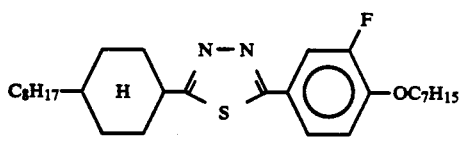

170. A compound according to claim 1, of the formula:

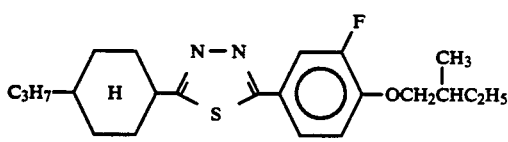

171. A compound according to claim 1, of the formula:

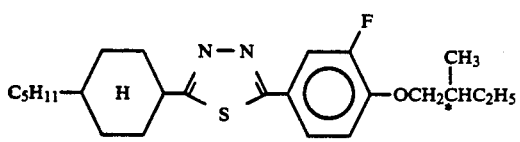

172. A compound according to claim 1, of the formula:

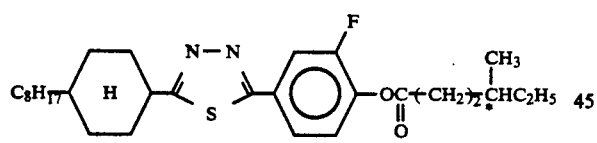

173. A compound according to claim 1, of the formula:

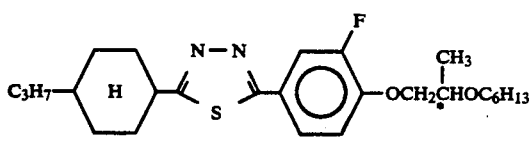

174. A compound according to claim 1, of the formula:

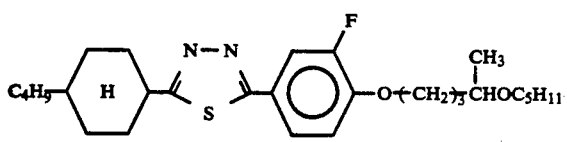

175. A compound according to claim 1, of the formula:

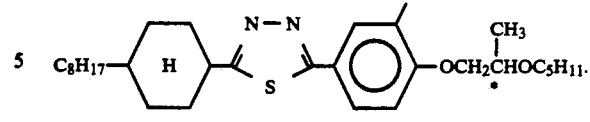

176. A compound according to claim 1, of the formula:

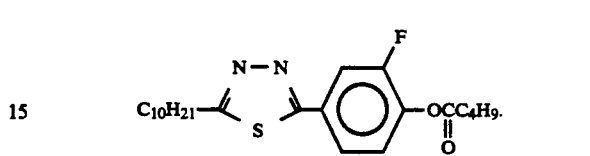

177. A compound according to claim 1, of the formula:

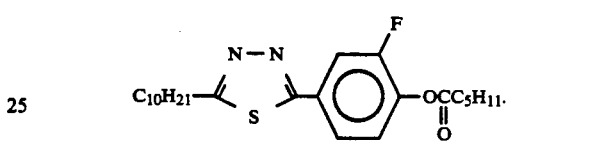

178. A compound according to claim 1, of the formula:

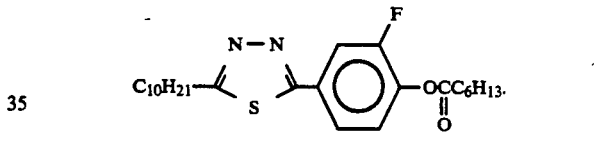

179. A compound according to claim 1, of the formula:

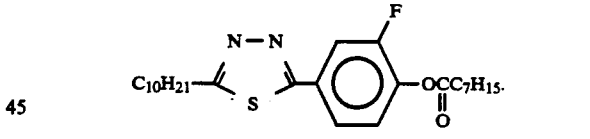

180. A compound according to claim 1, of the formula:

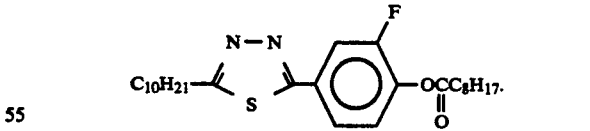

181. A compound according to claim 1, of the formula:

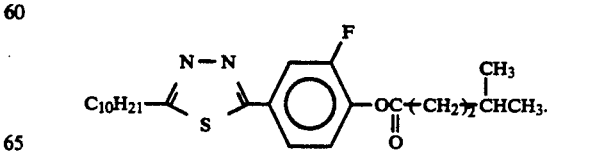

182. A compound according to claim 1, of the formula:

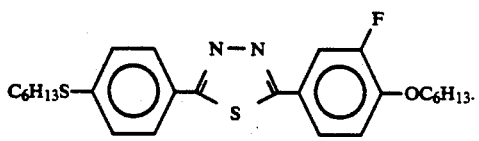

183. A compound according to claim 1, of the formula:

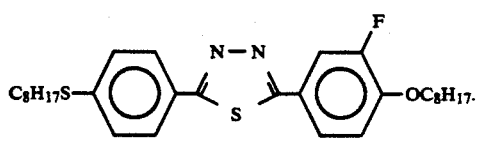

184. A compound according to claim 1, of the formula:

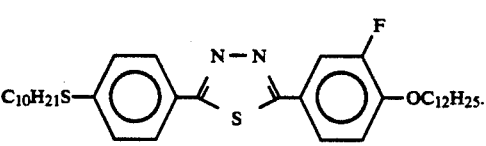

185. A compound according to claim 1, of the formula:

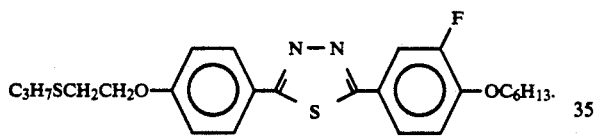

186. A compound according to claim 1, of the formula:

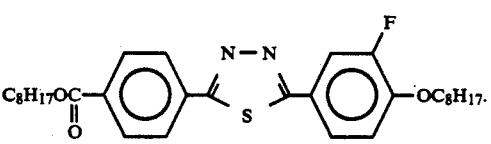

187. A compound according to claim 1, of the formula:

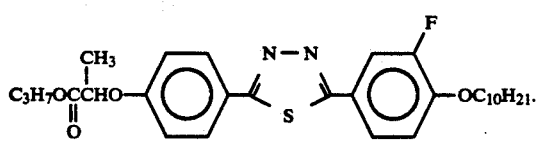

188. A compound according to claim 1, of the formula:

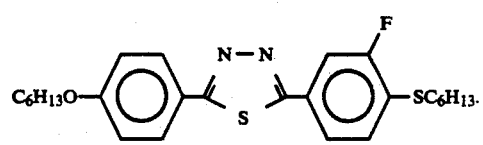

189. A compound according to claim 1, of the formula:

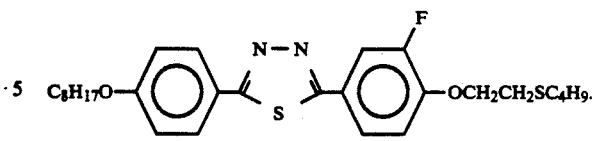

190. A liquid crystal composition comprising at least two mesomorphic compounds, at least one of which is a mesomorphic compound of the formula (I) according to claim 1.

191. A liquid crystal composition according to claim 190, which contains 1–85 wt. % of said mesomorphic compound of the formula (I).

192. A liquid crystal composition according to claim 191, which contains 1–40 wt. % of said mesomorphic compound of the formula (I).

193. A liquid crystal composition according to claim 190, which comprises a mesomorphic compound of the formula (I) wherein $R_1$ and $R_2$ are represented by any one of the following combinations (i) to (vi):

(i) $R_1$ is n—$C_mH_{2m+1}$—$X_1$— and $R_2$ is n—$C_lH_{2l+1}$—$X_2$—;

(ii) $R_1$ is n—$C_mH_{2m+1}$—$X_1$— and $R_2$ is

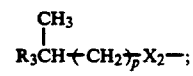

(iii) $R_1$ is n—$C_mH_{2m+1}$—$X_1$— and $R_2$ is

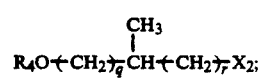

(iv) $R_1$ is

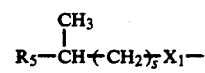

and $R_2$ is n—$C_mH_{2m+1}$—$X_2$—;

(v) $R_1$ is

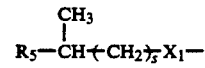

and $R_2$ is

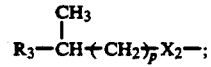

and (vi) $R_1$ is

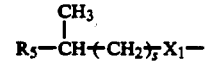

and $R_2$ is

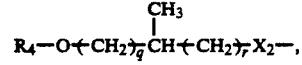

wherein m and l respectively denote an integer of 1-17; p, r and s respectively denote an integer of 0-7; q is 0 or 1; $R_3$, $R_4$ and $R_5$ respectively denote a linear or branched alkyl group; and $X_1$ and $X_2$ respectively denote a single bond, —O—,

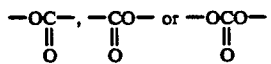

with the proviso that $X_1$ denotes a single bond when n is 0.

194. A liquid crystal composition according to claim 190, which comprises a mesomorphic compound of the formula (I) wherein

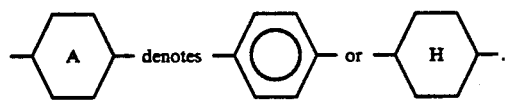

195. A liquid crystal composition according to claim 194, wherein

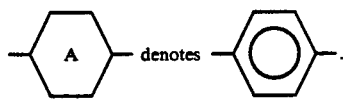

196. A liquid crystal device, comprising a pair of electrode plates and a liquid crystal composition according to claim 190 disposed between the electrode plates.

197. A liquid crystal device according to claim 196, wherein the liquid crystal composition comprises a mesomorphic compound of the formula (I) wherein $R_1$ and $R_2$ are represented by any one of the following combinations (i) to (vi):

(i) $R_1$ is n—$C_mH_{2m+1}$—$X_1$— and $R_2$ is n—$C_lH_{2l+1}$—$X_2$—;

(ii) $R_1$ is n—$C_mH_{2m+1}$—$X_1$— and $R_2$ is $$R_3CH(CH_2)_{\overline{p}}X_2—;$$
$$\qquad |\\ \quad CH_3$$

(iii) $R_1$ is n—$C_mH_{2m+1}$—$X_1$— and $R_2$ is $$R_4O(CH_2)_{\overline{q}}CH(CH_2)_{\overline{r}}X_2;$$
$$\qquad\qquad\quad |\\ \qquad\qquad CH_3$$

(iv) $R_1$ is

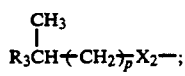

and $R_2$ is n—$C_mH_{2m+1}$—$X_2$—;

(v) $R_1$ is

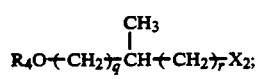

and $R_2$ is

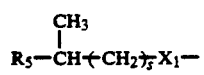

and
(vi) $R_1$ is

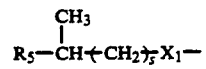

and $R_2$ is

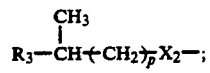

wherein m and l respectively denote an integer of 1-17; p, r and s respectively denote an integer of 0-7; q is 0 or 1; $R_3$, $R_4$ and $R_5$ respectively denote a linear or branched alkyl group; and $X_1$ and $X_2$ respectively denote a single bond, —O—,

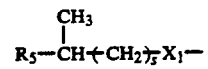

with the proviso that $X_1$ denotes a single bond when n is 0.

198. A liquid crystal device according to claim 196, wherein the liquid crystal composition comprises a mesomorphic compound of the formula (I) wherein

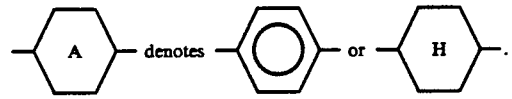

199. A liquid crystal device according to claim 198, wherein

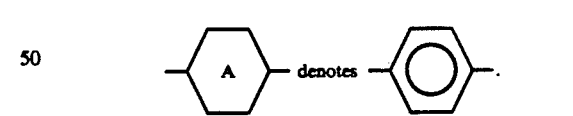

200. A liquid crystal device according to claim 196, wherein the liquid crystal composition contains 1-85 wt. % of said mesomorphic compound of the formula (I).

201. A liquid crystal device according to claim 200, wherein the liquid crystal composition contains 1-40 wt. % of said mesomorphic compound of the formula (I).

* * * * *

UNITED STATES PATENT AND TRADEMARK OFFICE
CERTIFICATE OF CORRECTION

PATENT NO. : 5,200,109

DATED : April 6, 1993

INVENTOR(S) : TAKASHI IWAKI, ET AL.

It is certified that error appears in the above-identified patent and that said Letters Patent is hereby corrected as shown below:

On title page,

<u>IN [56] REFERENCES CITED</u>

"4,367,924  11/1983  Clark et al." should read
--4,367,924  1/1983  Clark et al.--.

<u>COLUMN 24</u>

Formula I-188, "$CHOC_5H_1$" should read --$CHOC_5H_{11}$--.

<u>COLUMN 62</u>

Line 12, "crystal." should read --crystal--.

<u>COLUMN 69</u>

Line 32, "second" should read --seconds--.

<u>COLUMN 101</u>

Line 21, "and SmA," should read --and SmA.--.

Signed and Sealed this

Twenty-second Day of March, 1994

Attest:

BRUCE LEHMAN

*Attesting Officer*          *Commissioner of Patents and Trademarks*